United States Patent
Kawamura et al.

(10) Patent No.: US 10,297,757 B2
(45) Date of Patent: May 21, 2019

(54) COMPOUND, MATERIAL FOR ORGANIC ELECTROLUMINESCENT ELEMENTS, ORGANIC ELECTROLUMINESCENT ELEMENT AND ELECTRONIC DEVICE

(71) Applicant: IDEMITSU KOSAN CO., LTD., Tokyo (JP)

(72) Inventors: Masahiro Kawamura, Chiba (JP); Yumiko Mizuki, Basel (CH); Hirokatsu Ito, Ichihara (JP); Tomoharu Hayama, Utsunomiya (JP); Tasuku Haketa, Chiba (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 219 days.

(21) Appl. No.: 15/112,977

(22) PCT Filed: Jan. 29, 2015

(86) PCT No.: PCT/JP2015/052481
§ 371 (c)(1),
(2) Date: Jul. 20, 2016

(87) PCT Pub. No.: WO2015/115530
PCT Pub. Date: Aug. 6, 2015

(65) Prior Publication Data
US 2016/0343950 A1    Nov. 24, 2016

(30) Foreign Application Priority Data
Jan. 31, 2014    (JP) .................................. 2014-017352

(51) Int. Cl.
| | | |
|---|---|---|
| *C07F 9/53* | (2006.01) | |
| *C07F 9/58* | (2006.01) | |
| *C07F 9/572* | (2006.01) | |
| *C07F 9/655* | (2006.01) | |
| *C09K 11/06* | (2006.01) | |
| *H01L 51/00* | (2006.01) | |
| *H01L 51/50* | (2006.01) | |
| *H05B 33/14* | (2006.01) | |
| *C07F 9/6553* | (2006.01) | |
| *C07F 9/6558* | (2006.01) | |

(52) U.S. Cl.
CPC ........ *H01L 51/0054* (2013.01); *C07F 9/5325* (2013.01); *C07F 9/5728* (2013.01); *C07F 9/58* (2013.01); *C07F 9/65517* (2013.01); *C07F 9/65586* (2013.01); *C07F 9/655354* (2013.01); *C09K 11/06* (2013.01); *H01L 51/0055* (2013.01); *H01L 51/5076* (2013.01); *H05B 33/14* (2013.01); *C09K 2211/1007* (2013.01); *C09K 2211/1011* (2013.01); *C09K 2211/1014* (2013.01); *C09K 2211/1029* (2013.01); *C09K 2211/1088* (2013.01); *C09K 2211/1092* (2013.01); *C09K 2211/1096* (2013.01); *H01L 51/5072* (2013.01)

(58) Field of Classification Search
CPC ...... C07F 9/5325; C07F 9/5728; C07F 9/587; C07F 9/65517; C07F 9/655354; C07F 9/65586; C09K 11/06; C09K 2211/1007; C09K 2211/1011; C09K 2211/1014; C09K 2211/1029; C09K 2211/1088; C09K 2211/1092; C09K 2211/1096; H01L 51/0054; H01L 51/5076; H05B 33/14
See application file for complete search history.

(56) References Cited

U.S. PATENT DOCUMENTS

| | | | | |
|---|---|---|---|---|
| 9,517,977 | B2 * | 12/2016 | Spreitzer ................. | C07B 59/00 |
| 2004/0076853 | A1 * | 4/2004 | Jarikov .................. | C09K 11/06 428/690 |
| 2007/0099024 | A1 * | 5/2007 | Nii .......................... | C09K 11/06 428/690 |
| 2015/0034927 | A1 * | 2/2015 | Nakano ................ | C07F 9/65517 257/40 |
| 2016/0211455 | A1 * | 7/2016 | Rothe .................. | H01L 51/0077 |

FOREIGN PATENT DOCUMENTS

| | | | |
|---|---|---|---|
| CN | CN-103187531 | A | 7/2013 |
| CN | 103319532 | A | 9/2013 |
| JP | 2002-063989 | A | 2/2002 |
| JP | 2004-204140 | A | 7/2004 |
| JP | 2006-073581 | A | 3/2006 |
| JP | 2009-179585 | A * | 8/2009 |

(Continued)

OTHER PUBLICATIONS

Machine translation of JP 2009-179585 A (publication date: Aug. 2009).*
Machine translation of CN 103187531 (publication date: Jul. 2013).*
Mallesham et al., "Phosphine oxide functionalized pyrenes as efficient blue light emitting multifunctional materials for organic light emitting diodes," Journal of Materials Chemistry C: Materials for Optical and Electronic Devices 3(6):1208-1224 (2015) (abstract only).

(Continued)

*Primary Examiner* — Dawn L Garrett
(74) *Attorney, Agent, or Firm* — Foley & Lardner LLP

(57) ABSTRACT

An organic electroluminescence device having higher performance, in particular exhibiting a better driving voltage and a better external quantum efficiency, while having an extended lifetime; and an electronic equipment provided with the organic electroluminescence device are provided. In addition, a compound for realizing the same device and equipment is provided. Specifically, a compound having a specific structure having a triphenylene skeleton; an organic electroluminescence device using the compound; and an electronic equipment provided with the organic electroluminescence device were provided.

20 Claims, 1 Drawing Sheet

(56) References Cited

FOREIGN PATENT DOCUMENTS

| KR | 10-2013-0129543 A | 11/2013 |
| --- | --- | --- |
| WO | WO-2012/173370 A2 | 12/2012 |
| WO | WO-2013/118507 A1 | 8/2013 |
| WO | WO-2013/182046 | 12/2013 |
| WO | WO-2014/167020 A1 | 10/2014 |

OTHER PUBLICATIONS

International Search Report for International Patent Application No. PCT/JP2015/052481 dated Apr. 21, 2015.
Japanese Office Action dated Aug. 7, 2018 in corresponding application No. 2015-560004.
Japanese Office Action dated Feb. 15, 2019 in corresponding application No. 2015-560004.

* cited by examiner

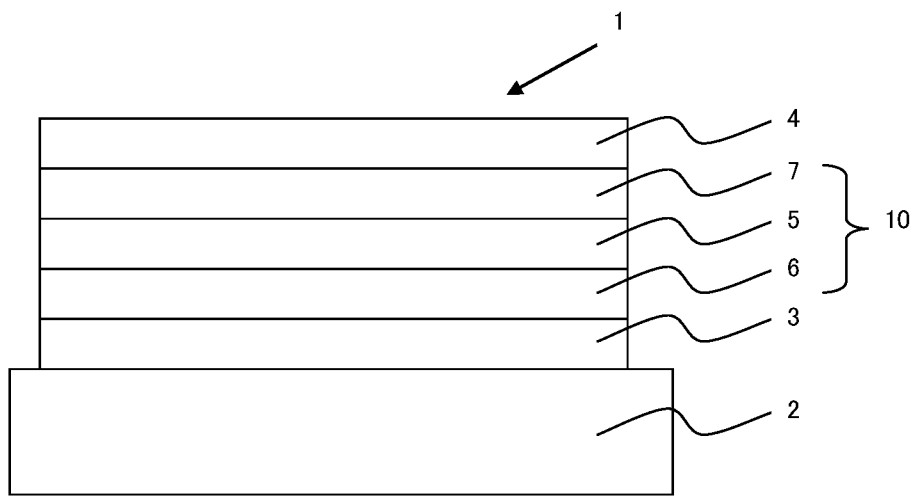

COMPOUND, MATERIAL FOR ORGANIC ELECTROLUMINESCENT ELEMENTS, ORGANIC ELECTROLUMINESCENT ELEMENT AND ELECTRONIC DEVICE

CROSS-REFERENCE TO RELATED APPLICATIONS

The present application is a U.S. national stage application of International Patent Application No. PCT/JP2015/052481, filed Jan. 29, 2015, which claims the benefit of priority to Japanese Patent Application No. 2014-017352, filed Jan. 31, 2014, the entireties of which are hereby incorporated by reference.

FIELD OF INVENTION

The present invention relates to a compound, a material for organic electroluminescence devices containing the compound, an organic electroluminescence device using the compound, and an electronic equipment provided with the organic electroluminescence device.

BACKGROUND ART

In general, an organic electroluminescence (EL) device is composed of an anode, a cathode, and one or more organic thin film layers interposed between the anode and the cathode. When a voltage is applied between the two electrodes, electrons from the cathode side and holes from the anode side are injected into a light emitting region. The injected electrons and holes are recombined in the light emitting region to produce an exited state, and when the exited state returns to the ground state, light is emitted.

Since in an organic EL device, a wide variety of luminescent colors can be obtained by using various light emitting materials for the light emitting layer, studies for practical use thereof for a display and the like are actively promoted. In particular, studies of light emitting materials of the three primary colors of red, green and blue are the most actively advanced and intensive studies are being conducted toward higher characteristics.

As such a material for organic EL devices, PTLs 1 to 4 disclose a phosphone oxide compound. However, in the field of organic EL devices, development of new materials is demanded for further enhancement of the performance of the devices.

CITATION LIST

Patent Literature

PTL 1: JP 2002-63989 A
PTL 2: JP 2006-73581 A
PTL 3: JP 2004-204140 A
PTL 4: KR 10-2013-0129543 A

SUMMARY OF INVENTION

Technical Problem

Thus, an object of the present invention is to provide an organic electroluminescence device having higher performance, specifically, exhibiting a better driving voltage and a better external quantum efficiency, while having an extended lifetime, and an electronic equipment provided with the organic electroluminescence device, and to provide a compound for achieving the same device and equipment.

Solution to Problem

As a result of intensive studies, the present inventors have found that a compound having a specific structure having a condensed ring having four or more rings can solve the above problem. The present invention has been completed based on the findings.

According to the present invention, the following [1] to [4] are provided.

[1] A compound represented by the following general formula (1):

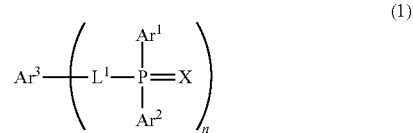

(1)

wherein in the general formula (1), X represents an oxygen atom, a sulfur atom or a selenium atom;

$L^1$ is a substituted or unsubstituted arylene group having 6 to 13 ring carbon atoms, a substituted or unsubstituted, oxygen-containing or sulfur-containing, heteroarylene group having 5 to 13 ring atoms;

$Ar^1$ and $Ar^2$ are each independently a substituted or unsubstituted aryl group having 6 to 60 ring carbon atoms, or a substituted or unsubstituted, oxygen-containing or sulfur-containing, heteroaryl group having 5 to 60 ring atoms, and $Ar^1$ and $Ar^2$ may bind to each other to form a ring;

$Ar^3$ is an aromatic condensed hydrocarbon group having substituted or unsubstituted condensed ring having four or more rings, or an oxygen-containing, sulfur-containing or selenium-containing, heteroaromatic condensed hydrocarbon group having substituted or unsubstituted condensed ring having four or more rings; and n is an integer of 1 to 3.

[2] A material for organic electroluminescence devices including the compound according to the above [1].

[3] An organic electroluminescence device including an anode and a cathode facing to each other, and one or more organic thin film layers including at least a light emitting layer, which are disposed between the anode and the cathode, wherein at least one layer of the organic thin film layers contains the compound according to the above [1].

[4] An electronic equipment provided with the organic electroluminescence device according to the above [3].

Advantageous Effects of Invention

According to the present invention, it is possible to provide an organic electroluminescence device having higher performance, specifically, exhibiting a better driving voltage and a better external quantum efficiency, while having an extended lifetime, and an electronic equipment provided with the organic electroluminescence device, and to further provide a compound for realizing the same device and equipment.

BRIEF DESCRIPTION OF DRAWINGS

The FIGURE shows an example of a schematic configuration of an organic electroluminescence device (hereinunder sometimes abbreviated to "organic EL device") according to an embodiment of the present invention.

DESCRIPTION OF EMBODIMENT

As used herein, the phrase "XX to YY carbon atoms" in the expression "a substituted or unsubstituted ZZ group having XX to YY carbon atoms" represents the carbon number in cases where the ZZ group is unsubstituted, and the carbon number of a substituent in cases where the ZZ group is substituted is not included. Here, "YY" is larger than "XX", and "XX" and "YY" each represent an integer of 1 or more.

In addition, a "hydrogen atom" includes isotopes having different neutron numbers, i.e., protium, deuterium and tritium. The word "unsubstituted" in the case of "substituted or unsubstituted" means that the group is not substituted with the substituent and hydrogen atoms bind to the group.

As used herein, the phrase "ring carbon atoms" represents a number of carbon atoms among the atoms constituting the ring itself of a compound having a structure in which atoms bind in a ring form (for example, a monocyclic compound, a condensed-ring compound, a crosslinked compound, a carbocyclic compound, a heterocyclic compound). In cases where the ring is substituted with a substituent, carbon contained in the substituent is not included in the ring carbon atoms. For the "ring carbon atoms" described below, the same is applied unless otherwise specified. For example, a benzene ring has 6 ring carbon atoms, a naphthalene ring has 10 ring carbon atoms, a pyridinyl group has 5 ring carbon atoms, and a furanyl group has 4 ring carbon atoms. In addition, when an alkyl group, for example, is substituted on a benzene ring or a naphthalene ring as a substituent, the carbon number of the alkyl group is not included in the number of the ring carbon atoms. In cases where a fluorene ring, for example, binds to a fluorene ring as a substituent (including a spirofluorene ring), the carbon number of the fluorene ring as the substituent is not included in the number of the ring carbon atoms.

The phrase "ring atoms" represents a number of atoms constituting the ring itself of a compound having a structure (for example, monocyclic, condensed ring, or ring-aggregation) where atoms bind in a ring form (for example, a monocyclic compound, a condensed-ring compound, a crosslinked compound, a carbocyclic compound, a heterocyclic compound). Atoms not constituting the ring (for example, a hydrogen atom terminating a bonding of an atom constituting the ring) or atoms included in a substituent in cases where the ring is substituted with the substituent are not included in the ring atoms. For the "ring atoms" described below, the same is applied unless otherwise specified. For example, a pyridine ring has 6 ring atoms, a quinazoline ring has 10 ring atoms, and a furan ring has 5 ring atoms. The hydrogen atoms respectively bound to carbon atoms in a pyridine ring or a quinazoline ring and atoms constituting a substituent are not included in the number of the ring atoms. In cases where a fluorene ring, for example, is bound to a fluorene ring as a substituent (including a spirofluorene ring), the atomic number of the fluorene ring as the substituent is not included in the number of the ring atoms.

The "heteroaryl group" as describe herein is a group containing at least one hetero atom as a ring atom, and the hetero atom is preferably one or more selected from a nitrogen atom, an oxygen atom, a sulfur atom and a selenium atom. Similarly, the "heteroaromatic ring" is a ring containing at least one hetero atom as a ring atom, and the hetero atom is preferably one or more selected from a nitrogen atom, an oxygen atom, a sulfur atom and a selenium atom.

As used herein, the "substituted or unsubstituted carbazolyl group" includes, in addition to the following carbazolyl group:

[Chem. 2]

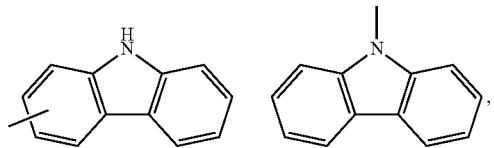

and a substituted carbazolyl group having any of the substituents described above, for example, the following substituted carbazolyl group.

[Chem. 3]

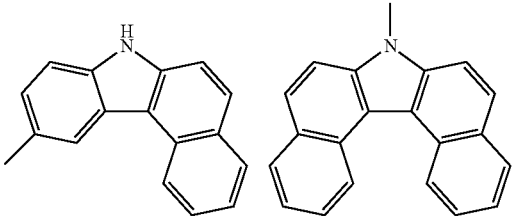

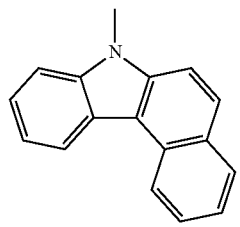

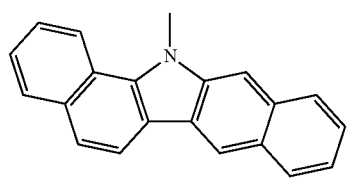

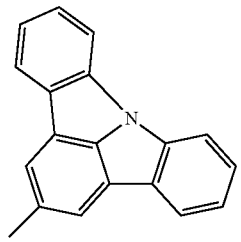

As used herein, a substituted or unsubstituted dibenzofuranyl group and a substituted or unsubstituted dibenzothiophenyl group include, in addition to the following dibenzofuranyl group and dibenzothiophenyl group:

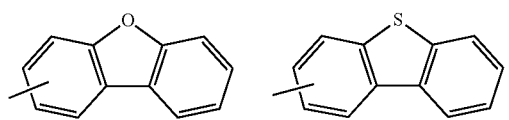

and substituted dibenzofuranyl group and substituted dibenzothiophenyl group having any of the substituents described above, for example, the following substituted dibenzofuranyl group and substituted dibenzothiophenyl group [in the formulae, X represents an oxygen atom or a sulfur atom, Y represents an oxygen atom, a sulfur atom, NH, NR$^a$ (R$^a$ is an alkyl group or an aryl group), CH$_2$, or CR$^b{}_2$ (R$^b$ is an alkyl group or an aryl group)].

[Chem. 5]

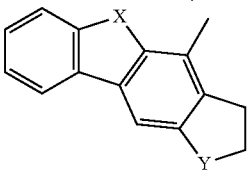

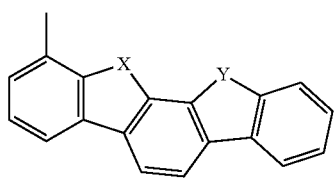

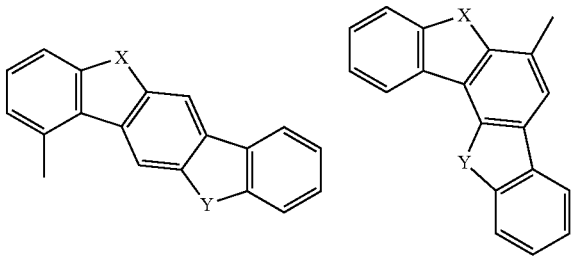

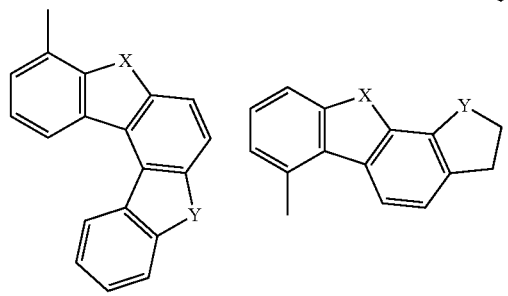

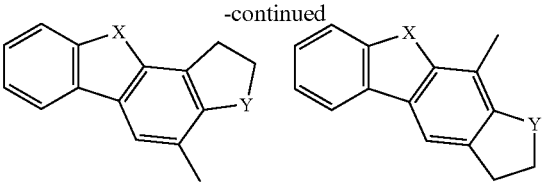

-continued

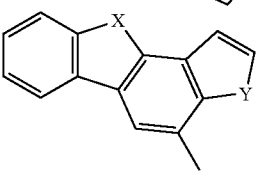

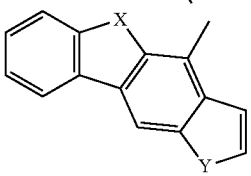

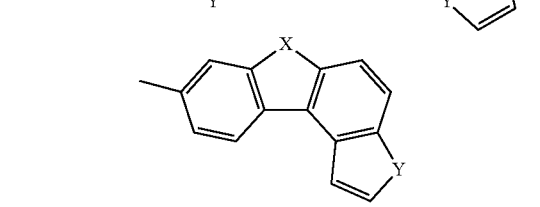

As used herein, any substituent in the case of saying "substituted or unsubstituted" and the substituent in the case of saying simply "a substituent" are, unless otherwise limited, preferably at least one selected from the group consisting of: an alkyl group having 1 to 50 (preferably 1 to 18, more preferably 1 to 8) carbon atoms; a cycloalkyl group having 3 to 50 (preferably 3 to 10, more preferably 3 to 8, further preferably 5 or 6) ring carbon atoms; an aryl group having 6 to 50 (preferably 6 to 25, more preferably 6 to 18) ring carbon atoms; an aralkyl group with 7 to 51 (preferably 7 to 30, more preferably 7 to 20) carbon atoms having an aryl group with 6 to 50 (preferably 6 to 25, more preferably 6 to 18) ring carbon atoms; an amino group; a mono-substituted or di-substituted amino group having a substituent selected from an alkyl group having 1 to 50 (preferably 1 to 18, more preferably 1 to 8) carbon atoms and an aryl group having 6 to 50 (preferably 6 to 25, more preferably 6 to 18) ring carbon atoms; an alkoxy group having an alkyl group with 1 to 50 (preferably 1 to 18, more preferably 1 to 8) carbon atoms; an aryloxy group having an aryl group with 6 to 50 (preferably 6 to 25, more preferably 6 to 18) ring carbon atoms; a mono-substituted, di-substituted or tri-substituted silyl group having a substituent selected from an alkyl group having 1 to 50 (preferably 1 to 18, more preferably 1 to 8) carbon atoms and an aryl group having 6 to 50 (preferably 6 to 25, more preferably 6 to 18) ring carbon atoms; a heteroaryl group having 5 to 50 (preferably 5 to 24, more preferably 5 to 13) ring atoms; a haloalkyl group having 1 to 50 (preferably 1 to 18, more preferably 1 to 8) carbon atoms; a halogen atom (a fluorine atom, a chlorine atom, a bromine atom or a iodine atom); a cyano group; a nitro group; a sulfonyl group having a substituent selected from an alkyl group having 1 to 50 (preferably 1 to 18, more preferably 1 to 8) carbon atoms and an aryl group having 6 to 50 (preferably 6 to 25, more preferably 6 to 18) ring carbon atoms; a di-substituted phosphoryl group having a substituent selected from an alkyl group having 1 to 50 (preferably 1 to 18, more preferably 1 to 8) carbon atoms and an aryl group having 6 to 50 (preferably 6 to 25, more preferably 6 to 18) ring carbon atoms; an alkylsulfonyloxy group; an arylsulfonyloxy group; an alkylcarbonyloxy group; an arylcarbonyloxy group; a boron-containing group; a zinc-containing group; a tin-containing group; a silicon-containing group; a magnesium-containing group; a lithium-containing group; a hydroxy group; an alkyl-substituted or aryl-substituted carbonyl group; a carboxyl group; a vinyl group; a (meth)acryloyl group; an epoxy group; and an oxetanyl group.

The substituents may be further substituted with any of the substituents described above. The substituents may bind to each other to form a ring.

Among the substituents above, more preferred are a substituted or unsubstituted alkyl group having 1 to 50 (preferably 1 to 18, more preferably 1 to 8) carbon atoms, a substituted or unsubstituted cycloalkyl group having 3 to 50 (preferably 3 to 10, more preferably 3 to 8, further preferably 5 or 6) ring carbon atoms, a substituted or unsubstituted aryl group having 6 to 50 (preferably 6 to 25, more preferably 6 to 18) ring carbon atoms, a mono-substituted or di-substituted amino group having a substituent selected form a substituted or unsubstituted alkyl group with 1 to 50 (preferably 1 to 18, more preferably 1 to 8) carbon atoms and a substituted or unsubstituted aryl group with 6 to 50 (preferably 6 to 25, more preferably 6 to 18) ring carbon atoms, a substituted or unsubstituted heteroaryl group having 5 to 50 (preferably 5 to 24, more preferably 5 to 13) ring atoms, a halogen atom, and a cyano group.

The haloalkyl group is an alkyl group in which one or more, preferably 1 to 15, more preferably 1 to 7 hydrogen atoms or all of the hydrogen atoms are substituted with the same or different halogen atoms (fluorine atoms, chlorine atoms, bromine atoms or iodine atoms). Specific examples, preferred examples, and more preferred examples of the alkyl group are the same as the alkyl group mentioned above. Specifically, the examples include a trifluoromethyl group, a pentafluoroethyl group, and a heptafluoropropyl group.

As used herein, a preferred definition can be arbitrary selected, and a combination of preferred definitions can also be said to be preferred.

[Compound]

The compound of the present invention which is useful as a material for organic electroluminescence devices is represented by the following general formula (1).

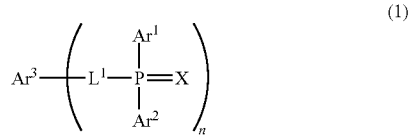

(1)

In the general formula (1), X represents an oxygen atom, a sulfur atom or a selenium atom;

$L^1$ is a substituted or unsubstituted arylene group having 6 to 13 ring carbon atoms, a substituted or unsubstituted, oxygen-containing or sulfur-containing, heteroarylene group having 5 to 13 ring atoms;

$Ar^1$ and $Ar^2$ are each independently a substituted or unsubstituted aryl group having 6 to 60 ring carbon atoms or a substituted or unsubstituted, oxygen-containing or sulfur-containing, heteroaryl group having 5 to 60 ring atoms, and $Ar^1$ and $Ar^2$ may bind to each other to form a ring;

$Ar^3$ is an aromatic condensed hydrocarbon group having substituted or unsubstituted condensed ring having four or more rings, or an oxygen-containing, sulfur-containing or selenium-containing, heteroaromatic condensed hydrocarbon group having substituted or unsubstituted condensed ring having four or more rings; and n is an integer of 1 to 3.

X in the general formula (1) represents an oxygen atom, a sulfur atom or a selenium atom, preferably an oxygen atom or a sulfur atom, more preferably an oxygen atom.

$L^1$ is a substituted or unsubstituted arylene group having 6 to 13 ring carbon atoms or a substituted or unsubstituted, oxygen-containing or sulfur-containing, heteroarylene group having 5 to 13 ring atoms.

The number of the ring carbon atoms of the arylene group is, from the viewpoint of allowing the organic EL device to exhibit a good driving voltage and a good external quantum efficiency and have an extended lifetime, preferably 6 to 12, more preferably 6 to 10, further preferably 6. Examples of the arylene group include a phenylene group, a naphthylene group (a 1,4-naphthylene group, a 1,5-naphthylene group, etc.), a biphenylylene group, a fluorenylene group (a 2,7-fluorenylene group, etc.), a 9,9-di-substituted fluorenylene group (a 9,9-dimethyl-2,7-fluorenylene group, a 9,9-diphenyl-2,7-fluorenylene group, etc.), a benzofluorenylene group, a dibenzofluorenylene group, an s-indacenylene group and an as-indacenylene group. Among them, from the viewpoint of allowing the organic EL device to exhibit a good driving voltage and a good external quantum efficiency and have an extended lifetime, a phenylene group, a biphenylylene group, a fluorenylene group, a dibenzofuranylene group, and a dibenzothiophenylene group are preferred, a phenylene group is more preferred, and a 1,4-phenylene group is further preferred.

The number of the ring atoms of the oxygen-containing or sulfur-containing heteroarylene group is, from the viewpoint of allowing the organic EL device to exhibit a good driving voltage and a good external quantum efficiency and have an extended lifetime, preferably 5 to 12, more preferably 5 to 10, further preferably 5 to 9, especially preferably 5. The oxygen-containing or sulfur-containing heteroarylene group is required only to have at least one selected from an oxygen atom and a sulfur atom, and as long as this condition is satisfied, a nitrogen atom, etc. may further be contained. Examples of the oxygen-containing or sulfur-containing heteroarylene group include a divalent oxygen-containing heterocyclic group such as a furanylene group, a benzofuranylene group, an isobenzofuranylene group, a dibenzofuranylene group (a 2,8-dibenzofuranylene group, etc.), an oxazolylene group, an oxadiazolylene group, a benzoxazolylene group and a dinaphthofuranylene group; and a divalent sulfur-containing heterocyclic group such as a thiophenylene group, a benzothiophenylene group, a dibenzothiophenylene group (a 2,8-dibenzothiophenylene group, etc.), a thiazolylene group, a thiadiazolylene group and a benzothiazolylene group.

Among them, from the viewpoint of allowing the organic EL device to exhibit a good driving voltage and a good external quantum efficiency and have an extended lifetime, $L^1$ is preferably a substituted or unsubstituted arylene group having 6 to 13 ring carbon atoms, and more preferably a substituted or unsubstituted phenylene group, a substituted or unsubstituted biphenylylene group, a substituted or unsubstituted fluorenylene group, a substituted or unsubstituted dibenzofuranylene group, or a substituted or unsubstituted dibenzothiophenylene group.

Incidentally, in cases where the aromatic condensed hydrocarbon group or the heteroaromatic condensed hydrocarbon group represented by $L^1$ has a substituent, preferred examples of the substituent include the substituents listed above except for an aryl group and a heteroaryl group. Specifically the substituent is preferably at least one selected from the group consisting of an alkyl group having 1 to 50 (preferably 1 to 18, more preferably 1 to 8) carbon atoms; a cycloalkyl group having 3 to 50 (preferably 3 to 10, more preferably 3 to 8, further preferably 5 or 6) ring carbon atoms; an aralkyl group with 7 to 51 (preferably 7 to 30, more preferably 7 to 20) carbon atoms having an aryl group with 6 to 50 (preferably 6 to 25, more preferably 6 to 18) ring carbon atoms; amino group; a mono-substituted or di-substituted amino group having a substituent selected from an alkyl group having 1 to 50 (preferably 1 to 18, more preferably 1 to 8) carbon atoms and an aryl group having 6 to 50 (preferably 6 to 25, more preferably 6 to 18) ring carbon atoms; an alkoxy group having an alkyl group with 1 to 50 (preferably 1 to 18, more preferably 1 to 8) carbon atoms; an aryloxy group having an aryl group with 6 to 50 (preferably 6 to 25, more preferably 6 to 18) ring carbon atoms; a mono-substituted, di-substituted or tri-substituted silyl group having a substituent selected from an alkyl group having 1 to 50 (preferably 1 to 18, more preferably 1 to 8) carbon atoms and an aryl group having 6 to 50 (preferably 6 to 25, more preferably 6 to 18) ring carbon atoms; a haloalkyl group having 1 to 50 (preferably 1 to 18, more preferably 1 to 8) carbon atoms; a halogen atom (a fluorine atom, a chlorine atom, a bromine atom or a iodine atom); a cyano group; a nitro group; a sulfonyl group having a substituent selected from an alkyl group having 1 to 50 (preferably 1 to 18, more preferably 1 to 8) carbon atoms and an aryl group having 6 to 50 (preferably 6 to 25, more preferably 6 to 18) ring carbon atoms; a di-substituted phosphoryl group having a substituent selected form an alkyl group having 1 to 50 (preferably 1 to 18, more preferably 1 to 8) carbon atoms and an aryl group having 6 to 50 (preferably 6 to 25, more preferably 6 to 18) ring carbon atoms; an alkylsulfonyloxy group; an arylsulfonyloxy group; an alkylcarbonyloxy group; an arylcarbonyloxy group; a boron-containing group; a zinc-containing group; a tin-containing group; a silicon-containing group; a magnesium-containing group; a lithium-containing group; a hydroxy group; an alkyl-substituted or aryl-substituted carbonyl group; a carboxyl group; a vinyl group; a (meth) acryloyl group; an epoxy group; and an oxetanyl group.

Among the substituents above, more preferred are a substituted or unsubstituted alkyl group having 1 to 50 (preferably 1 to 18, more preferably 1 to 8) carbon atoms, a substituted or unsubstituted cycloalkyl group having 3 to 50 (preferably 3 to 10, more preferably 3 to 8, further preferably 5 or 6) ring carbon atoms, a substituted or unsubstituted aryl group having 6 to 50 (preferably 6 to 25, more preferably 6 to 18) ring carbon atoms, a mono-substituted or di-substituted amino group having a substituent selected from a substituted or unsubstituted alkyl group having 1 to 50 (preferably 1 to 18, more preferably 1 to 8) carbon atoms and a substituted or unsubstituted aryl group having 6 to 50 (preferably 6 to 25, more preferably 6 to 18) ring carbon atoms, a substituted or unsubstituted heteroaryl group having 5 to 50 (preferably 5 to 24, more preferably 5 to 13) ring atoms, a halogen atom, and a cyano group.

$Ar^1$ and $Ar^2$ in the general formula (1) are each independently a substituted or unsubstituted aryl group having 6 to 60 ring carbon atoms or oxygen-containing or sulfur-containing heteroaryl group having 5 to 60 ring atoms, and $Ar^1$ and $Ar^2$ may bind to each other to form a ring.

The number of the ring carbon atoms of the aryl group is, from the viewpoint of allowing the organic EL device to exhibit a good driving voltage and a good external quantum efficiency and have an extended lifetime, preferably 6 to 40, more preferably 6 to 20, further preferably 6 to 14, especially preferably 6 to 12. Examples of the aryl group include a phenyl group, a naphthyl group (a 1-naphthyl group, a 2-naphthyl group), an anthryl group (a 1-anthryl group, a 2-anthryl group, etc.), a benzanthryl group, a phenanthryl group (a 1-phenanthryl group, a 2-phenanthryl group, a 3-phenanthryl group, a 9-phenanthryl group, etc.), a benzophenanthryl group, a fluorenyl group, a 9,9-di-substituted fluorenyl group (a 9,9-dimethyl-2-fluorenyl group, a 9,9-diphenyl-2-fluorenyl group, etc.), a benzofluorenyl group, a dibenzofluorenyl group, a picenyl group, a tetracenyl group, a pentacenyl group, a pyrenyl group, a chrysenyl group, a benzochrysenyl group, an s-indacenyl group, an as-indacenyl group, a fluoranthenyl group, a benzofluoranthenyl group, a triphenylenyl group, a benzotriphenylenyl group, a perylenyl group, a coronenyl group, and a dibenzanthryl group. Among them, from the viewpoint of allowing the organic EL device to exhibit a good driving voltage and a good external quantum efficiency and have an extended lifetime, a phenyl group and a naphthyl group are preferred, and a phenyl group is more preferred.

The oxygen-containing or sulfur-containing heteroaryl group is required only to have at least one selected from an oxygen atom and a sulfur atom, and as long as this condition is satisfied, a nitrogen atom, etc. may further be contained. Incidentally, in a compound of one embodiment of the present invention, a heteroaryl group containing no nitrogen atom is preferred.

The number of the ring atoms of the oxygen-containing or sulfur-containing heteroaryl group is, from the viewpoint of allowing the organic EL device to exhibit a good driving voltage and a good external quantum efficiency and have an extended lifetime, preferably 5 to 40, more preferably 5 to 20, further preferably 5 to 14, especially preferably 5 to 12. Examples of the heteroaryl group include a monovalent oxygen-containing heterocyclic group such as a furanyl group, a benzofuranyl group, an isobenzofuranyl group, a dibenzofuranyl group (a 2-dibenzofuranyl group, etc.), an oxazolyl group, an oxadiazolyl group, a benzoxazolyl group, a benzonaphthofuranyl group and a dinaphthofuranyl group; and a monovalent sulfur-containing heterocyclic group such as a benzothiophenyl group, a dibenzothiophenyl group (a 2-dibenzothiophenyl group, etc.), a thiophenyl group, a thiazolyl group, a thiadiazolyl group, a benzothiazolyl group, a benzonaphthothiophenyl group and a dinaphthothiophenyl group.

In cases where $Ar^1$ and $Ar^2$ bind to each other to form a ring, examples of the general formula (1) include the following structure.

[Chem. 7]

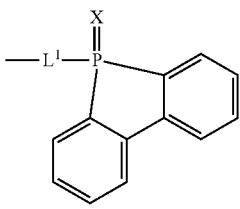

In a compound of one embodiment of the present invention, from the viewpoint of allowing the organic EL device to exhibit a good driving voltage and a good external quantum efficiency and have an extended lifetime, preferably, at least one of $Ar^1$ and $Ar^2$ is a substituted or unsubstituted aryl group having 6 to 60 ring carbon atoms, more preferably, both of $Ar^1$ and $Ar^2$ are a substituted or unsubstituted aryl group having 6 to 60 ring carbon atoms, further preferably, both of $Ar^1$ and $Ar^2$ are a substituted or unsubstituted aryl group having 6 to 13 ring carbon atoms, and especially preferably, $Ar^1$ and $Ar^2$ are each independently a substituted or unsubstituted phenyl group, a substituted or unsubstituted naphthyl group, a substituted or unsubstituted biphenylyl group or a substituted or unsubstituted fluorenyl group.

$Ar^3$ in the general formula (1) is an aromatic condensed hydrocarbon group having substituted or unsubstituted condensed ring having four or more rings, or an oxygen-containing, sulfur-containing or selenium-containing, heteroaromatic condensed hydrocarbon group having substituted or unsubstituted condensed ring having four or more rings. Here, the "condensed ring" means, as in the common definition in the chemistry, a ring which bind to each other with two atoms shared together. Even when a substituent substituted on the condensed ring is a cyclic group, the cyclic group is not included in the "condensed ring". That is, the "condensed ring having four or more rings" means that even when any ring is focused among the four or more rings, the ring necessarily binds to at least one other ring with two atoms shared together. In the case of, for example, a condensed ring having four rings, all of the four rings each bind to at least one other ring with two atoms shared together, and in the case of a condensed ring having six rings, all of the six rings each bind to at least one other ring with two atoms shared together.

In addition, in any of the aromatic condensed hydrocarbon group and oxygen-containing, sulfur-containing or selenium-containing heteroaromatic condensed hydrocarbon group, from the viewpoint of allowing the organic EL device to exhibit a good driving voltage and a good external quantum efficiency and have an extended lifetime, such a group preferably has a condensed ring having 4 to 10 rings, more preferably a condensed ring having 4 to 8 rings, further preferably a condensed ring having 4 to 7 rings, especially preferably a condensed ring having 4 to 6 rings.

Examples of the aromatic condensed hydrocarbon group having a condensed ring having four or more rings include residues of pyrene, chrysene, benzochrysene, benzanthracene, dibenzanthracene, benzophenanthrene, dibenzophenanthrene, triphenylene, benzofluorene, dibenzofluorene, fluoranthene, benzofluoranthene, and the like. The "residue" as used herein refers to, in cases where the aromatic condensed hydrocarbon group having a condensed ring having four or more rings is a monovalent group, a monovalent group after one hydrogen atom is eliminated, and in the case of n-valent group, the "residue" refers to an n-valent group after n hydrogen atoms are eliminated.

The oxygen-containing, sulfur-containing or selenium-containing heteroaromatic condensed hydrocarbon group having a condensed ring having four or more rings is required only to have at least one selected from an oxygen atom, a sulfur atom and a selenium atom, as long as this condition is satisfied, a nitrogen atom may further be contained. Incidentally, in a compound of one embodiment of the present invention, the heteroaromatic condensed hydrocarbon group preferably contains no nitrogen atom.

Examples of the oxygen-containing, sulfur-containing or selenium-containing heteroaromatic condensed hydrocarbon group having a condensed ring having four or more rings include an oxygen-containing heteroaromatic condensed hydrocarbon group such as residues of benzonaphthofuran, dinaphthofuran, and the like; a sulfur-containing heteroaromatic condensed hydrocarbon group such as residues of benzonaphthothiophene, dinaphthothiophene, and the like; a selenium-containing heteroaromatic condensed hydrocarbon group such as residues of benzonaphthoselenophene, dinaphthoselenophene, and the like; and a heteroaromatic condensed hydrocarbon group in which at least two selected from the oxygen-containing heteroaromatic condensed hydrocarbon group, the sulfur-containing heteroaromatic condensed hydrocarbon group and the selenium-containing heteroaromatic condensed hydrocarbon group bind to each other. As used herein, the "residue" refers to, in cases where the oxygen-containing, sulfur-containing or selenium-containing heteroaromatic condensed hydrocarbon group having a condensed ring having four or more rings is a monovalent group, a monovalent group after one hydrogen atom is eliminated, and in the case of n-valent group, the "residue" refers to an n-valent group after n hydrogen atoms are eliminated.

In addition, n is an integer of 1 to 3, and from the viewpoint of allowing the organic EL device to exhibit a good driving voltage and a good external quantum efficiency and have an extended lifetime, preferably 1 or 2, more preferably 1. When n=1, the general formula (1) is represented by the following general formula (1'):

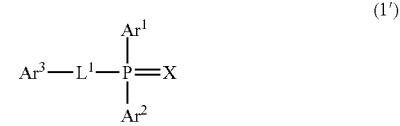

(1')

wherein in the general formula (1'), X, $L^1$ and $Ar^1$ to $Ar^3$ are the same as in the general formula (1), and the preferred examples are also the same.

In a compound of one embodiment of the present invention, from the viewpoint of allowing the organic EL device to exhibit a good driving voltage and a good external quantum efficiency and have an extended lifetime, in the general formula (1), $L^1$ is preferably a substituted or unsubstituted phenylene group, that is, the compound is preferably represented by the following general formula (1-1):

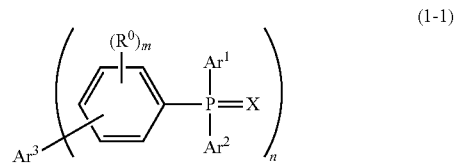

(1-1)

wherein in the general formula (1-1), X, $Ar^1$ to $Ar^3$ and n are the same as in the general formula (1), and the preferred examples are also the same; $R^0$ is a substituent; and m is an integer of 0 to 4, and when m is an integer of 2 to 4, the plural $R^0$'s may be the same as or different to one another.

In the general formula (1-1), as the substituent represented by $R^0$, the substituents listed above except for an aryl group and heteroaryl group are preferred, and examples thereof include the same substituents as those represented by $L^1$, and m is preferably 0 or 1, and more preferably 0.

In the general formula (1-1), from the viewpoint of allowing the organic EL device to exhibit a good driving voltage and a good external quantum efficiency and have an extended lifetime, $Ar^3$ is preferably bound to the p-position on the phenylene group with respect to the phosphorus atom which bonds to the phenylene group.

In the aromatic condensed hydrocarbon group having a condensed ring having four or more rings represented by $Ar^3$ in the general formula (1), in a compound of one embodiment of the present invention, from the viewpoint of allowing the organic EL device to exhibit a good driving voltage and a good external quantum efficiency and have an extended lifetime, the "a condensed ring having four or more rings" is a condensed ring constituted only of 6-membered rings. Examples of the condensed ring constituted only of 6-membered rings include a substituted or unsubstituted naphthacene, a substituted or unsubstituted pyrene, a substituted or unsubstituted chrysene, a substituted or unsubstituted triphenylene, a substituted or unsubstituted benzotriphenylene, a substituted or unsubstituted benzanthracene, a substituted or unsubstituted dibenzanthracene, a substituted or unsubstituted benzophenanthrene, a substituted or unsubstituted benzochrysene, and a substituted or unsubstituted naphthanthracene. Among them, from the viewpoint of allowing the organic EL device to exhibit a good driving voltage and a good external quantum efficiency and have an extended lifetime, a substituted or unsubstituted pyrene, a substituted or unsubstituted triphenylene, a substituted or unsubstituted benzotriphenylene, a substituted or unsubstituted dibenzanthracene, and a substituted or unsubstituted benzochrysene are preferred. In addition, as the compound in which "the condensed ring having four or more rings" is a condensed ring constituted only of 6-membered rings, from the viewpoint of allowing the organic EL device to exhibit a good driving voltage and a good external quantum efficiency and have an extended lifetime, the compound represented by any one of the following general formulae (10) to (16) is preferred:

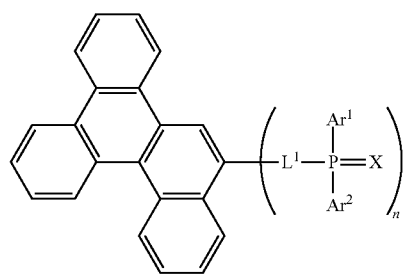
(10)

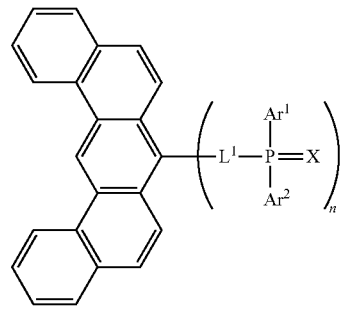
(11)

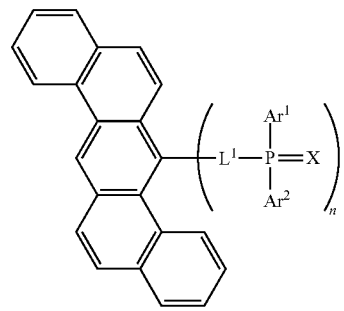
(12)

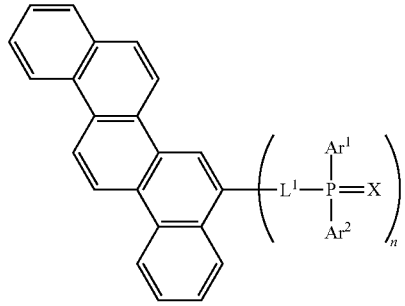
(13)

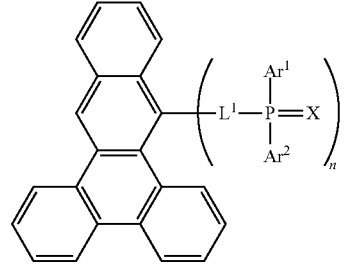
(14)

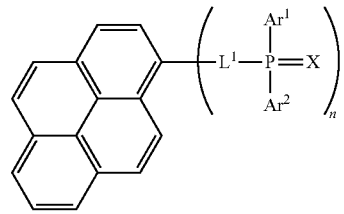
(15)

-continued

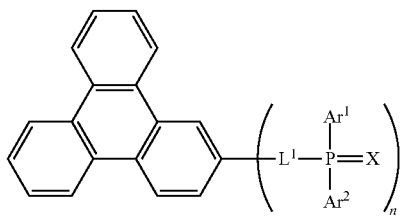

(16)

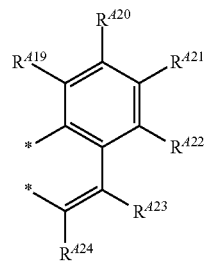

(A-iii)

wherein in the above formulae, the pyrene ring, the triphenylene ring, the benzotriphenylene ring, the dibenzanthracene ring and the benzochrysene ring each are a substituted or unsubstituted ring; and X, $L^1$, $Ar^1$ and $Ar^2$ are as defined above, and the preferred examples are also as defined above.

On the other hand, in a compound of one embodiment of the present invention, it is also preferred that the aromatic condensed hydrocarbon group represented by $Ar^3$ in the general formula (1) is represented by the following general formula (A). Incidentally, needless to say, the group represented by the general formula (A) contains a 5-membered ring in the condensed ring:

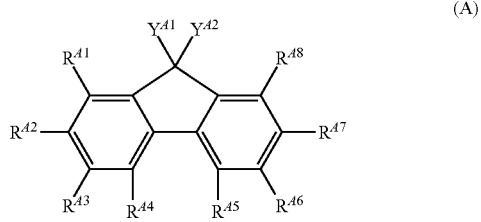

(A)

wherein in the general formula (A), $Y^{41}$ and $Y^{42}$ are each independently a hydrogen atom, an alkyl group having 1 to 10 carbon atoms, an aryl group having 6 to 30 ring carbon atoms or a heteroaryl group having 5 to 30 ring atoms; and $R^{41}$ to $R^{48}$ are each independently a hydrogen atom or a substituent, provided that at least one combination selected from $R^{41}$ and $R^{42}$, $R^{42}$ and $R^{43}$, $R^{43}$ and $R^{44}$, $R^{45}$ and $R^{46}$, $R^{46}$ and $R^{47}$, and $R^{47}$ and $R^{48}$ binds to form any of the rings represented by the following general formulae (A-i) to (A-iii):

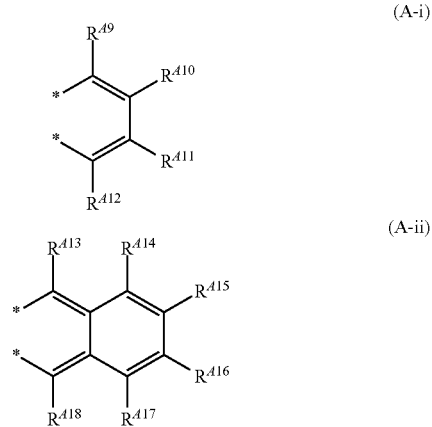

(A-i)

(A-ii)

wherein in the general formulae (A-i) to (A-iii), * represents a bonding site to a carbon atom; and $R^{49}$ to $R^{424}$ are each independently a hydrogen atom or a substituent;

provided that, at least one of $R^{41}$ to $R^{48}$ in the general formula (A) and $R^{49}$ to $R^{424}$ in the general formulae (A-i) to (A-iii) represents a direct bond to $L^1$ mentioned above.

Examples of the alkyl group having 1 to 10 carbon atoms represented by $Y^{41}$ and $Y^{42}$ include a methyl group, an ethyl group, various propyl groups ("various" means to include linear form and all branched forms, and the same is applied hereinunder), various pentyl group, various octyl group, and various decyl group. The carbon number of the alkyl group is preferably 1 to 6, more preferably 1 to 3, further preferably 1.

Examples of the aryl group having 6 to 30 ring carbon atoms represented by $Y^{41}$ and $Y^{42}$ include a phenyl group, a naphthyl group, an anthryl group, and a phenanthryl group. The number of the ring carbon atoms of the aryl group is preferably 6 to 14, more preferably 6 to 12, further preferably 6 to 10.

Examples of the heteroaryl group having 5 to 30 ring atoms represented by $Y^{41}$ and $Y^{42}$ include a pyridyl group, a furanyl group, a thiophenyl group, and a thiazolyl group. The number of the ring atoms of the heteroaryl group is preferably 5 to 20, more preferably 5 to 14, further preferably 5 to 12.

Among them, as $Y^{41}$ and $Y^{42}$, an alkyl group having 1 to 10 carbon atoms or an aryl group having 6 to 30 ring carbon atoms are preferred.

As examples of substituents represented by $R^{41}$ to $R^{48}$ and $R^{49}$ to $R^{424}$, the same examples may be exemplified as for the substituent represented by $L^1$ mentioned above, and in addition, an aryl group having 6 to 50 (preferably 6 to 25, more preferably 6 to 18) ring carbon atoms and a heteroaryl group having 5 to 50 (preferably 5 to 24, more preferably 5 to 13) ring atoms may be mentioned as a preferred substituent.

Here, in cases where a substituent represented by $R^{41}$ to $R^{48}$ or $R^{49}$ to $R^{424}$ is a heteroaryl group, any of an oxygen-containing heteroaryl group, a sulfur-containing heteroaryl group and a selenium-containing heteroaryl group is preferred, and among them, a heteroaryl group containing no nitrogen atom is more preferred.

It is also preferred that all of $R^{41}$ to $R^{48}$ and $R^{49}$ to $R^{424}$ are a hydrogen atom (provided that at least one of $R^{41}$ to $R^{48}$ in the general formula (A) and $R^{49}$ to $R^{424}$ in the general formulae (A-i) to (A-iii) represents a direct bond to $L^1$ mentioned above).

In the general formula (A), $R^{46}$ preferably represents a direct bond to $L^1$ mentioned above.

In cases where at least one combination selected from $R^{41}$ and $R^{42}$, $R^{42}$ and $R^{43}$, $R^{43}$ and $R^{44}$, $R^{45}$ and $R^{46}$, $R^{46}$ and $R^{47}$, and $R^{47}$ and $R^{48}$ binds to form any of the rings represented by the general formulae (A-i) to (A-iii), the aromatic condensed hydrocarbon group represented by Ar³ is specifically represented by any one of the following general formulae (A-a-i) to (A-f-iii-2). [The definitions of groups in each formula are the same as in the general formulae (A) and (A-i) to (A-iii), and the preferred examples are also the same. Incidentally, the same signs in a formula, if any, may be the same or different.]
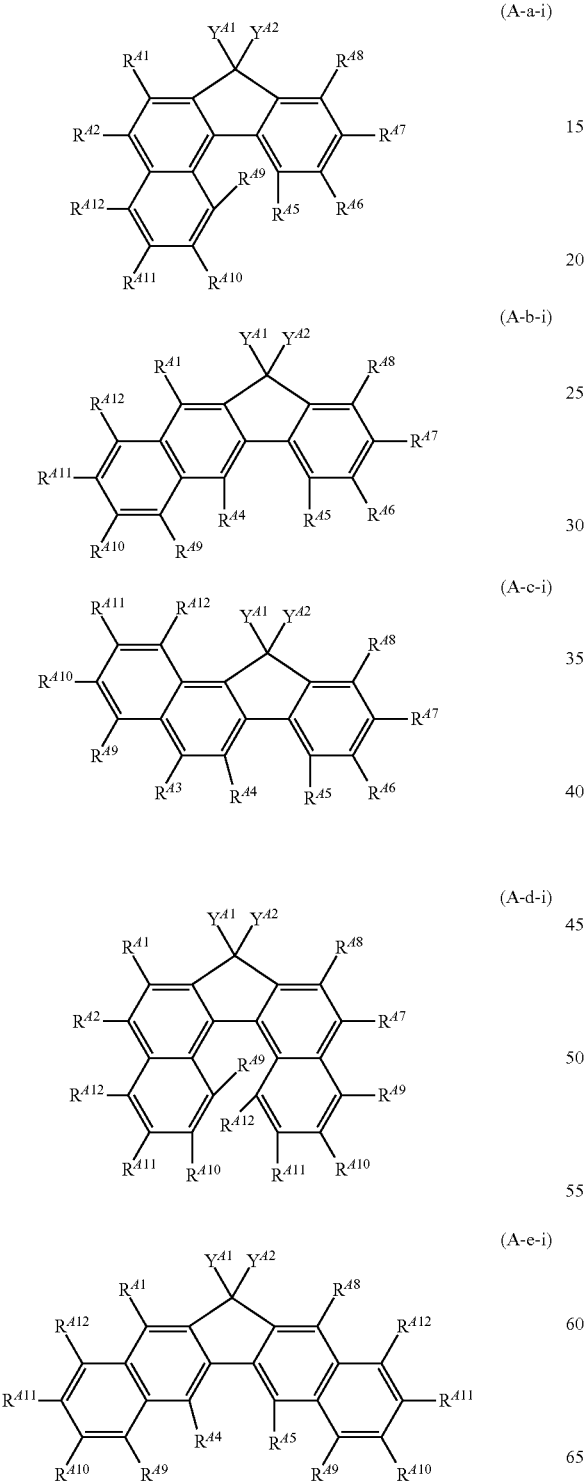
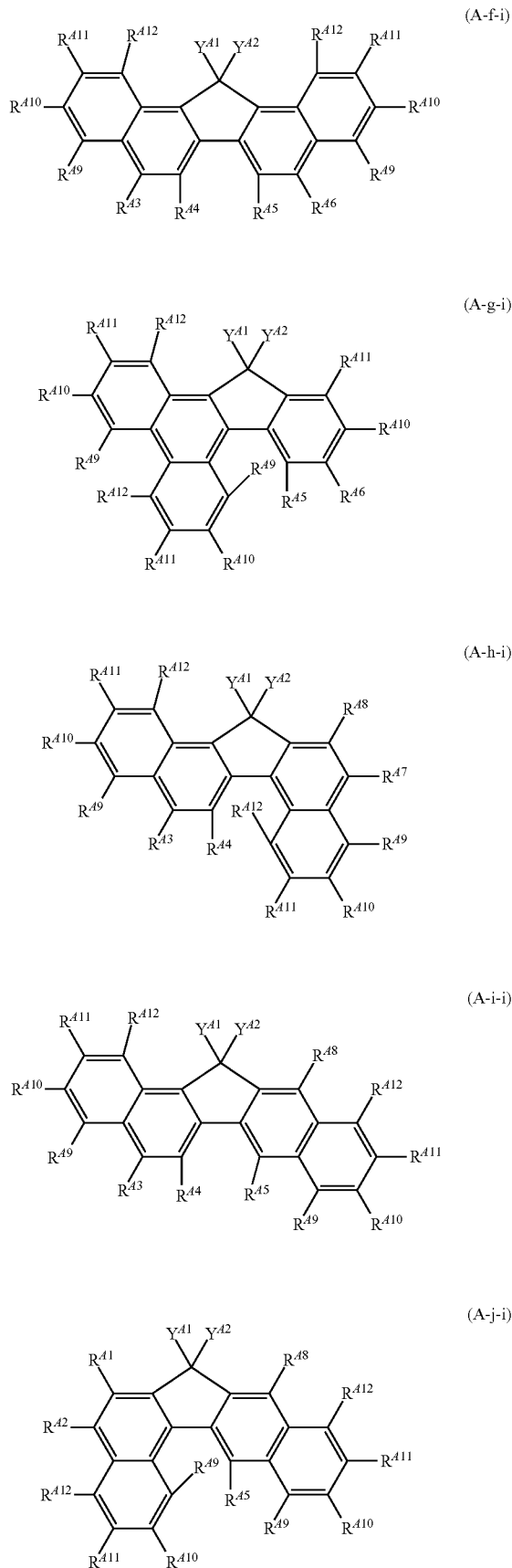

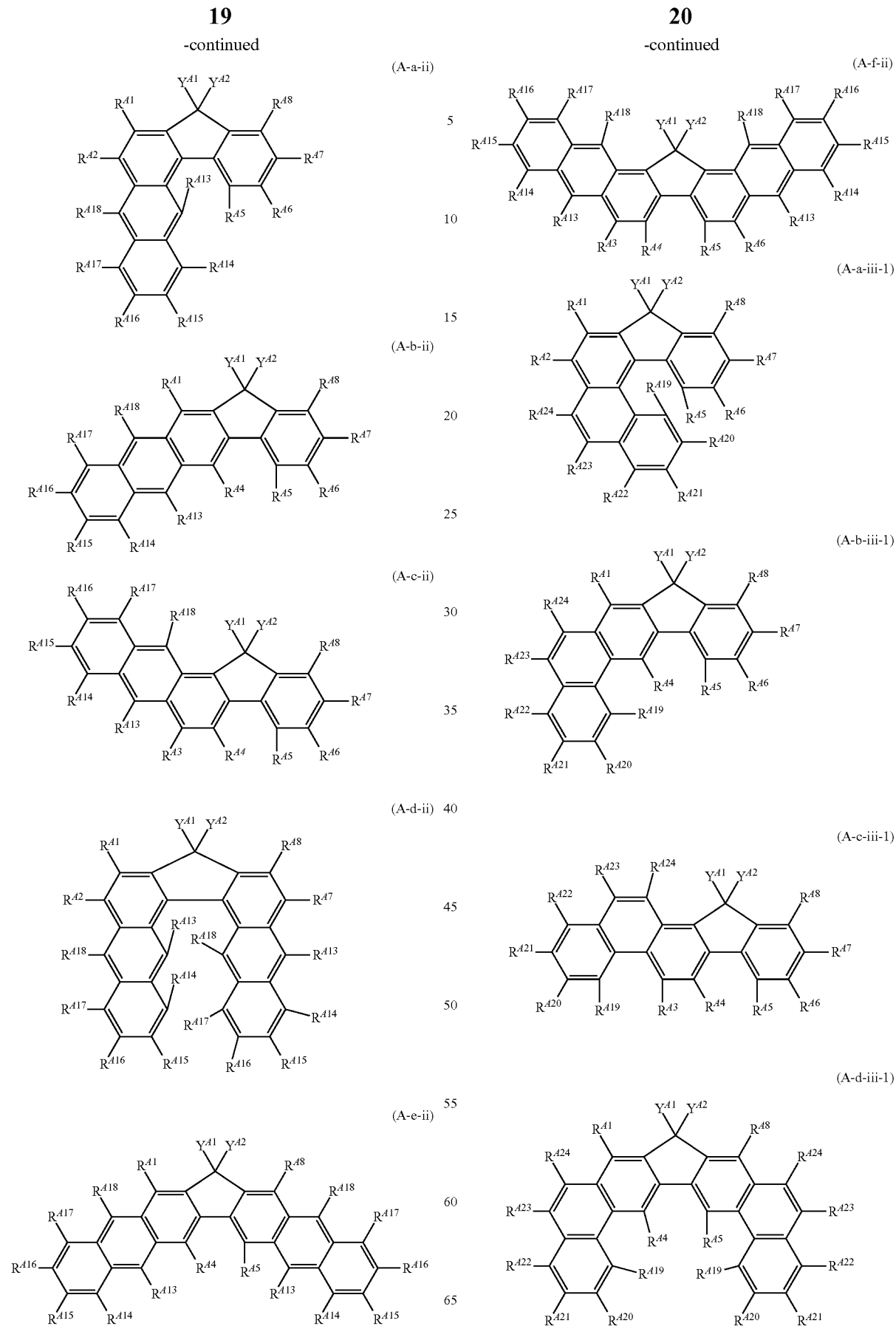

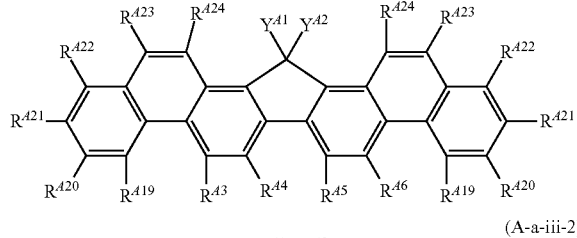
(A-e-iii-1)

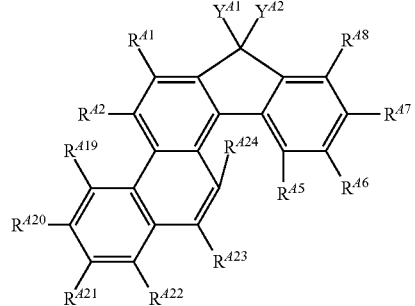
(A-a-iii-2)

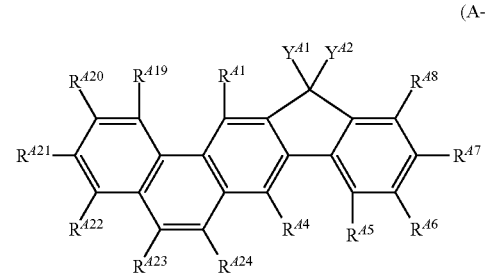
(A-b-iii-2)

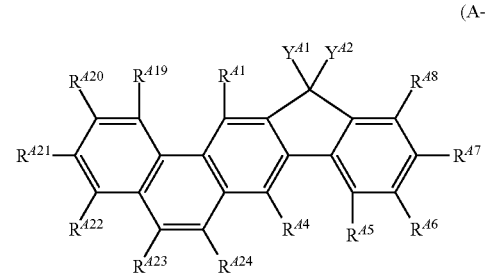
(A-c-iii-2)

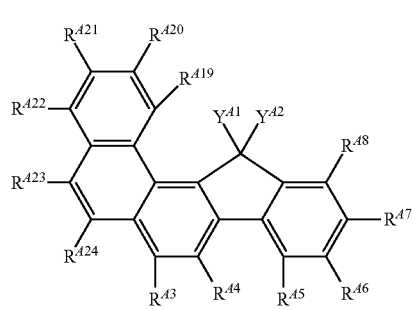
(A-d-iii-2)

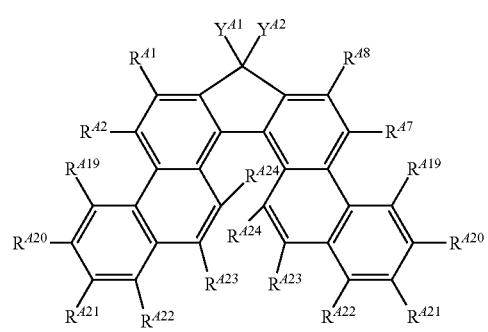
(A-e-iii-2)

(A-f-iii-2)

In a compound of one embodiment of the present invention, it is also preferred that the oxygen-containing, sulfur-containing or selenium-containing heteroaromatic condensed hydrocarbon group represented by $Ar^3$ in the general formula (1) is represented by the following general formula (B). Incidentally, needless to say the group represented by the general formula (B) contains a 5-membered ring in the condensed ring:

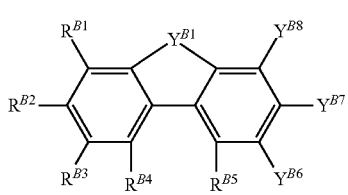
(B)

wherein in the general formula (B), $Y^{B1}$ is an oxygen atom, a sulfur atom or a selenium atom; and $R^{B1}$ to $R^{B8}$ are each independently a hydrogen atom or a substituent, provided that at least one combination selected from $R^{B1}$ and $R^{B2}$, $R^{B2}$ and $R^{B3}$, $R^{B3}$ and $R^{B4}$, $R^{B5}$ and $R^{B6}$, $R^{B6}$ and $R^{B7}$, and $R^{B7}$ and $R^{B8}$ binds to form any of the rings represented by the following general formulae (B-i) to (B-iii):

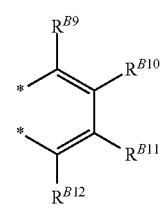
(B-i)

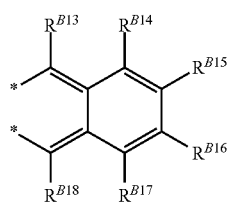 (B-ii)

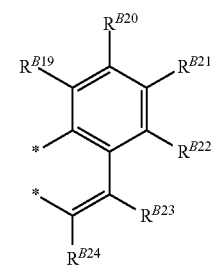 (B-iii)

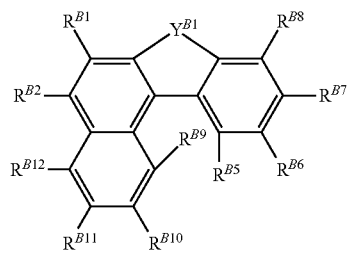 (B-a-i)

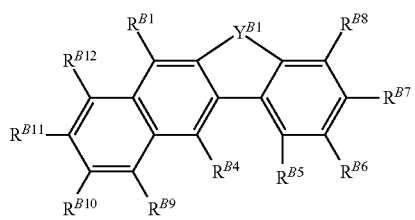 (B-b-i)

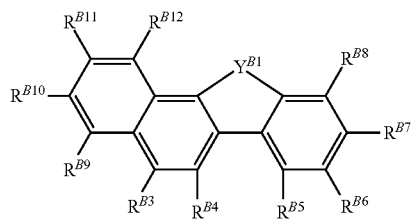 (B-c-i)

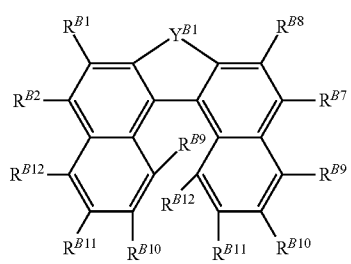 (B-d-i)

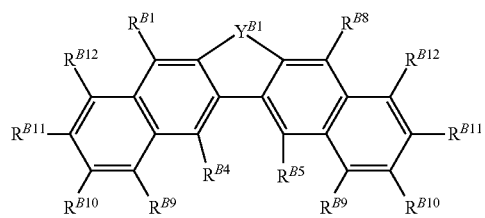 (B-e-i)

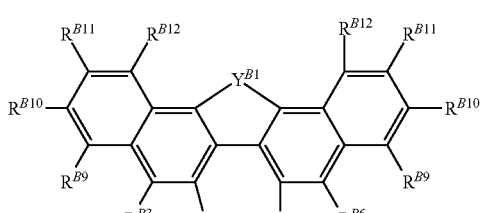 (B-f-i)

wherein in the general formulae (B-i) to (B-iii), * represent a bonding site to a carbon atom; and $R^{B9}$ to $R^{B24}$ are each independently a hydrogen atom or a substituent;

provided that at least one of $R^{B1}$ to $R^{B8}$ in the general formula (B) and $R^{B9}$ to $R^{B24}$ in the general formulae (B-i) to (B-iii) represents a direct bond to L mentioned above.

$Y^{B1}$ is preferably an oxygen atom or a sulfur atom.

As the substituents represented by $R^{B1}$ to $R^{B8}$ and $R^{B9}$ to $R^{B24}$, the same examples are exemplified as for the substituent represented by $L^1$, and in addition, an aryl group having 6 to 50 (preferably 6 to 25, more preferably 6 to 18) ring carbon atoms and a heteroaryl group having 5 to 50 (preferably 5 to 24, more preferably 5 to 13) ring atoms are also mentioned as a preferred substituent.

Here, in cases where the substituent represented by $R^{B1}$ to $R^{B8}$ or $R^{B9}$ to $R^{B24}$ is a heteroaryl group, any of an oxygen-containing heteroaryl group, a sulfur-containing heteroaryl group and a selenium-containing heteroaryl group is preferred, and among them, a heteroaryl group containing no nitrogen atom is more preferred.

It is also preferred that all of $R^{B1}$ to $R^{B8}$ and $R^{B9}$ to $R^{B24}$ are a hydrogen atom (provided that at least one of $R^{B1}$ to $R^{B8}$ in the general formula (B) and $R^{B9}$ to $R^{B24}$ in the general formulae (B-i) to (B-iii) represents a direct bond to $L^1$ mentioned above).

In the general formula (B), $R^{B6}$ preferably represents a direct bond to $L^1$ mentioned above.

In cases where at least one combination selected from $R^{B1}$ and $R^{B2}$, $R^{B2}$ and $R^{B3}$, $R^{B3}$ and $R^{B4}$, $R^{B5}$ and $R^{B6}$, $R^{B6}$ and $R^{B7}$, and $R^{B7}$ and $R^{B8}$ binds to form any of the rings represented by the general formulae (B-i) to (B-iii), the heteroaromatic condensed hydrocarbon group represented by $Ar^3$ is specifically represented by any one of the following general formulae (B-a-i) to (B-f-iii-2). [The definitions of the groups in each formula are the same as in the general formulae (B) and (B-i) to (B-iii), and the preferred examples are also the same. Incidentally, the same signs and numerals in a formula, if present, may be the same or different.]

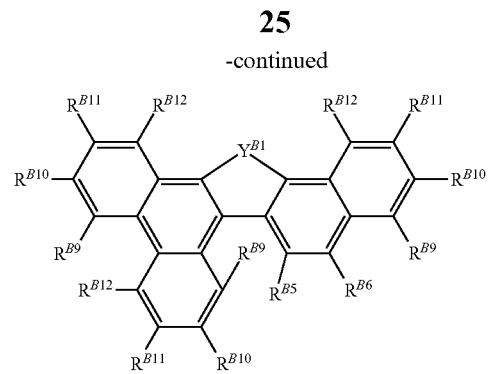
(B-g-i)
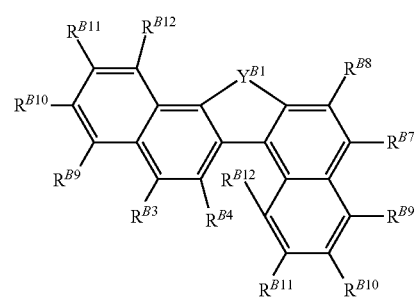
(B-h-i)
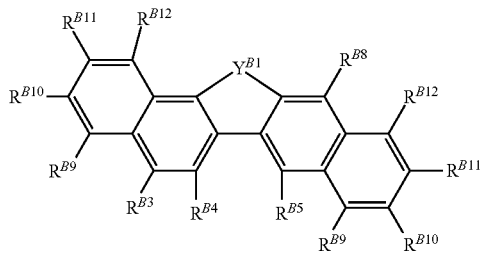
(B-i-i)
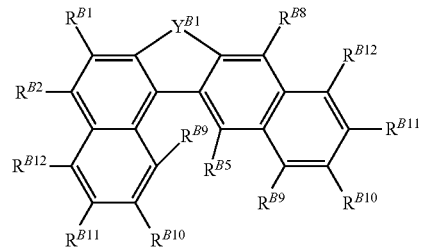
(B-j-i)
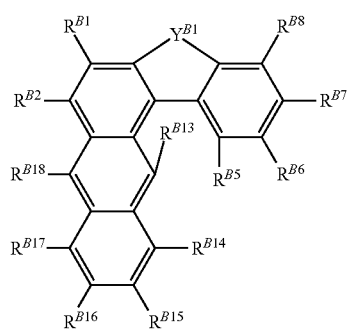
(B-a-ii)
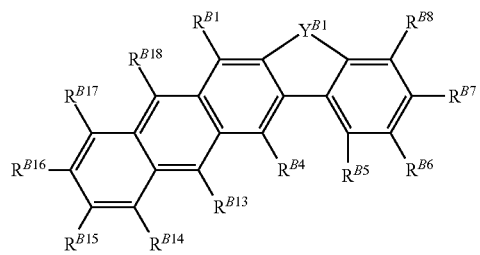
(B-b-ii)
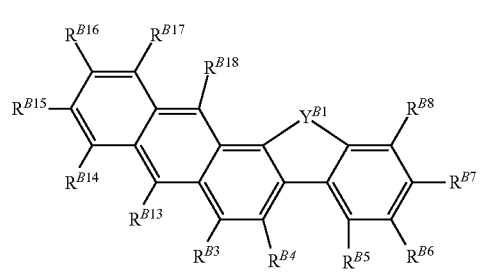
(B-c-ii)
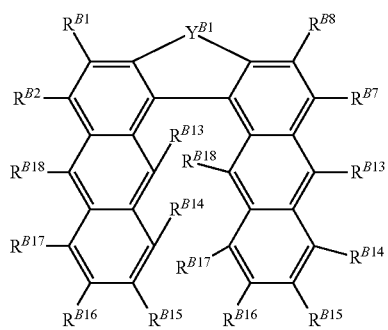
(B-d-ii)
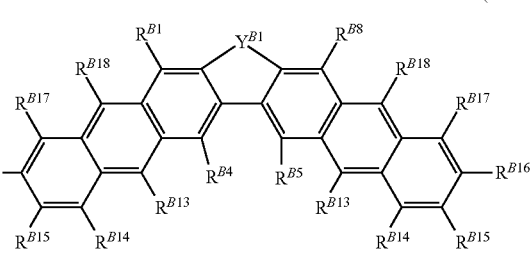
(B-e-ii)
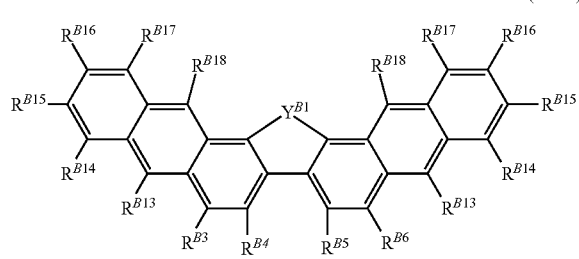
(B-f-ii)

(B-a-iii-1)
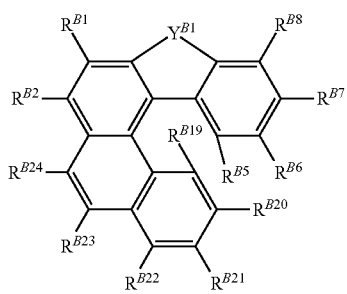
(B-a-iii-2)
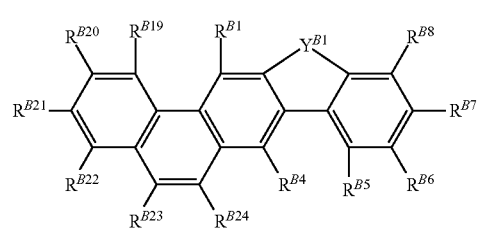
(B-b-iii-1)
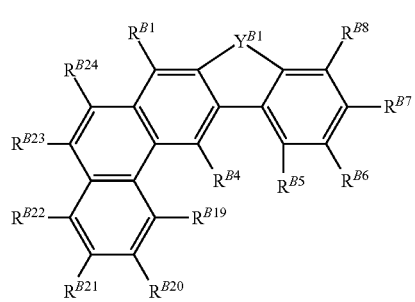
(B-b-iii-2)
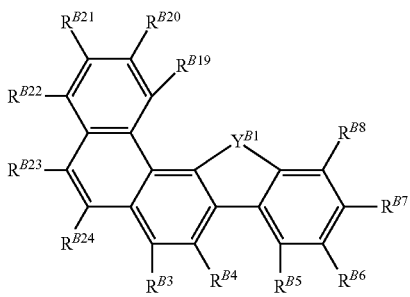
(B-c-iii-1)
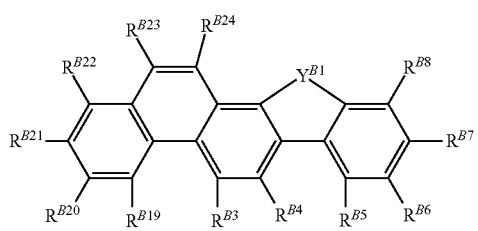
(B-c-iii-2)
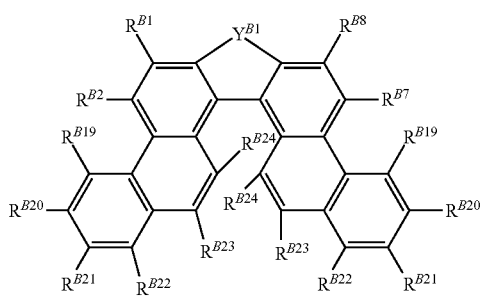
(B-d-iii-1)
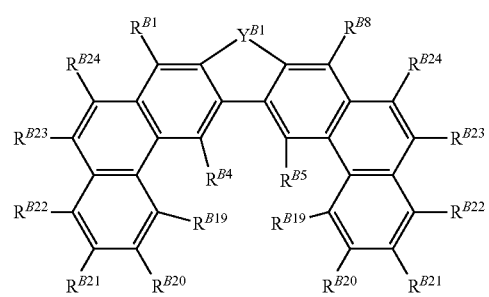
(B-d-iii-2)
(B-e-iii-1)
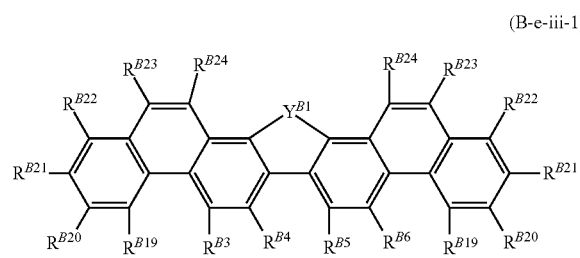
(B-e-iii-2)
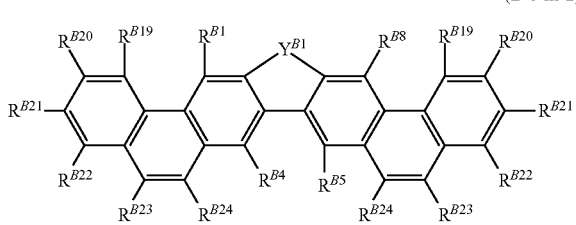

(B-f-iii-2)

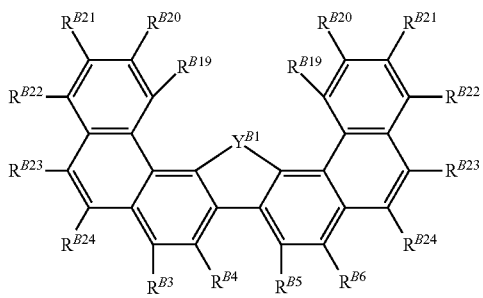

In a compound of one embodiment of the present invention, Ar³ is preferably a residue of any one selected from a substituted or unsubstituted naphthacene, a substituted or unsubstituted pyrene, a substituted or unsubstituted chrysene, a substituted or unsubstituted triphenylene, a substituted or unsubstituted benzotriphenylene, a substituted or unsubstituted benzanthracene, a substituted or unsubstituted dibenzanthracene, a substituted or unsubstituted benzophenanthrene, a substituted or unsubstituted benzofluorene, a substituted or unsubstituted fluoranthene, a substituted or unsubstituted benzofluoranthene, a substituted or unsubstituted benzochrysene, a substituted or unsubstituted naphthanthracene, a substituted or unsubstituted dibenzofluorene, a substituted or unsubstituted indenofluorene, a substituted or unsubstituted indenobenzofluorene, and a substituted or unsubstituted indenophenanthrene. The "residue" as used herein refers to a monovalent group after one hydrogen atom is eliminated in each of the above structures.

Specific examples of the compound of one embodiment of the present invention include the following compound, but are not especially limited thereto.

[Chem. 22]

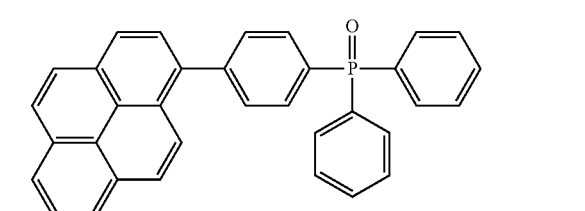

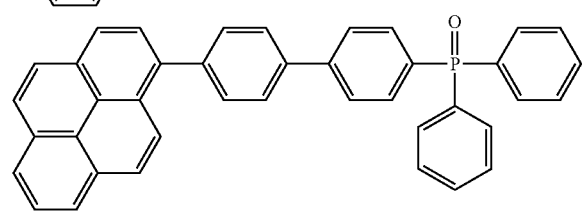

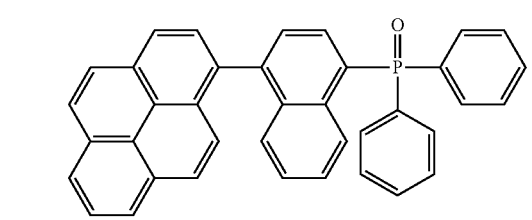

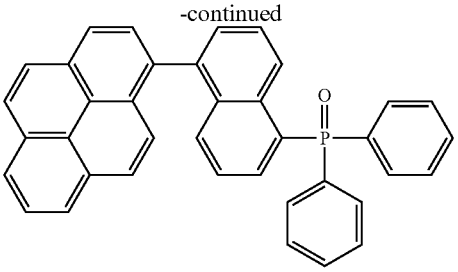

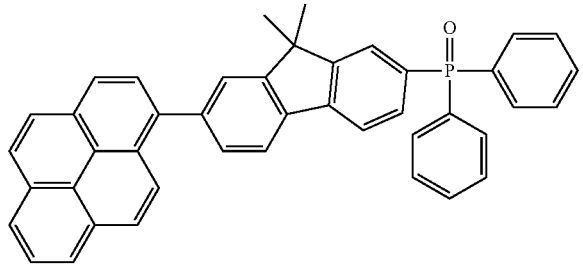

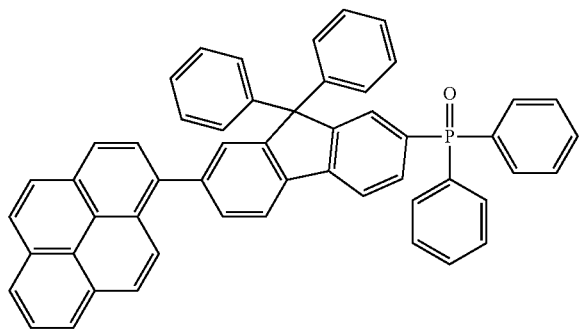

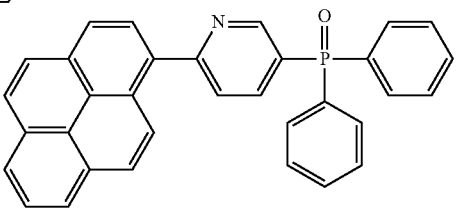

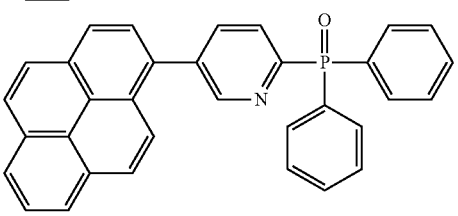

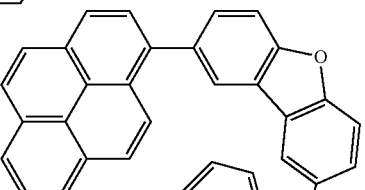

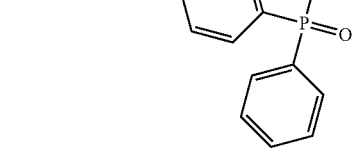

-continued
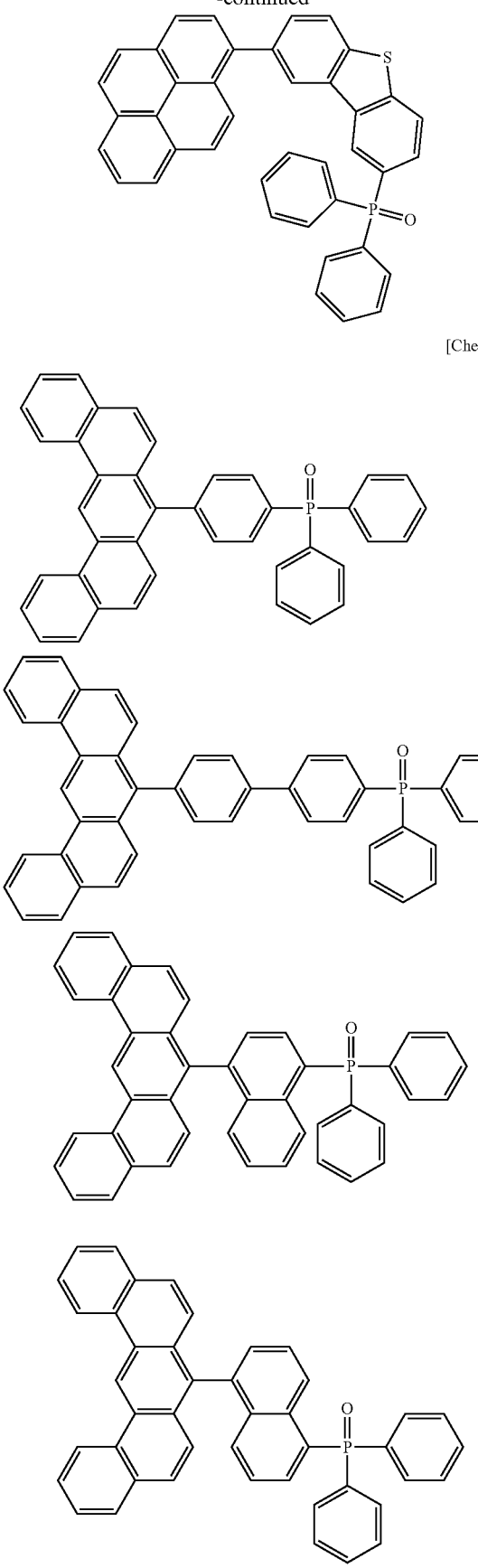
[Chem. 23]
-continued
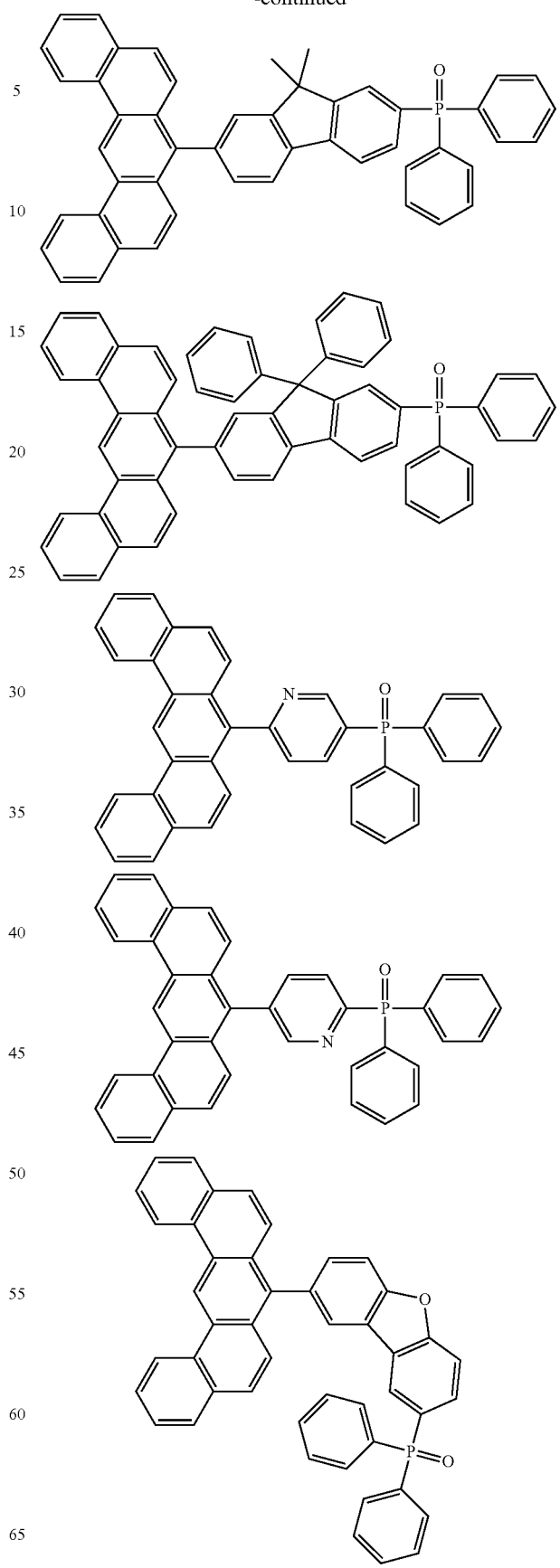

-continued
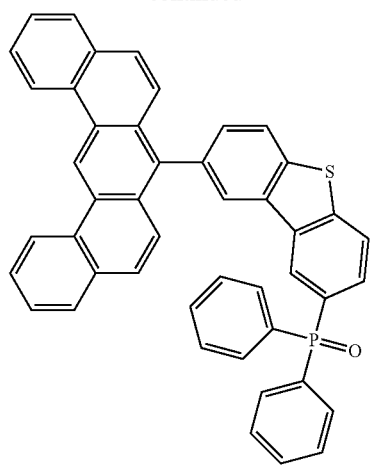
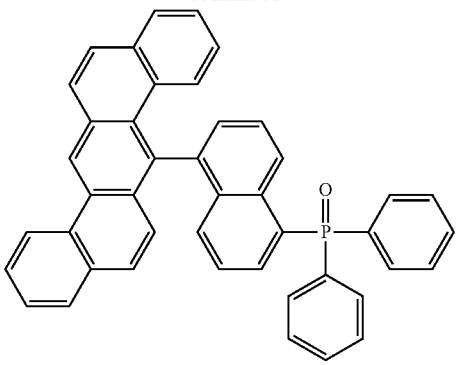
[Chem. 24]
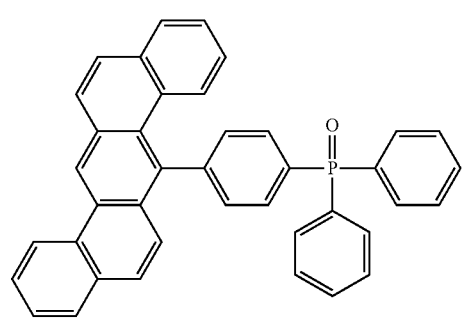
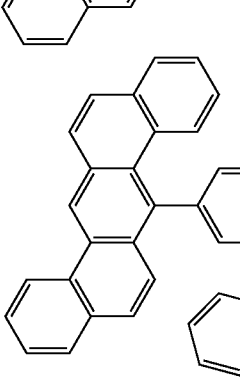
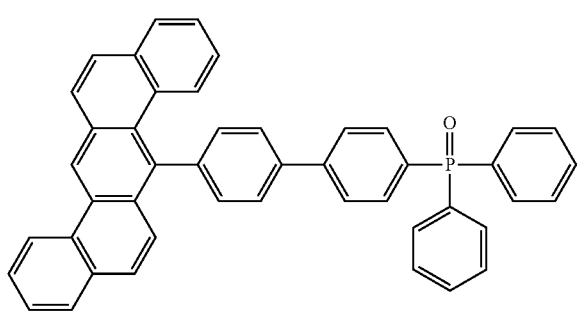
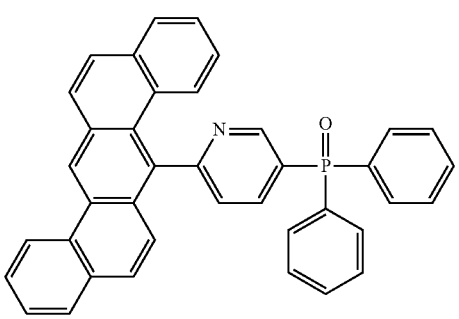
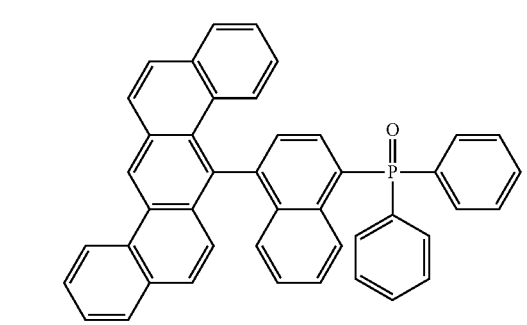
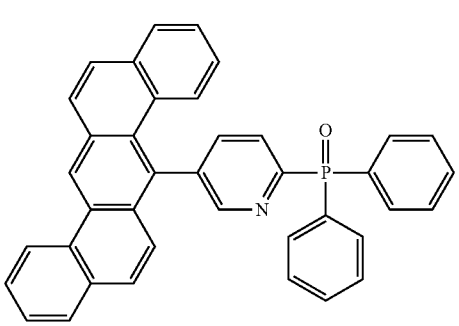

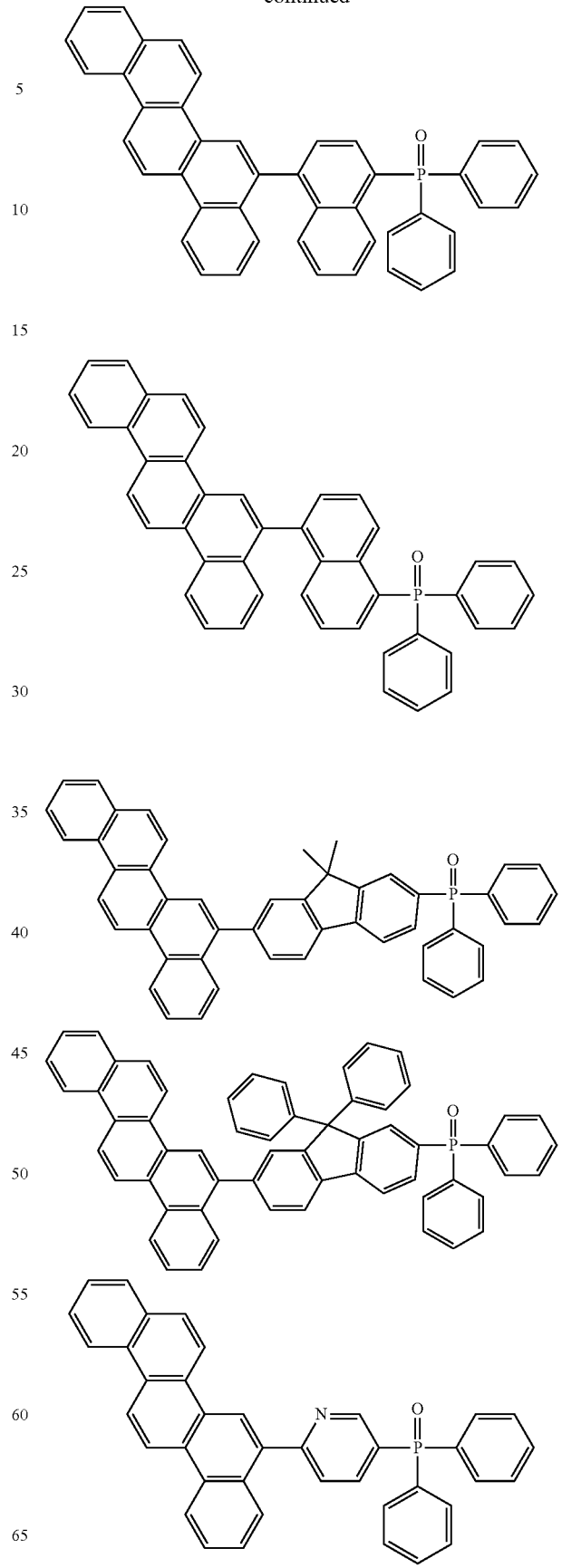

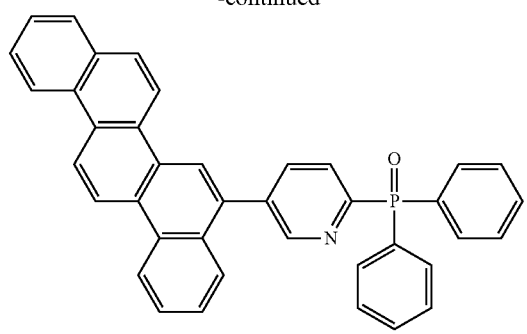
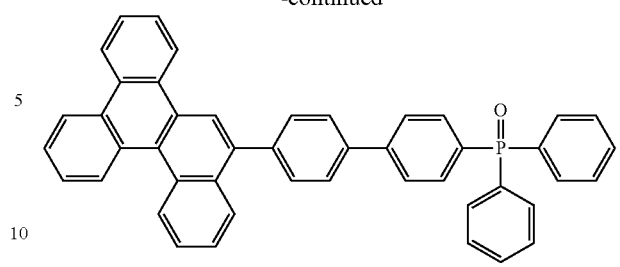
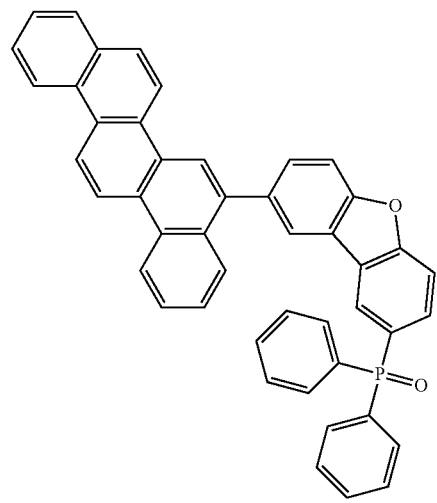
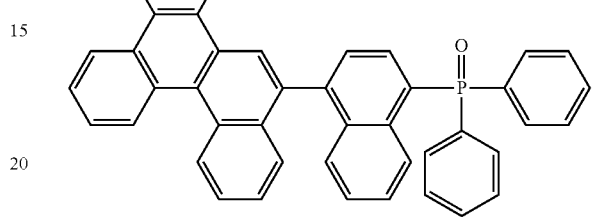
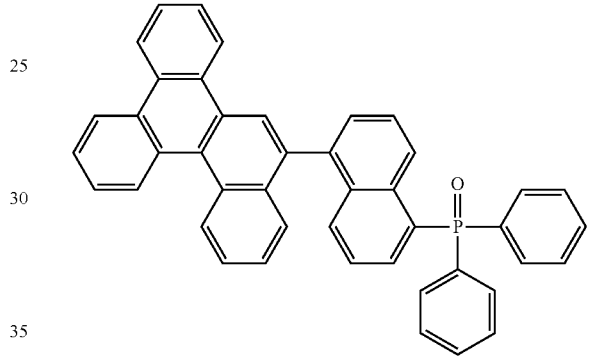
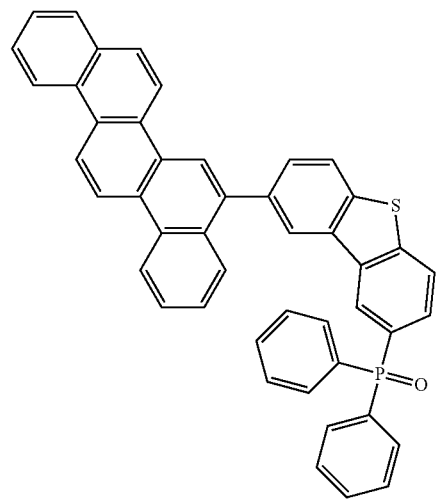
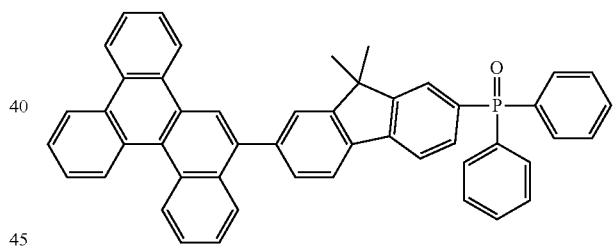
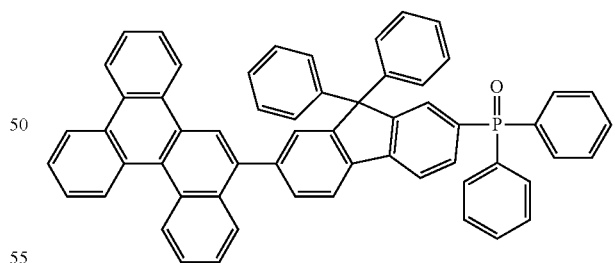
[Chem. 26]
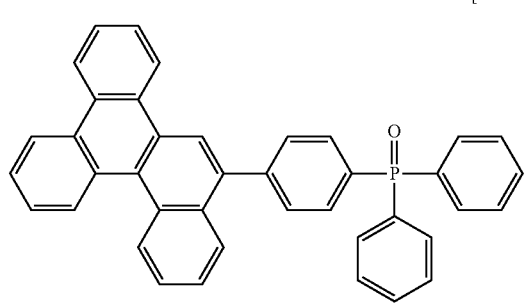
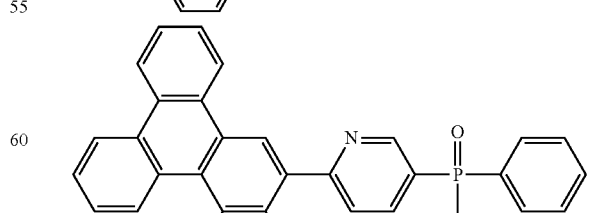
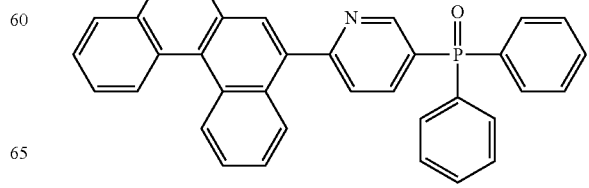

-continued
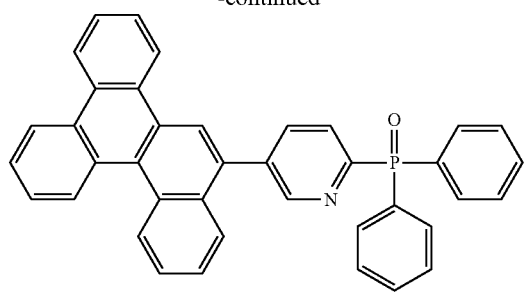
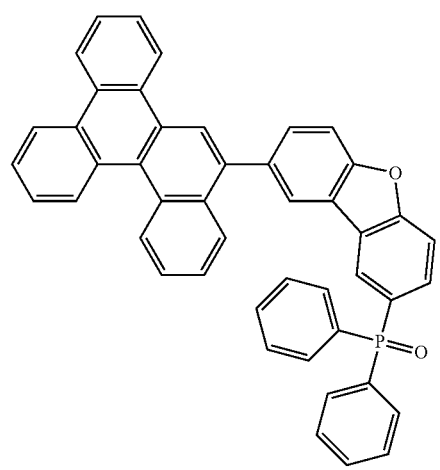
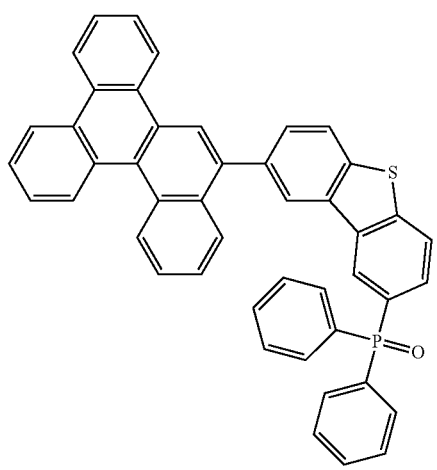
[Chem. 27]
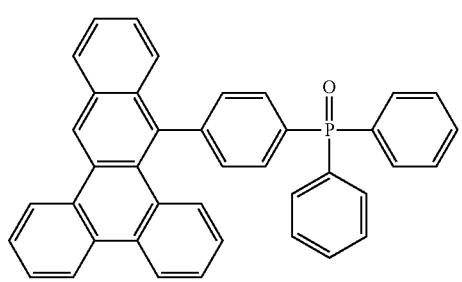
-continued
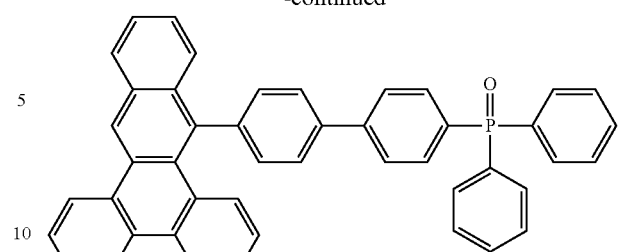
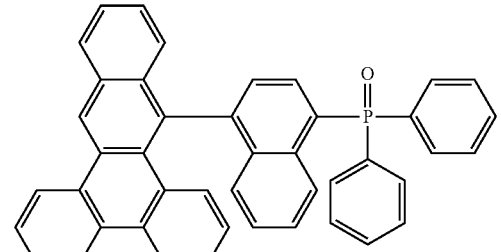
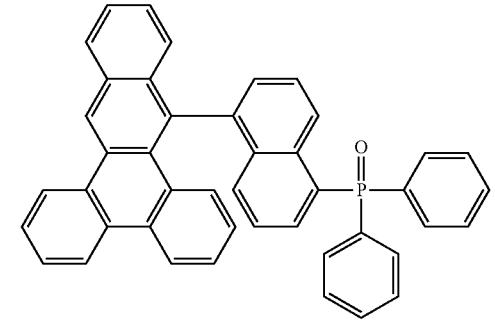
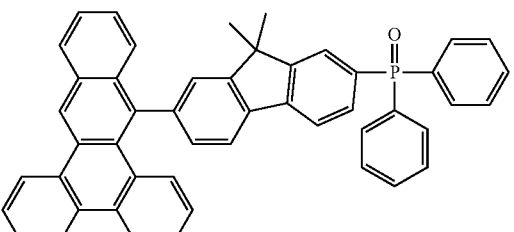
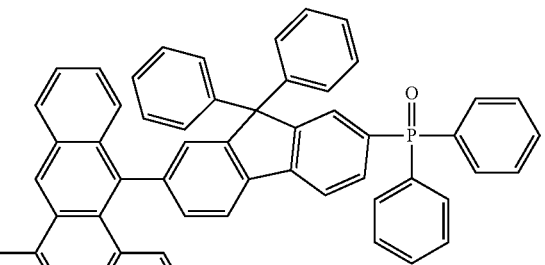
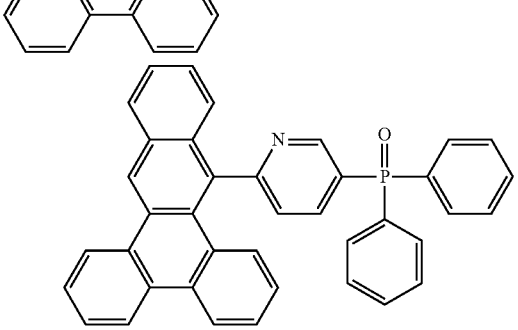

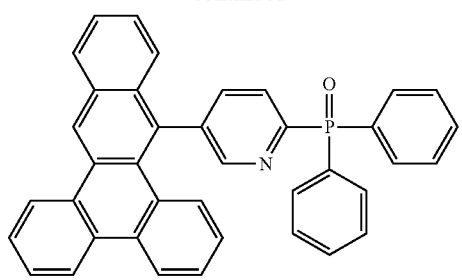
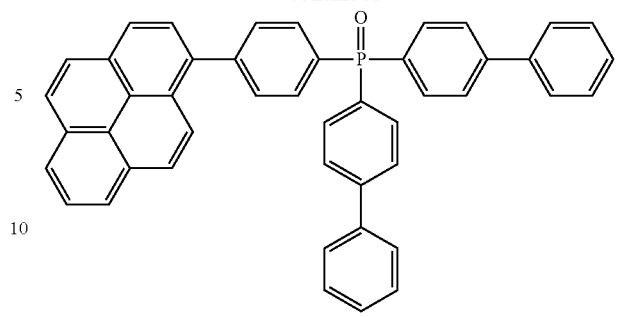
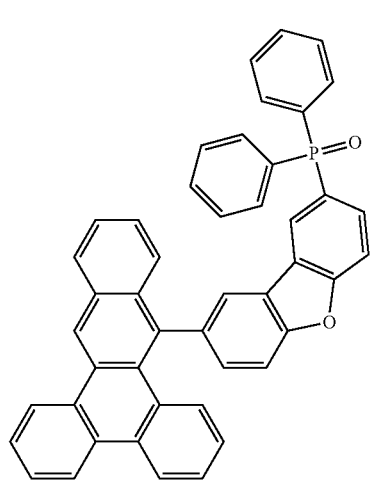
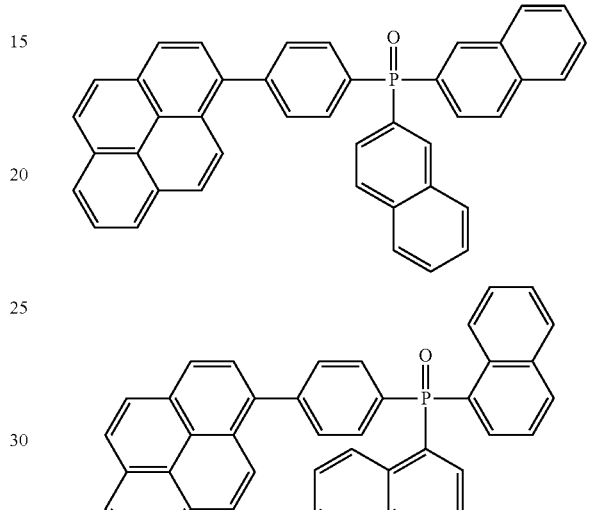
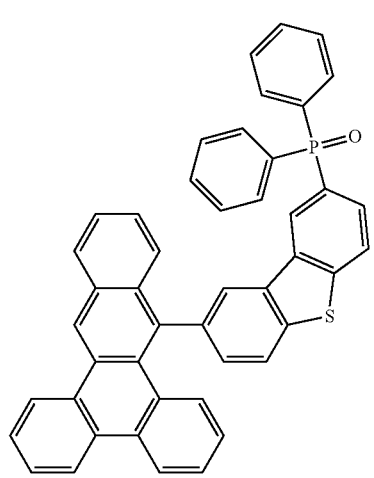
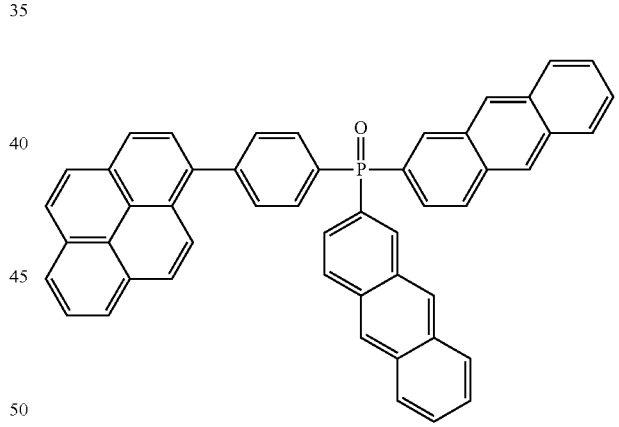
[Chem. 28]
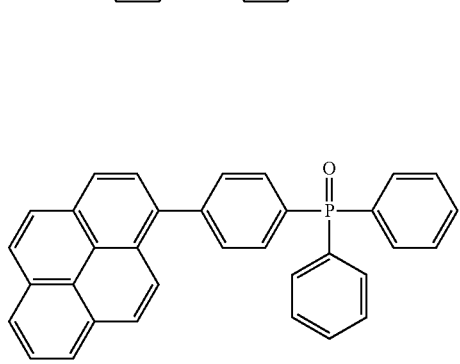
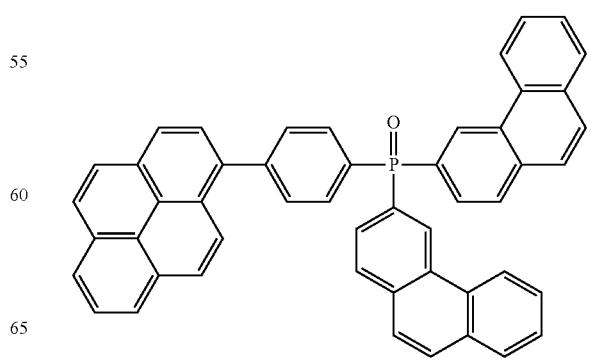

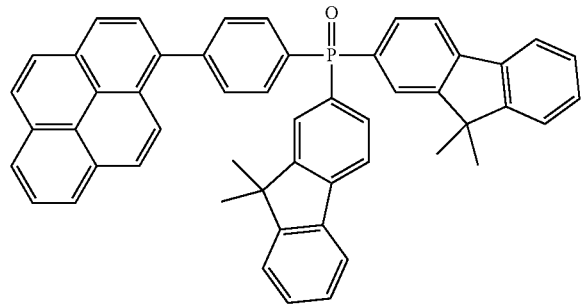
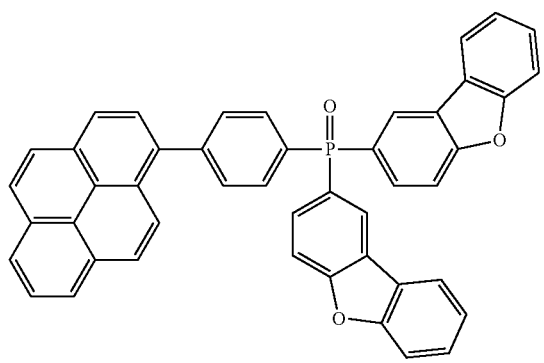
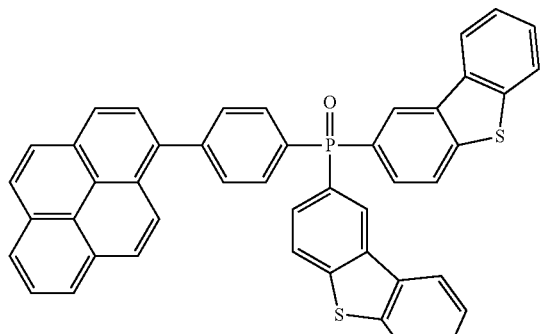
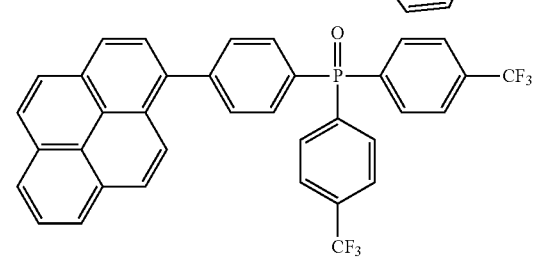
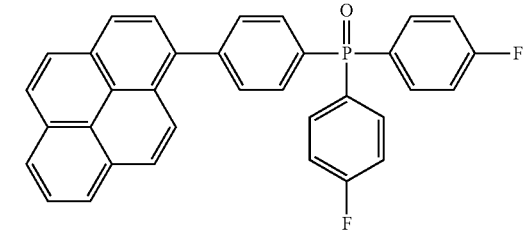
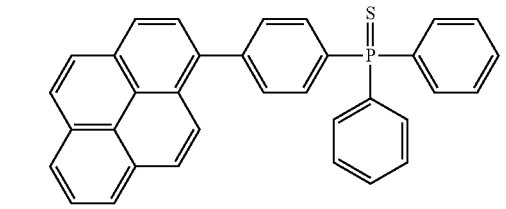
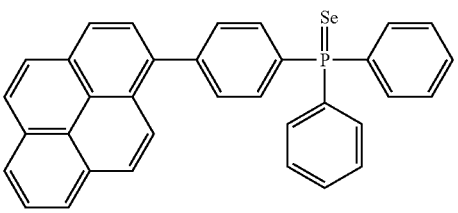
[Chem. 29]
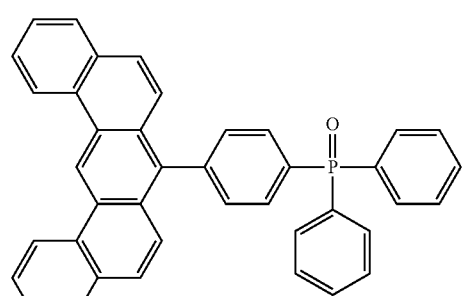
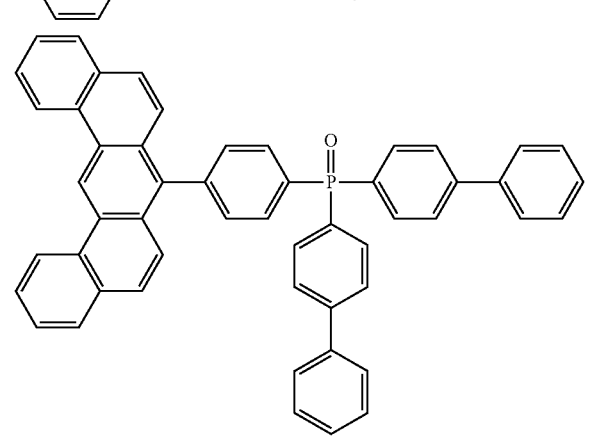
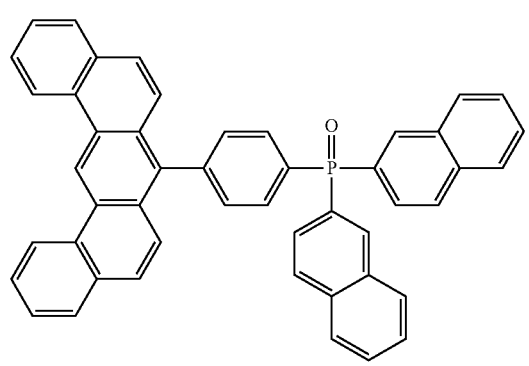
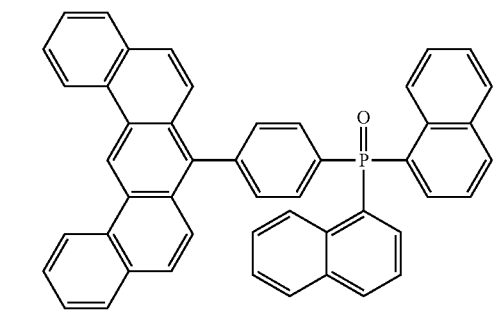

45
-continued
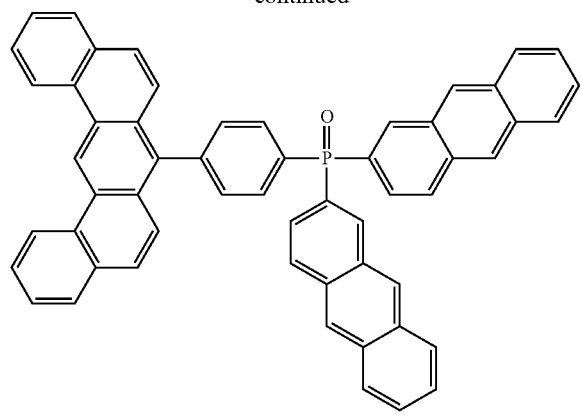
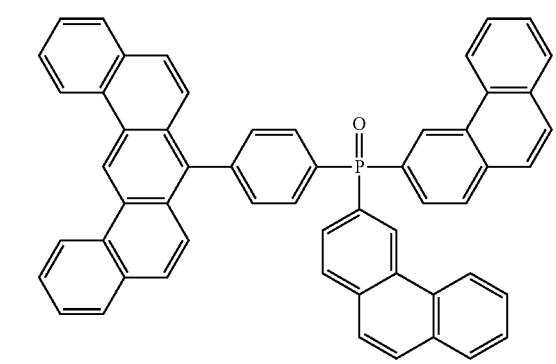
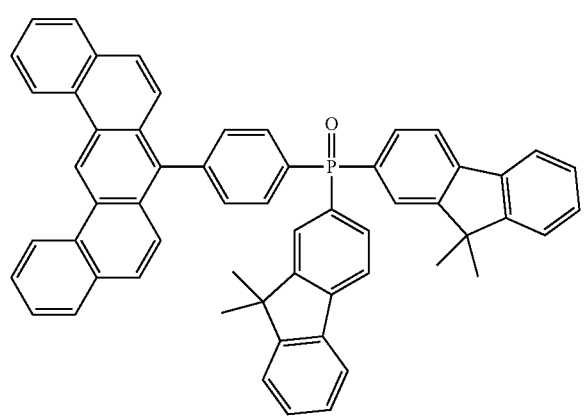
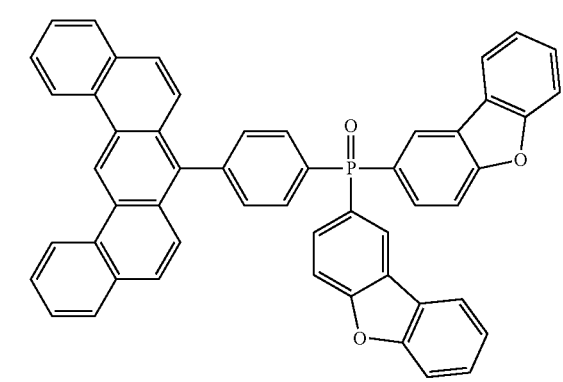
46
-continued
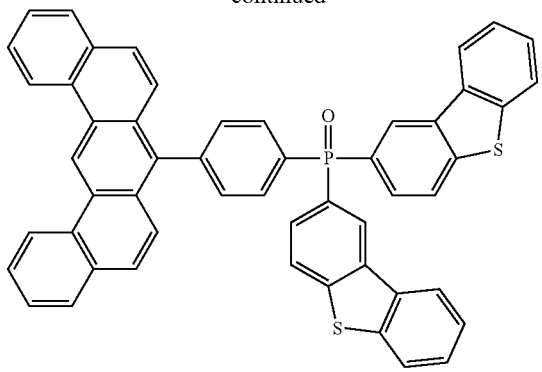
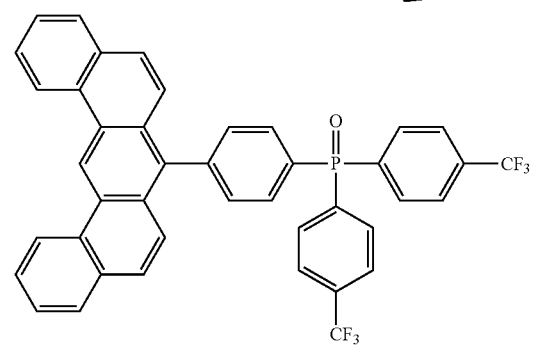
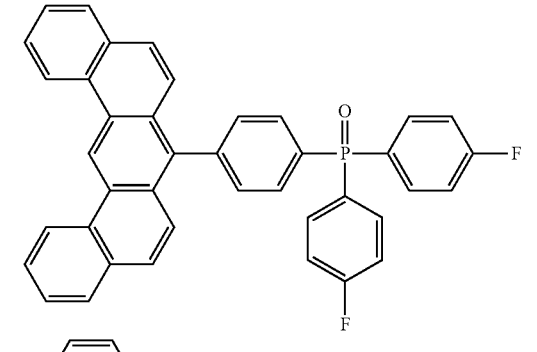
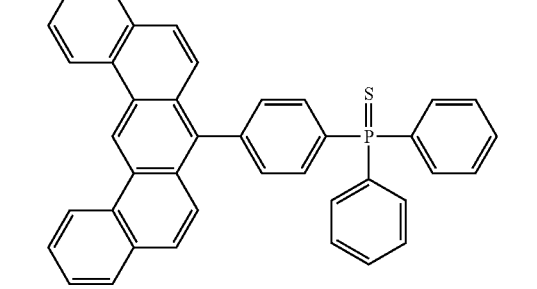
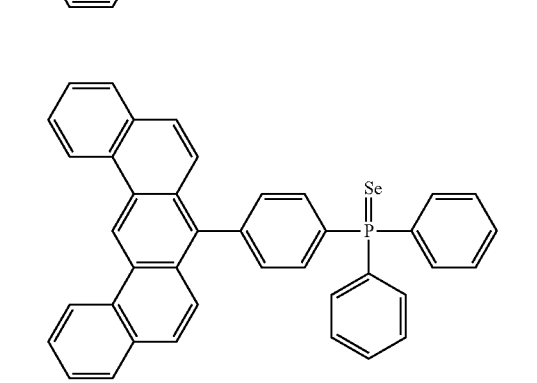

[Chem. 30]
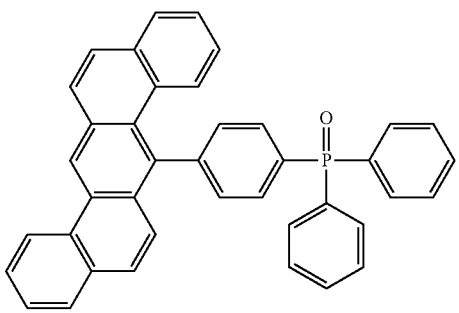
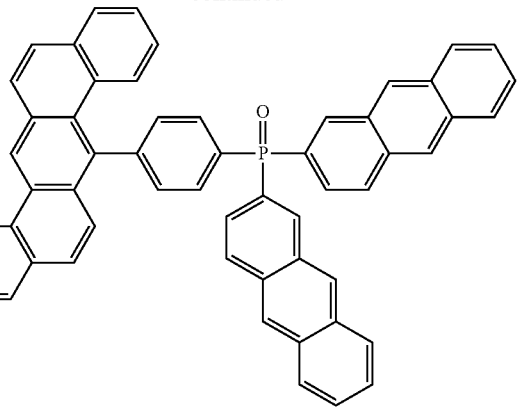
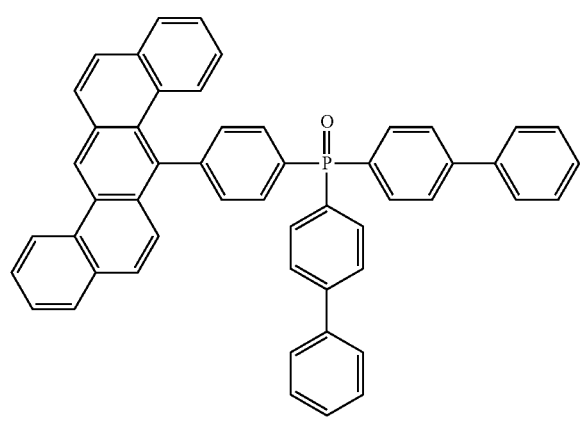
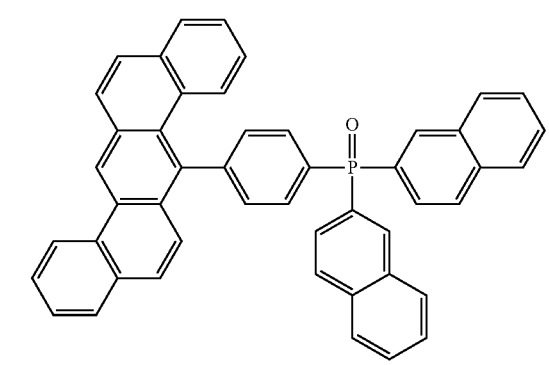
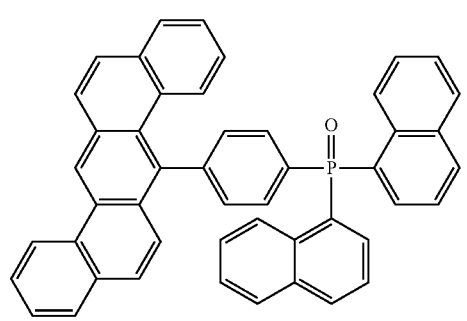
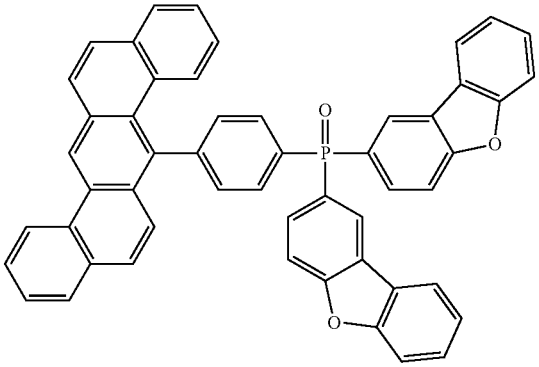

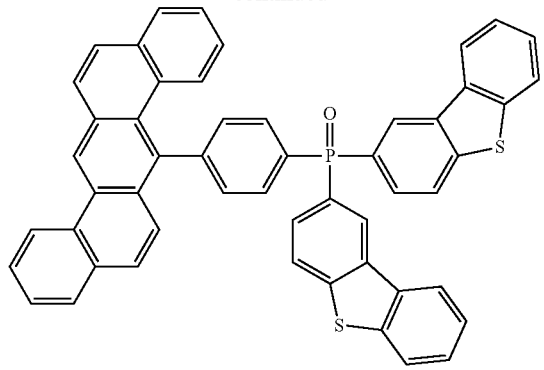
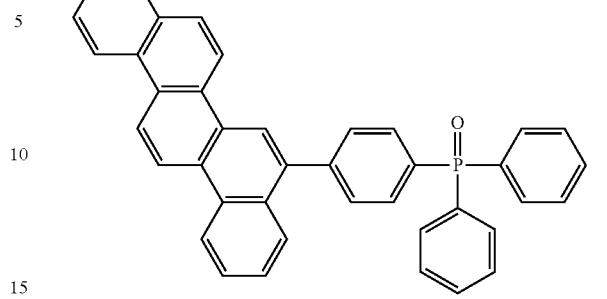
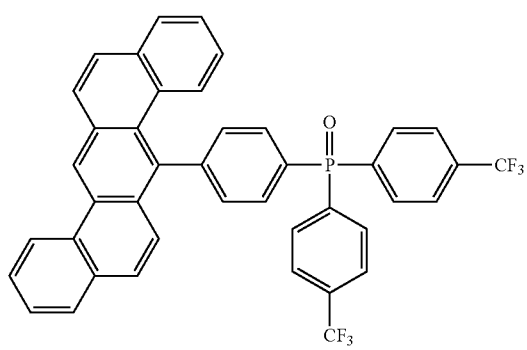
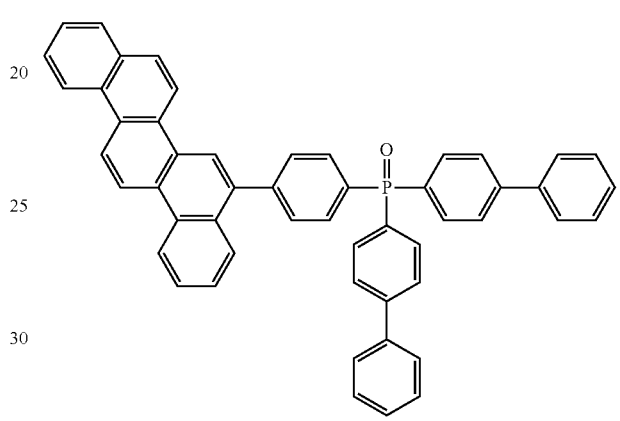
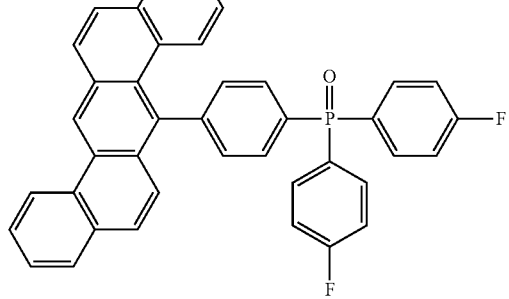
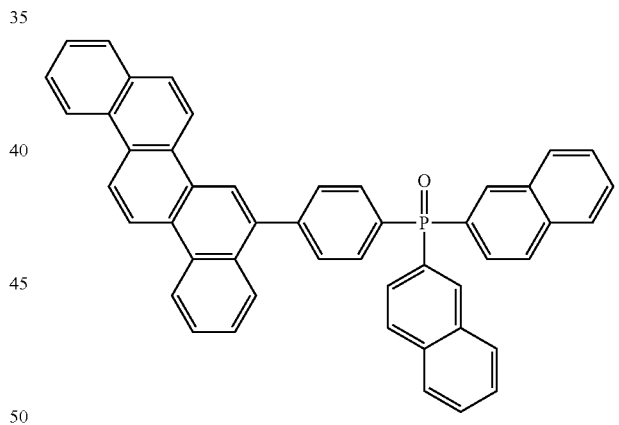
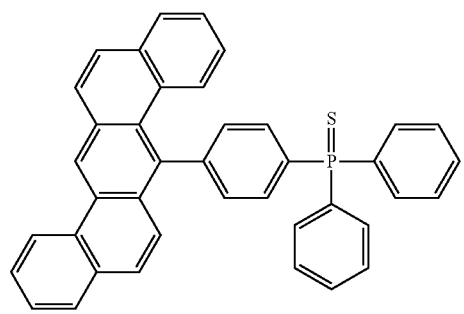
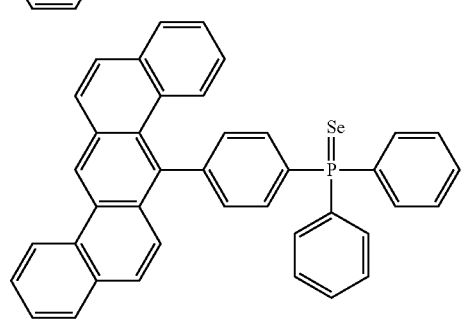

51
-continued
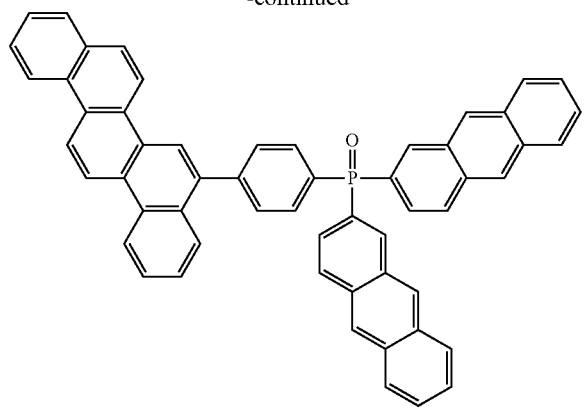
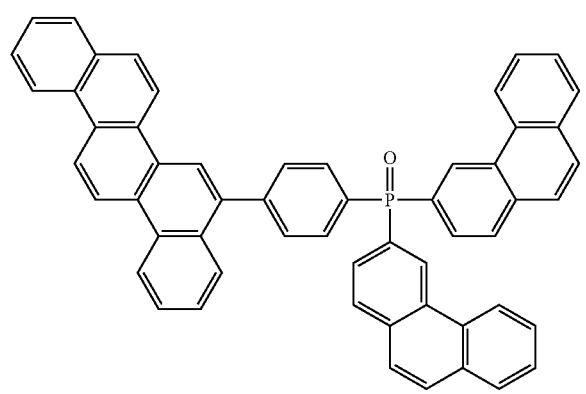
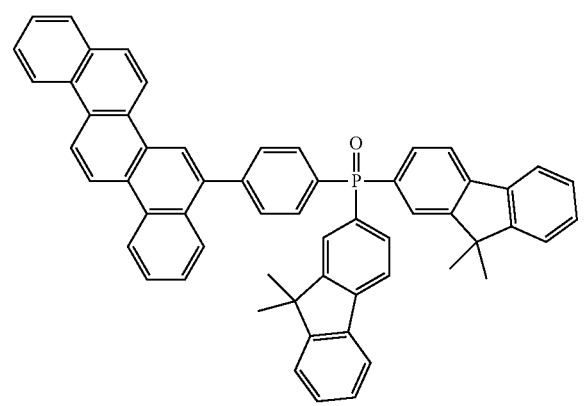
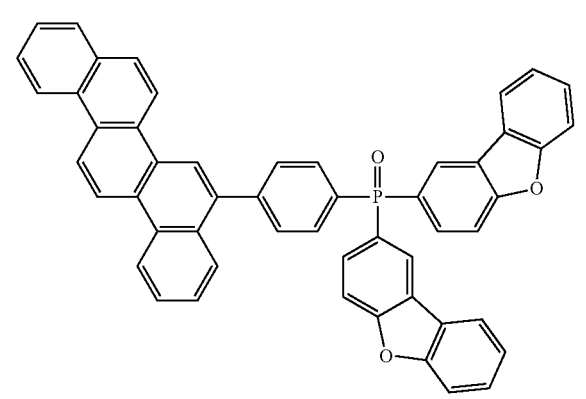
52
-continued
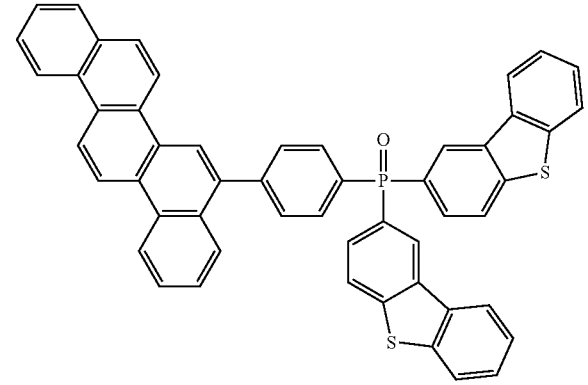
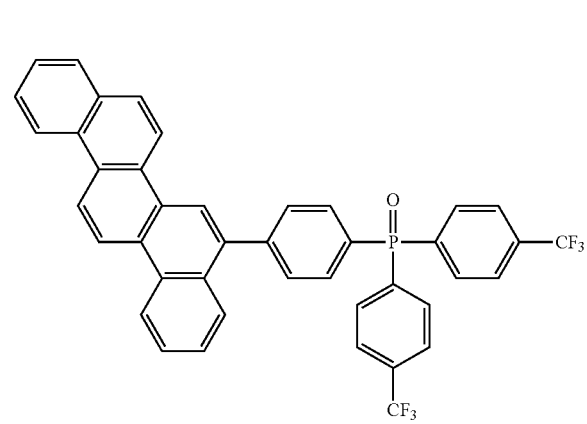
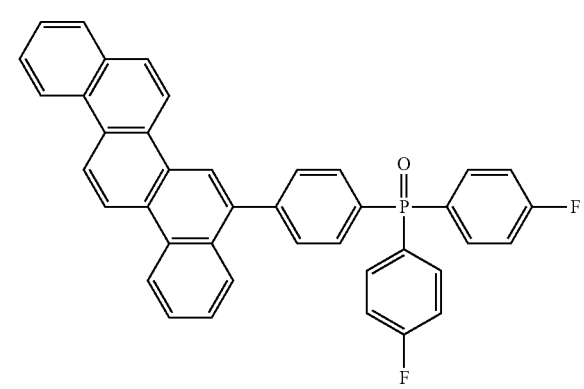
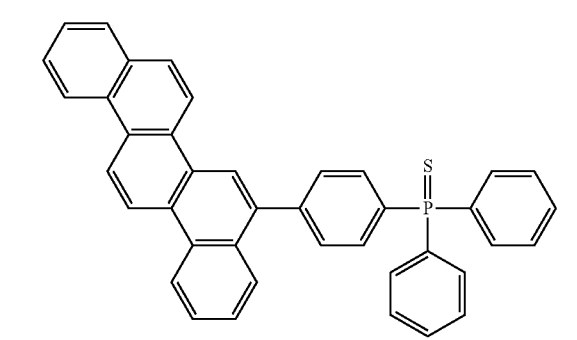

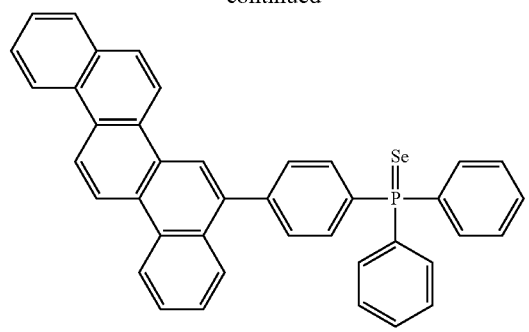
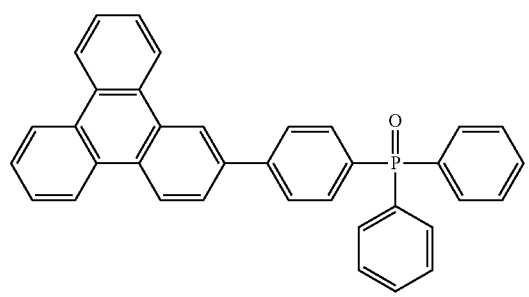
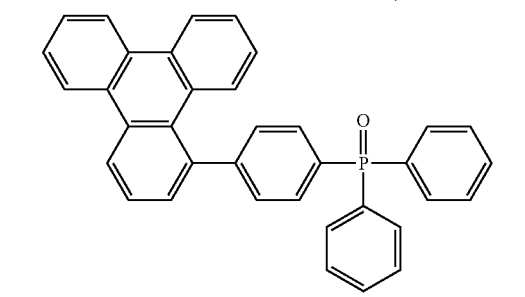
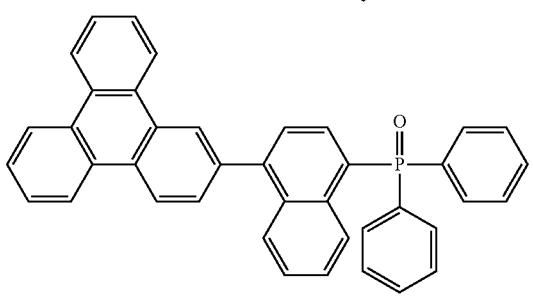
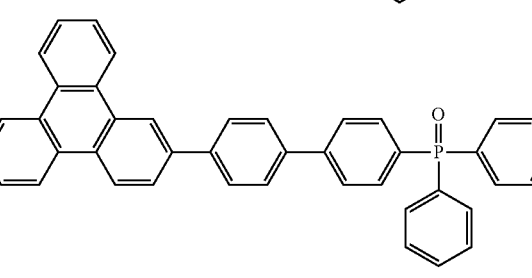
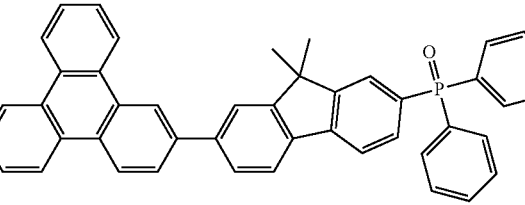
[Chem. 32]
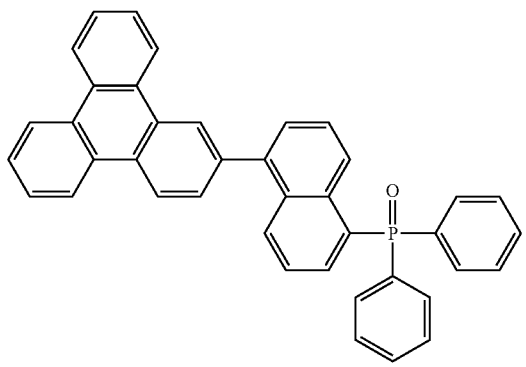
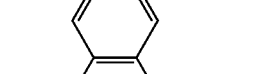
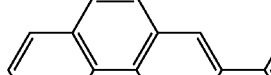
[Chem. 33]

55
-continued
56
-continued
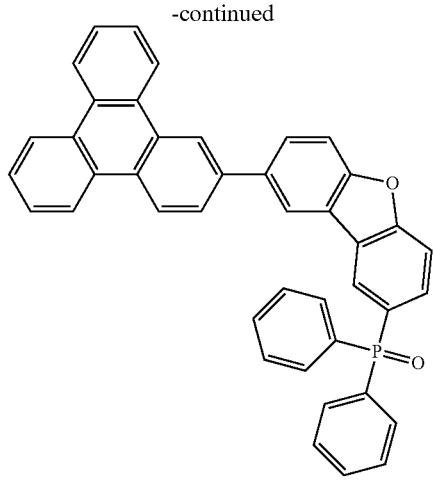
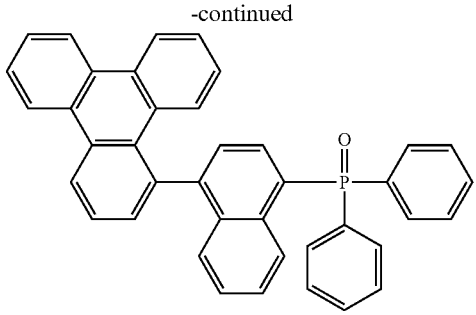
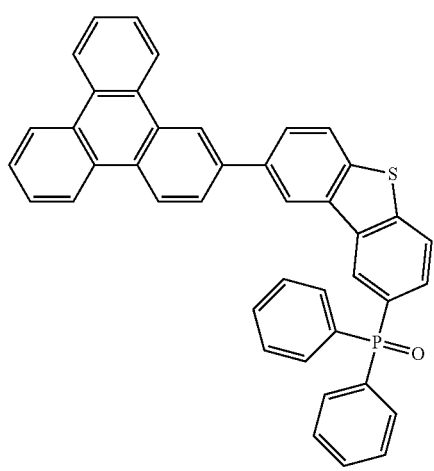
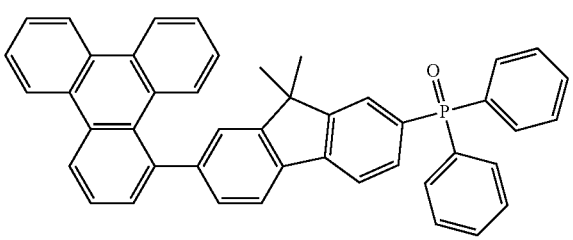
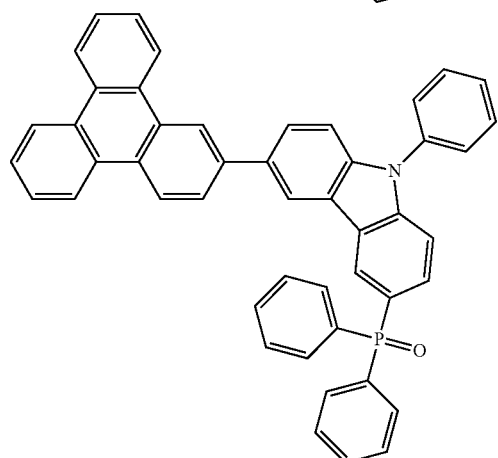
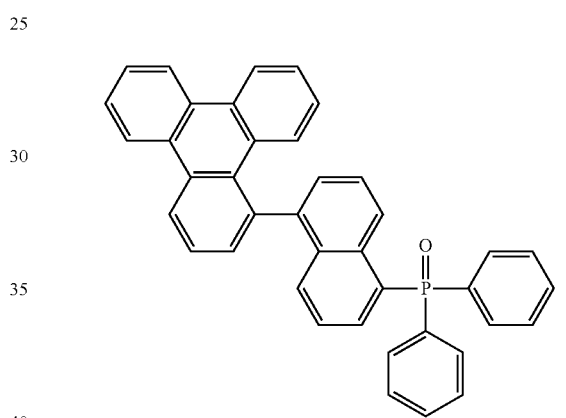
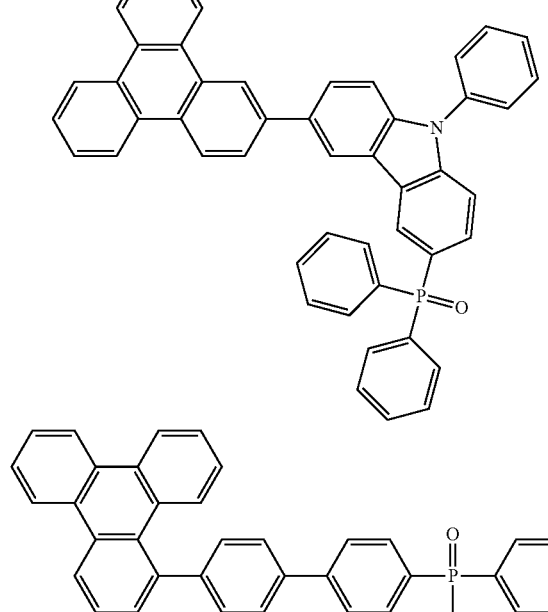
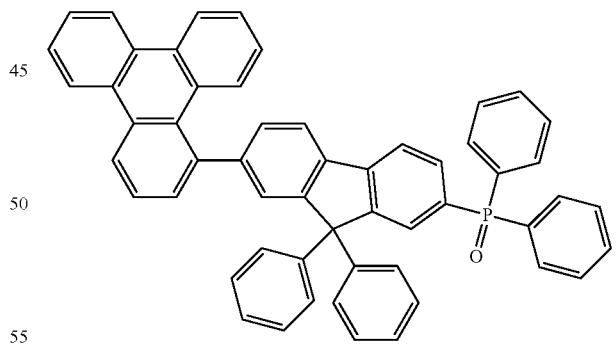
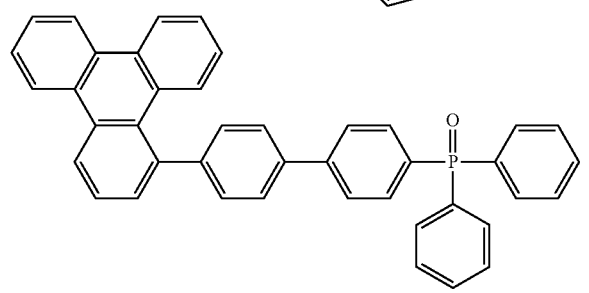
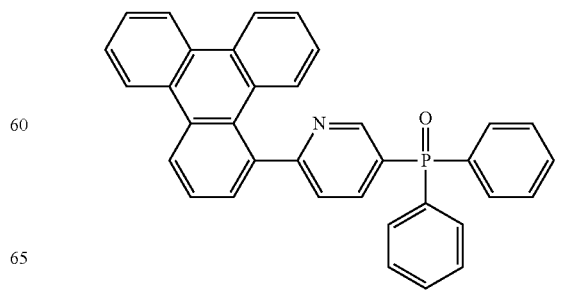

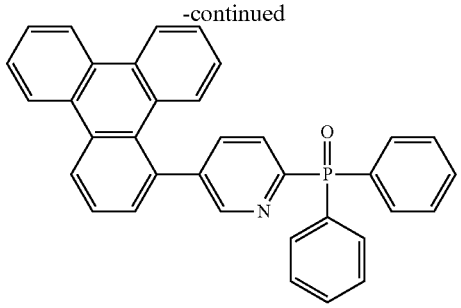
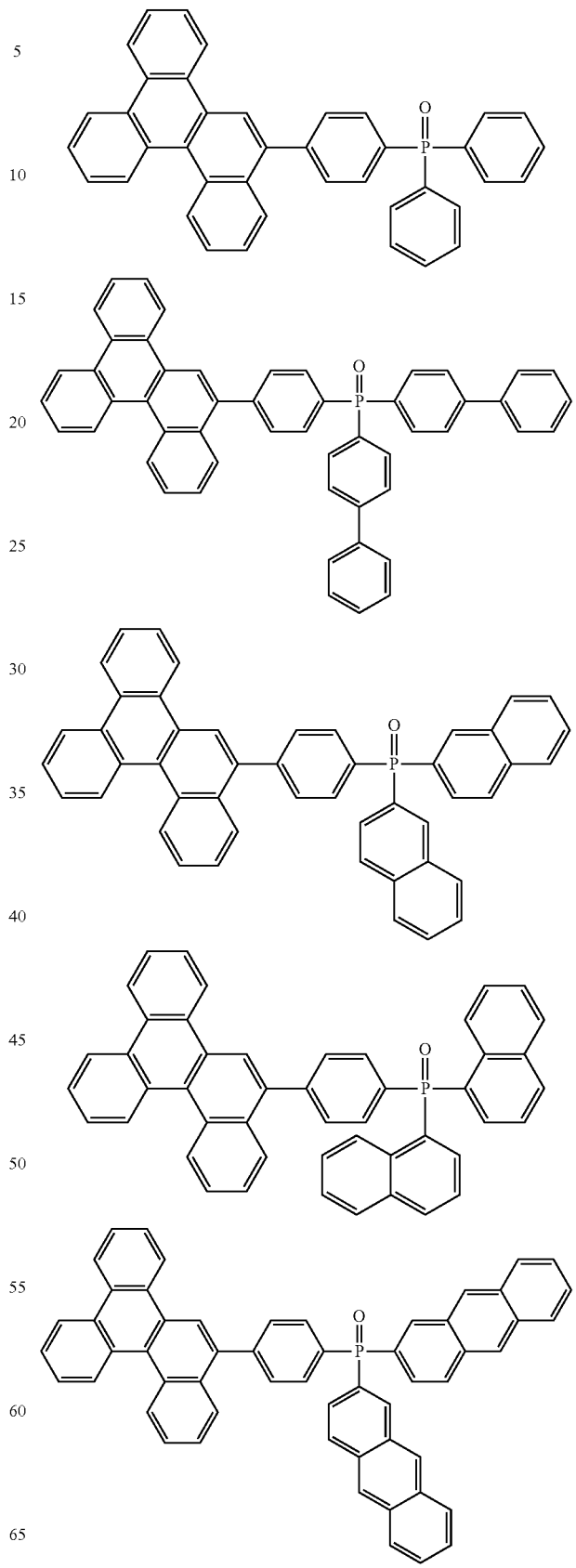

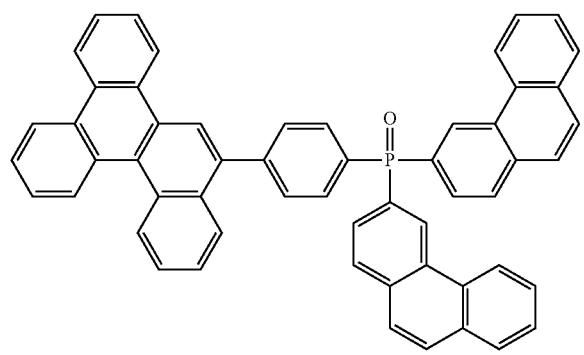
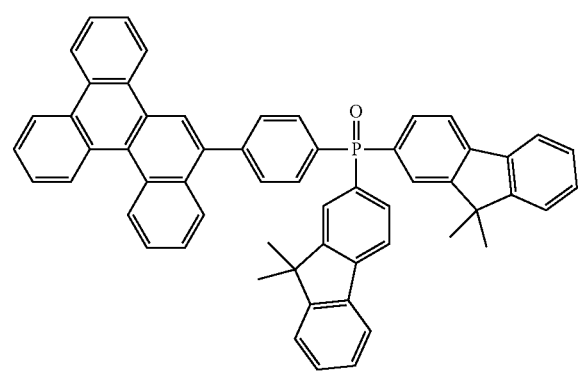
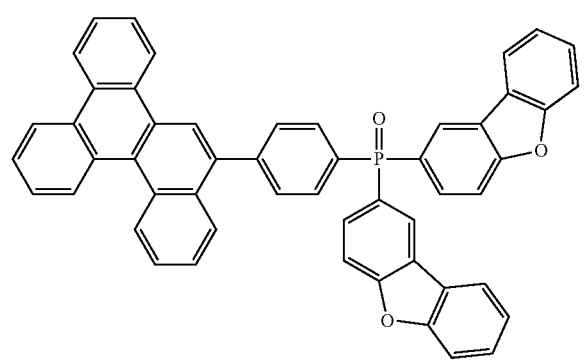
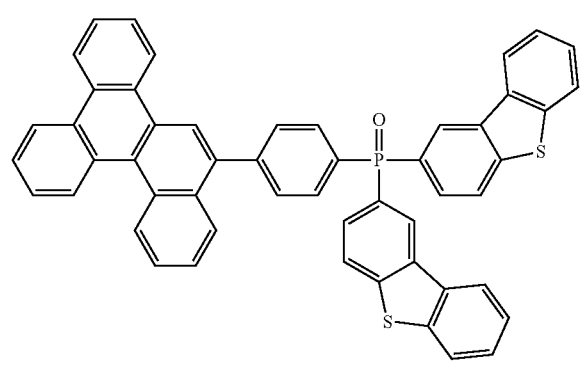
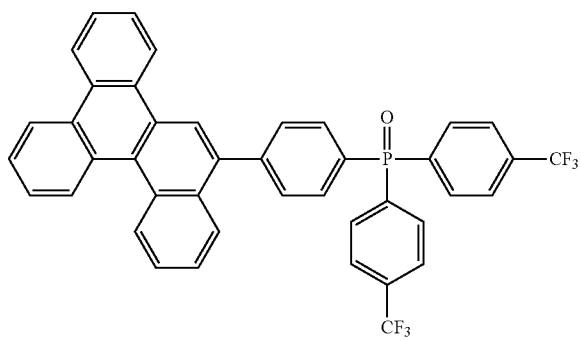
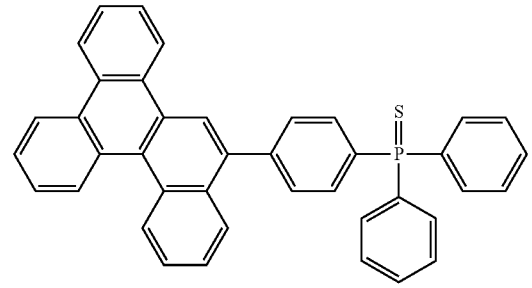
[Chem. 35]

61
-continued
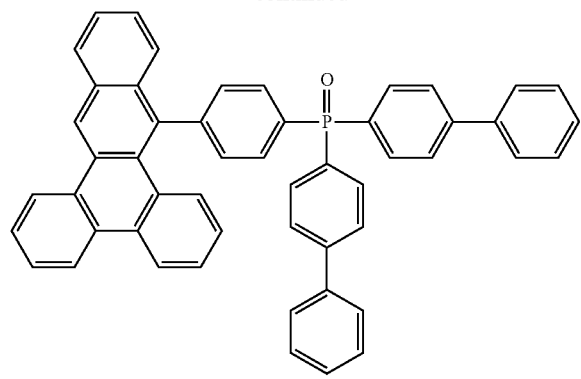
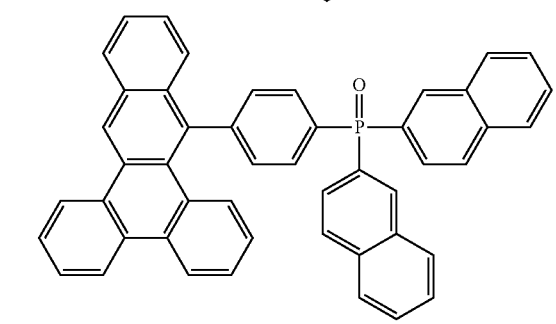
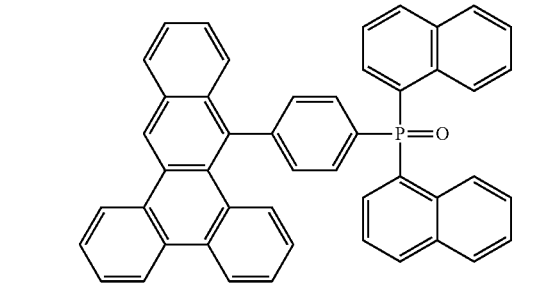
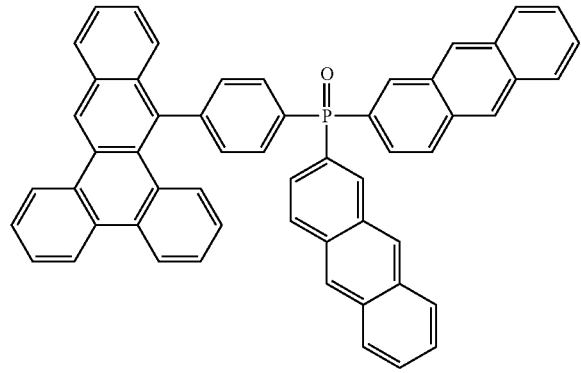
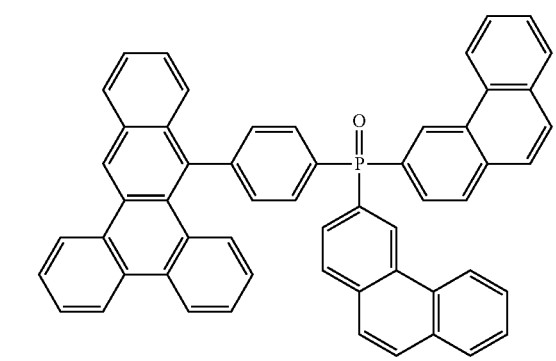
62
-continued
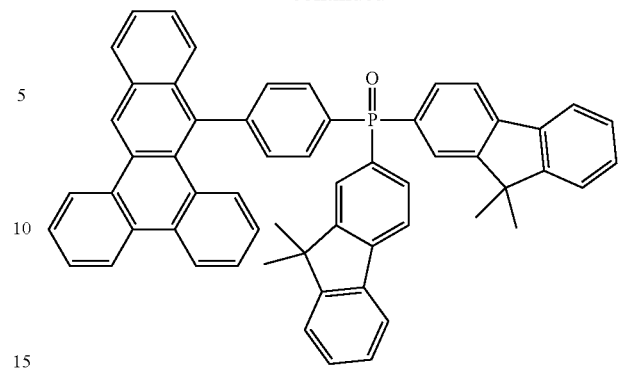
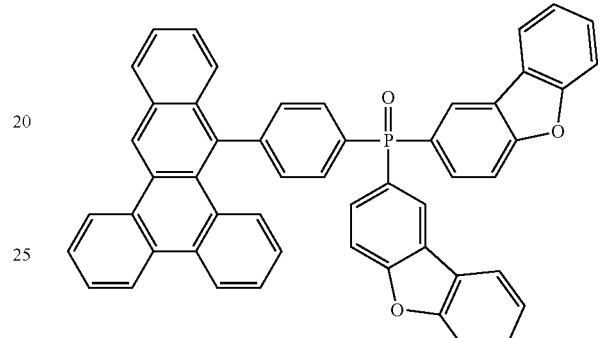
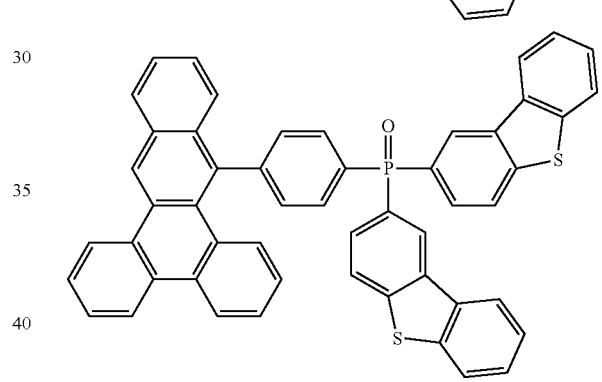
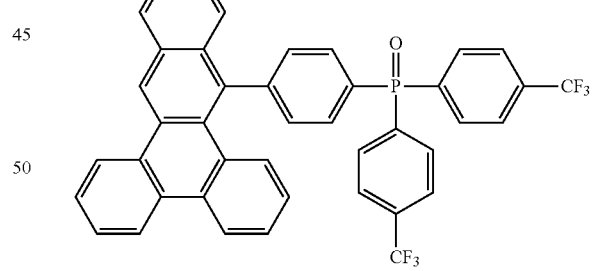
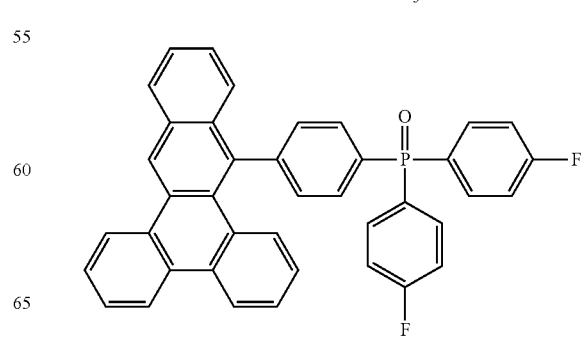

63
-continued
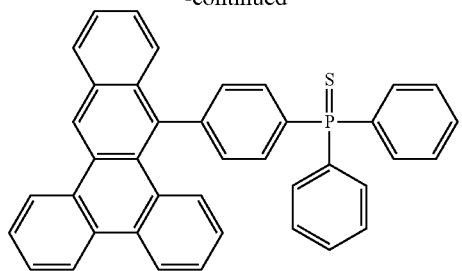
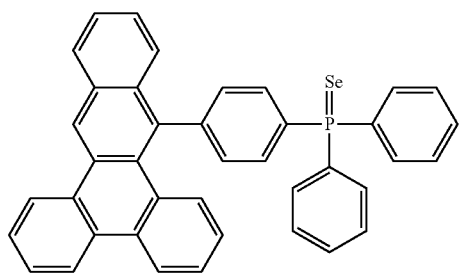
[Chem. 36]
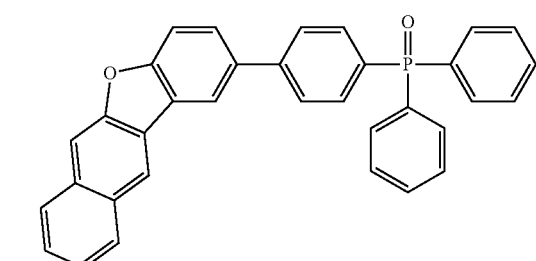
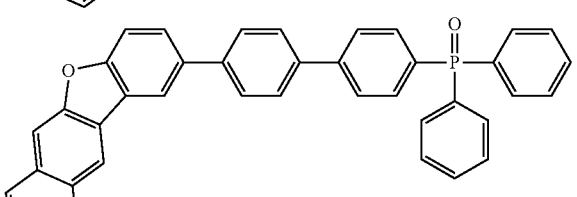
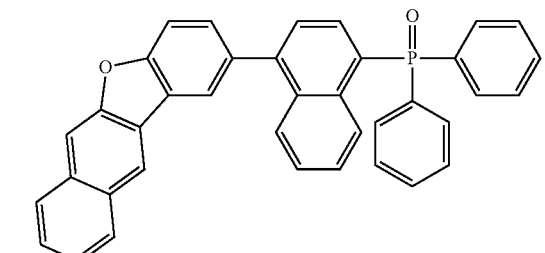
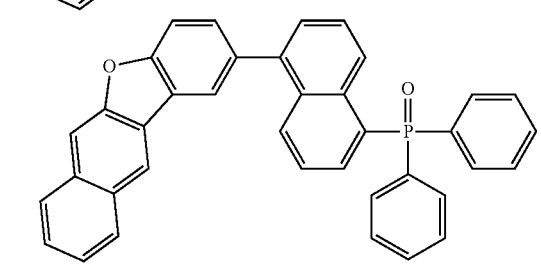
64
-continued
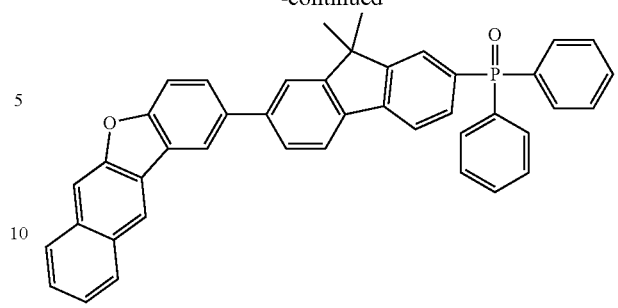
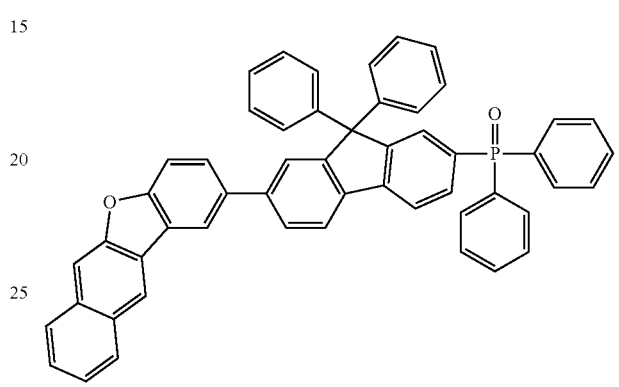
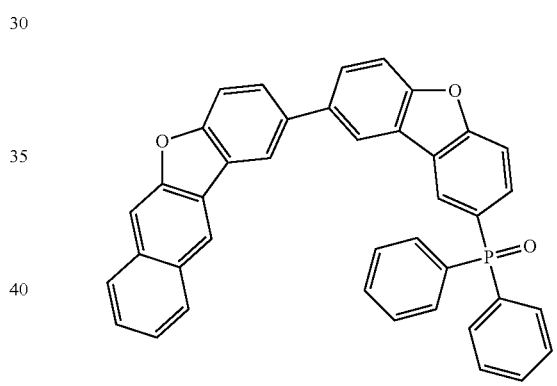
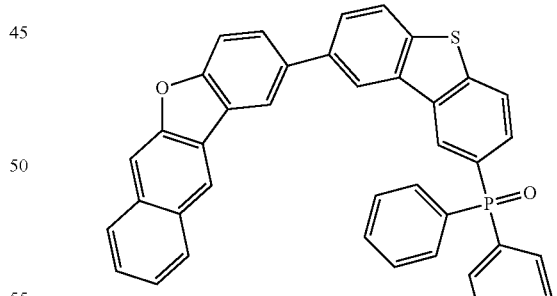
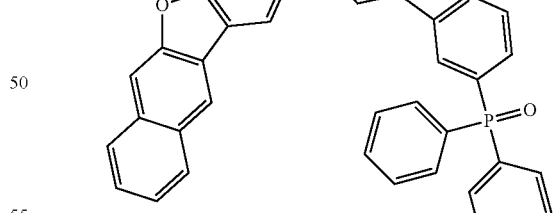
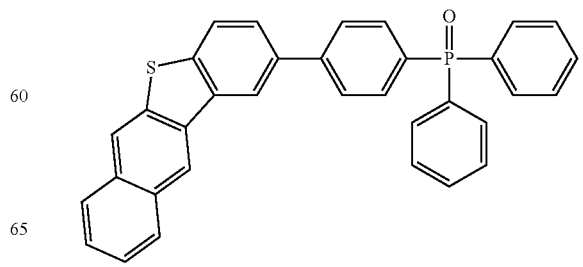

65
-continued
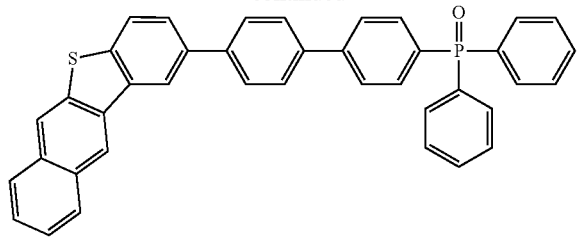
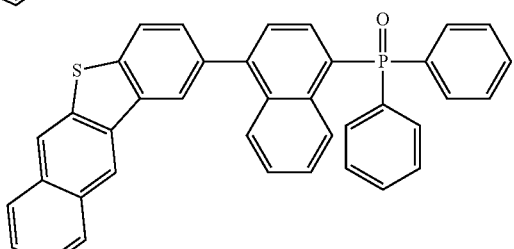
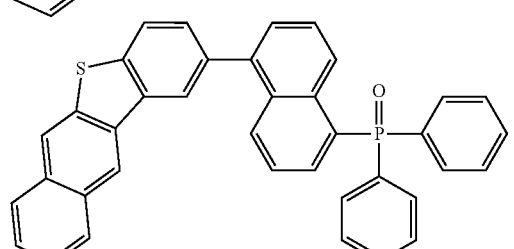
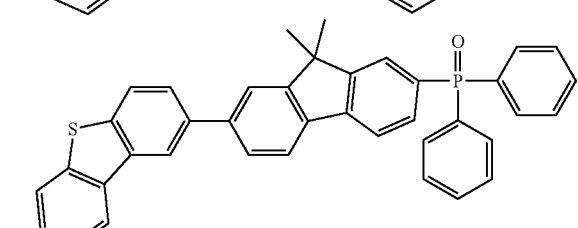
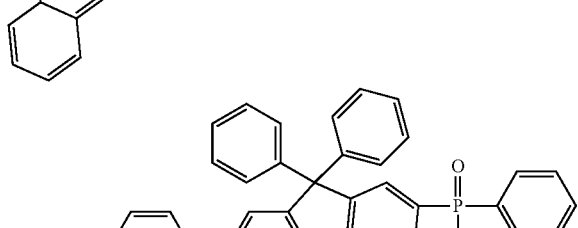
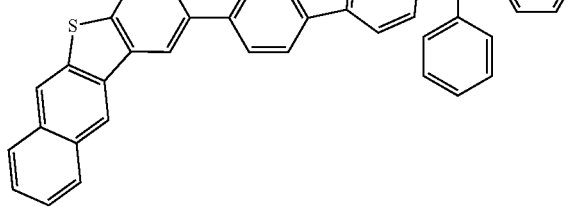
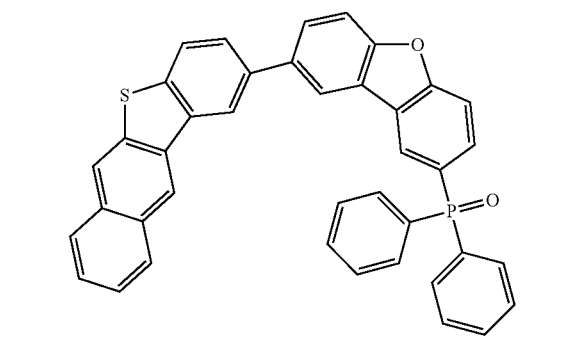
66
-continued
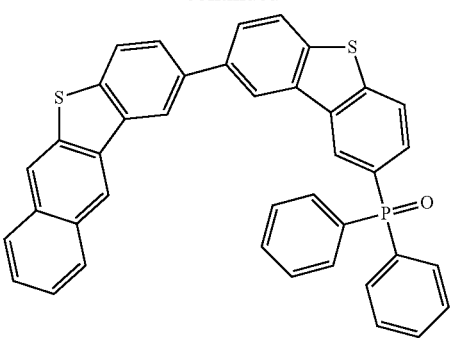
[Chem. 37]
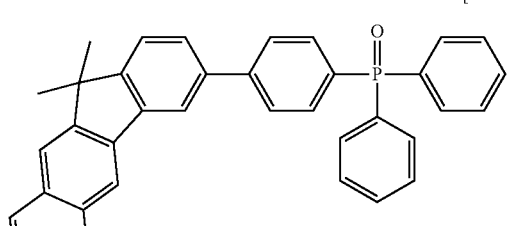
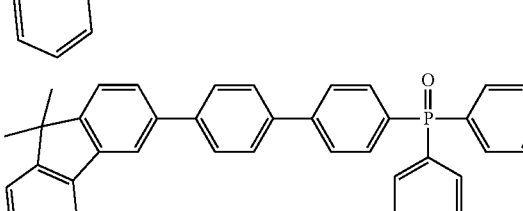
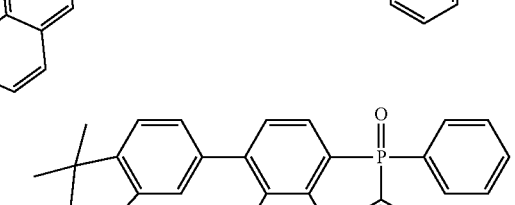
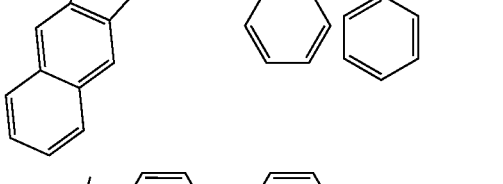
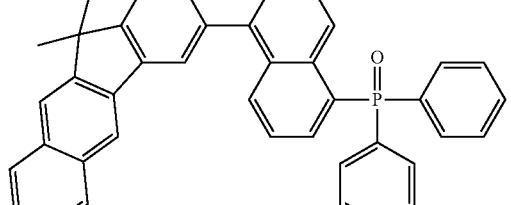
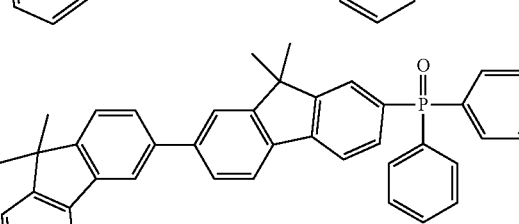

67
-continued
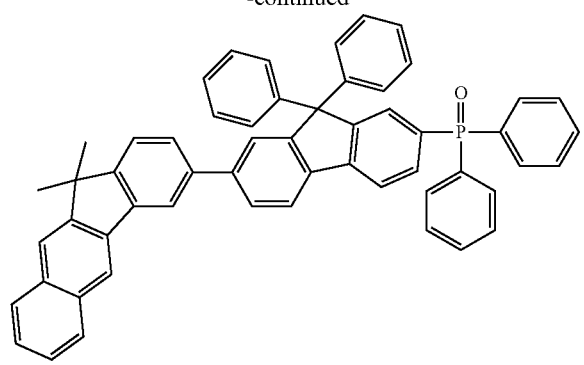
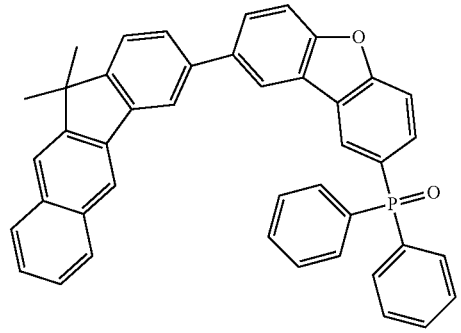
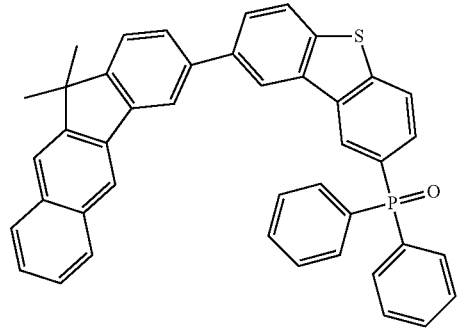
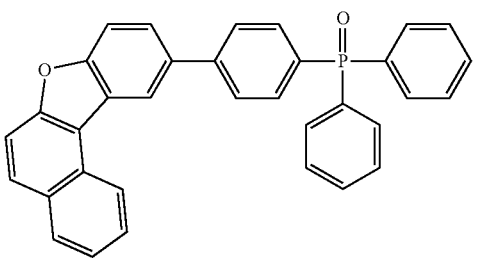
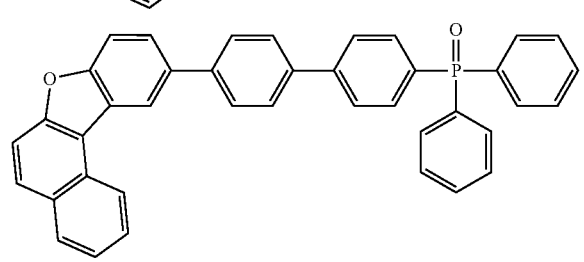
68
-continued
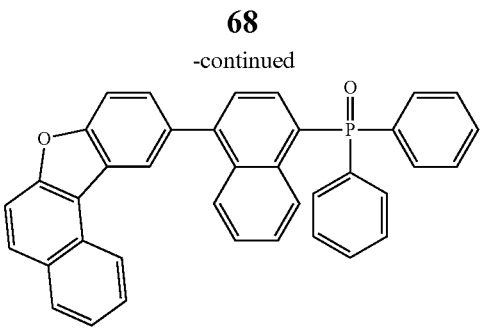
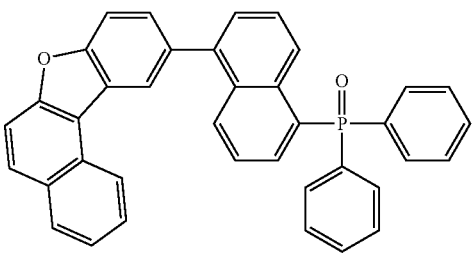
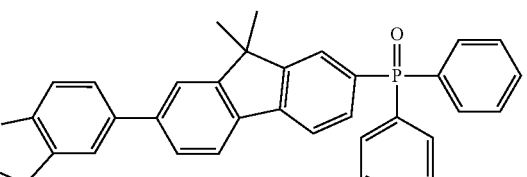
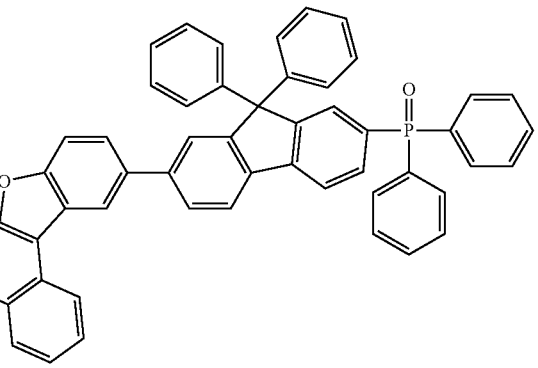
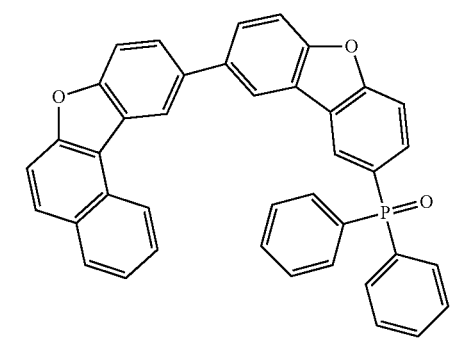

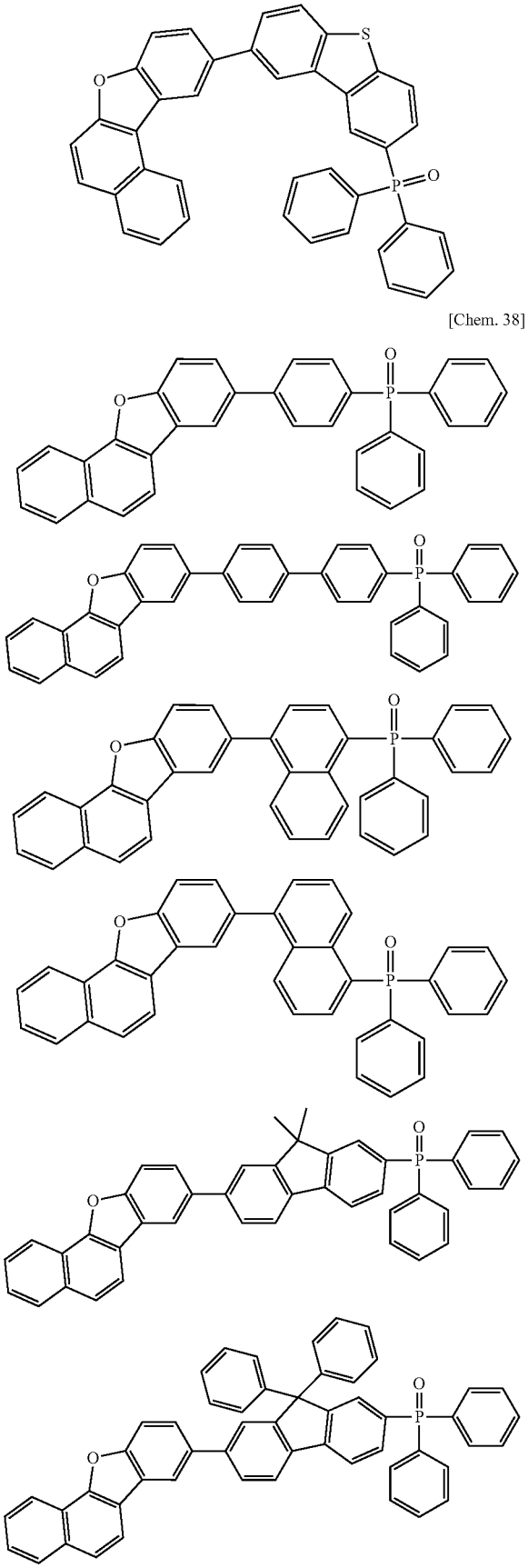

-continued

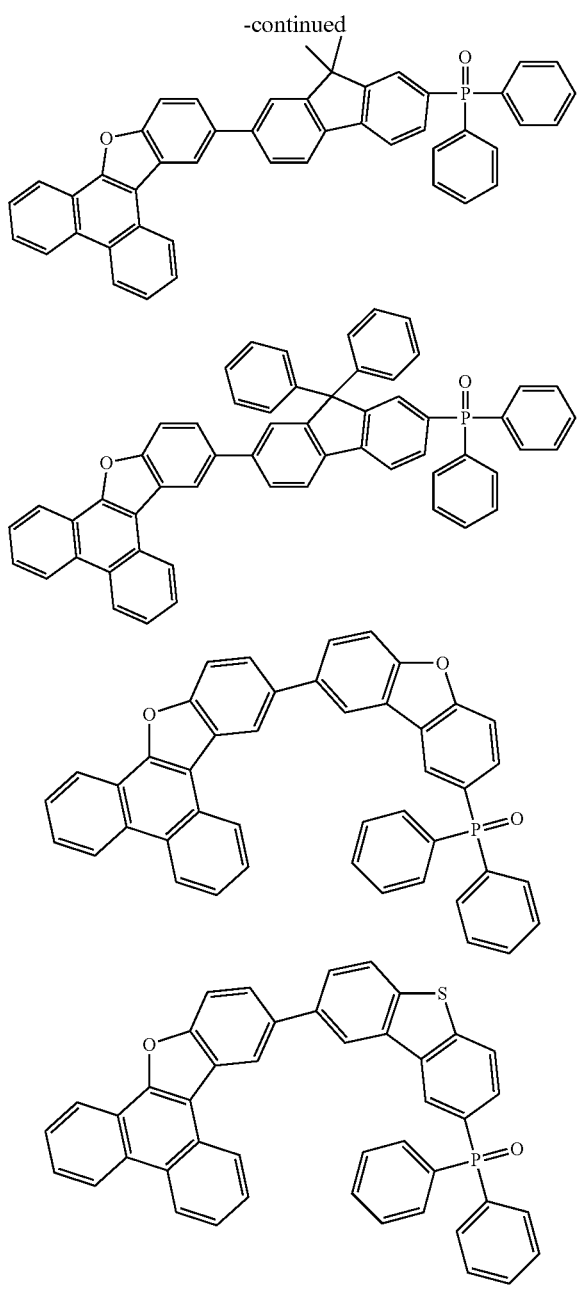

The compound of the present invention is useful as a material for organic EL devices. One kind of the compound of the present invention may be used alone as a material for organic EL devices or two or more kinds thereof may be used in combination. In addition, the compound of the present invention may be used in a mixture with a known material for organic EL devices.

[Organic Electroluminescence Device]

Next, an embodiment of the organic EL device of the present invention will be described.

The organic EL device of the present invention includes one or more organic thin film layers including at least a light emitting layer between a cathode and an anode facing to each other, at least one layer of the organic thin film layers including the compound of the present invention (hereinunder sometimes referred to as a material for organic EL devices of the present invention), thereby allowing an organic EL device to be driven at a low voltage, and enhancing the light emitting efficiency of the organic EL device, and prolonging the life thereof.

Examples of the layer containing the material for organic EL devices of the present invention include a hole transporting zone (also referred to as a hole transporting layer, however in the meaning of including the case of single hole transporting layer and the case of plural such layers, collectively referred to as a hole transporting zone) provided between an anode and a light emitting layer of an organic EL device, and an electron transporting zone (also referred to as an electron transporting layer, however in the meaning of including the case of single electron transporting layer and the case of plural such layers, collectively referred to as an electron transporting zone) provided between a cathode and a light emitting layer of an organic EL device, as well as a light emitting layer, a space layer and a blocking layer.

The material for organic EL devices of the present invention is preferably contained in an electron transporting zone, but not particularly limited thereto.

The organic EL devices of the present invention may be a fluorescent or phosphorescent type monochromatic light emitting device or a fluorescent/phosphorescent hybrid type white light emitting device, and may be a simple type having a single light emitting unit or a tandem type having plural light emitting units. Among them, a phosphorescent type is preferred. Here, the "light emitting unit" is the minimum unit including one or more organic layers, one of which is a light emitting layer which can emit light through recombination of a hole and an electron injected.

Accordingly, as a typical configuration of a simple type organic EL device, the following configuration for device may be mentioned.

(1) Anode/Light Emitting Unit/Cathode

The light emitting unit may be a laminated type having plural phosphorescent light emitting layers and/or plural florescent light emitting layers. In this case, a space layer may be provided between the light emitting layers in order to prevent diffusion of the exciton produced in a phosphorescent light emitting layer to a fluorescent light emitting layer. Typical configurations of layers of a light emitting unit are shown below.

(a) Hole transporting layer/light emitting layer (/electron transporting layer)

(b) Hole transporting layer/first phosphorescent light emitting layer/second phosphorescent light emitting layer (/electron transporting layer)

(c) Hole transporting layer/phosphorescent light emitting layer/space layer/fluorescent light emitting layer (/electron transporting layer)

(d) Hole transporting layer/first phosphorescent light emitting layer/second phosphorescent light emitting layer/space layer/fluorescent light emitting layer (/electron transporting layer)

(e) Hole transporting layer/first phosphorescent light emitting layer/space layer/second phosphorescent light emitting layer/space layer/fluorescent light emitting layer (/electron transporting layer)

(f) Hole transporting layer/phosphorescent light emitting layer/space layer/first fluorescent light emitting layer/second fluorescent light emitting layer (/electron transporting layer)

(g) Hole transporting layer/electron blocking layer/light emitting layer (/electron transporting layer)

(h) Hole transporting layer/light emitting layer/hole blocking layer (/electron transporting layer)

(i) Hole transporting layer/fluorescent light emitting layer/triplet blocking layer (/electron transporting layer)

In each case, an acceptor layer as described later may be, and preferably is, provided between the hole transporting layer and the anode.

The phosphorescent light emitting or fluorescent light emitting layers may show different luminescent colors from one another. Specifically, in the laminated light emitting layers (d), a layer configuration: hole transporting layer/first phosphorescent light emitting layer (emitting red light)/second phosphorescent light emitting layer (emitting green light)/space layer/fluorescent light emitting layer (emitting blue light)/electron transporting layer, is mentioned.

Incidentally, between the light emitting layer and the hole transporting layer or the space layer, an electron blocking layer may be appropriately provided. In addition, between the light emitting layer and the electron transporting layer, a hole blocking layer may be appropriately provided. By providing an electron blocking layer or a hole blocking layer, electrons or holes can be confined in the light emitting layer to enhance the probability of the recombination of the charges in the light emitting layer, thereby increasing the lifetime.

As a typical configuration of a tandem type organic EL device, the following configuration for device may be mentioned.

(2) Anode/First Light Emitting Unit/Intermediate Layer/Second Light Emitting Unit/Cathode Here, for each of the first light emitting unit and the second light emitting unit, for example, the same configurations of the light emitting unit as described above can be independently selected.

In general, the intermediate layer is also referred to as an intermediate electrode, an intermediate conductive layer, a charge producing layer, an electron withdrawing layer, a connecting layer, and an intermediate insulating layer, and a known configuration for material for supplying electrons to the first light emitting unit and holes to the second light emitting unit may be used therefor.

The FIGURE shows a schematic configuration of an example of the organic EL device of the present invention. An organic EL device 1 has a substrate 2, an anode 3, a cathode 4, and organic thin film layers 10 disposed between the anode 3 and the cathode 4. The organic thin film layers 10 include a light emitting layer 5 including at least one phosphorescent light emitting layer containing a phosphorescent host material and a phosphorescent dopant (a phosphorescent material). A hole transporting zone (hole transporting layer) 6 or the like may be formed between the light emitting layer 5 and the anode 3, and an electron transporting zone (electron transporting layer) 7 or the like may be formed between the light emitting layer 5 and the cathode 4. In addition, an electron blocking layer may be provided on the anode 3 side of the light emitting layer 5 and a hole blocking layer may be provided on the cathode 4 side of the light emitting layer 5. With these layers, electrons and holes can be confined in the light emitting layer 5 to increase the probability of the production of excitons in the light emitting layer 5.

Herein, a host combined with a fluorescent dopant is referred to as a fluorescent host, and a host combined with a phosphorescent dopant is referred to as a phosphorescent host. A fluorescent host and a phosphorescent host are not distinguished only by the molecular structure. That is, a phosphorescent host means a material constituting a phosphorescent light emitting layer containing a phosphorescent dopant, and does not means that the material can not be used as a material constituting a fluorescent light emitting layer. The same is applied to a fluorescent host.

(Substrate)

The substrate is used as a support of the light emitting device. As the substrate, for example, a glass, quartz and a plastic can be used. A flexible substrate may also be used. A flexible substrate means a substrate which can be bended (which is flexible), and examples thereof include plastic substrates made of polycarbonate, polyacrylate, polyethersulfone, polypropylene, polyester, polyvinyl fluoride, and polyvinyl chloride. An inorganic vapor-deposited film may also be used.

(Anode)

In the anode formed on the substrate, a metal, an alloy, a conductive compound, a mixture thereof, or the like which have a large work function (specifically 4.0 eV or more) is preferably used. Specific examples include indium oxide-tin oxide (ITO: indium tin oxide), indium oxide-tin oxide containing silicon or silicon oxide, indium oxide-zinc oxide, tungsten oxide, indium oxide containing zinc oxide, and graphene. Besides the above, gold (Au), platinum (Pt), nitride of a metal material (for example, titanium nitride), and the like are exemplified.

(Hole Transporting Zone)

The organic EL device of the present invention preferably includes a hole transporting zone between the light emitting layer and the anode.

The hole transporting zone includes a substance having high hole injecting capability and/or high hole transporting capability.

As a substance having high hole injecting capability, molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, and the like can be used.

Examples thereof include aromatic amine compounds such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1), which are low molecular organic compounds.

A high molecular compound (an oligomer, a dendrimer, a polymer, etc.) may also be used. For example, high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD) may be mentioned. In addition, a high molecular compound having an acid added thereto, such as poly(3,4-ethylenedioxythiophene)/poly(styrenesulfonic acid) (PEDOT/PSS) and polyaniline/poly(styrenesulfonic acid) (PAni/PSS), may be used.

Besides the above, in the hole transporting zone, an aromatic amine compound, a carbazole derivative, an anthracene derivative, and the like, which have high hole transporting capability, can be used. Specifically, an aromatic amine compound such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluoren-9-yl)triphenylamine (abbreviation: BAFLP), 4,4'-bis[N-(9,9-dimethylfluoren-2-yl)-N-phenylamino]biphenyl (abbreviation: DFLDPBi), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB), etc. can be used. The substances described here are mainly a substance having a hole mobility of $10^{-6}$ cm$^2$/Vs or more.

For the hole transporting layer, a carbazole derivative such as CBP, CzPA, and PCzPA, and an anthracene derivative such as t-BuDNA, DNA, and DPAnth may be used. A high molecular compound such as poly(N-vinylcarbazole) (abbreviation: PVK) and poly(4-vinyltriphenylamine) (abbreviation: PVTPA) can also be used.

However, a substance other than the above may be used as long as it has higher capability in hole transporting than in electron transporting.

A hole transporting layer in an organic EL device of one embodiment of the present invention may have a two-layer structure of a first hole transporting layer (on the anode side) and a second hole transporting layer (on the cathode side).

The thickness of the hole transporting layer is not particularly limited, but it is preferably 10 nm to 300 nm. Incidentally, when the hole transporting layer has the two-layer structure, the thickness of the first hole transporting layer is preferably, but not limited to, 50 to 300 nm, more preferably 50 to 250 nm, further preferably 50 to 150 nm, especially preferably 50 to 100 nm, and the thickness of the second hole transporting layer is preferably, but not limited to, 5 to 100 nm, more preferably 5 to 50 nm, further preferably 5 to 30 nm, especially preferably 5 to 20 nm.
(Gest Material of Light Emitting Layer)

The light emitting layer is a layer including a substance having high light emitting capability, and various materials can be used therefor. For example, as the substance having high light emitting capability, a fluorescent compound emitting fluorescence and a phosphorescent compound emitting phosphorescence can be used. A fluorescent compound is a compound that can emit light from the singlet exited state, and a phosphorescent compound is a compound that can emit light from the triplet exited state.

Examples of a blue fluorescent material which can be used in the light emitting layer include a pyrene derivative, a styrylamine derivative, a chrysene derivative, a fluoranthene derivative, a fluorene derivative, a diamine derivative, and a triarylamine derivative. Specifically N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(10-phenyl-9-antyryl)-4'-(9-phenyl-9H-carbazol-3-yl)triphenylamine (abbreviation: PCBAPA), etc. may be mentioned.

Examples of a green fluorescent material which can be used in the light emitting layer include an aromatic amine derivative. Specifically, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), N, N, 9-triphenylanthracen-9-amine (abbreviation: DPhAPhA), etc. may be mentioned.

Examples of a red fluorescent material which can be used in the light emitting layer include a tetracene derivative and a diamine derivative. Specifically, N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), etc. may be mentioned.

Examples of a blue phosphorescent material which can be used in the light emitting layer include a metal complex such as an iridium complex, an osmium complex and a platinum complex, preferably an orthometalated complex of iridium, osmium or platinum metal. Specifically, bis[2-(4',6'-difluorophenyl)pyridinato-N,C2']iridium(III) tetrakis(1-pyrazoryl)borate (abbreviation: FIr6), bis[2-(4',6'-difluorophenyl) pyridinato-N,C2']iridium(III) picolinato (abbreviation: FIrpic), bis[2-(3',5'bistrifluoromethylphenyl)pyridinato-N,C2']iridium(III) picolinato (abbreviation: Ir(CF3ppy)2 (pic)), bis[2-(4',6'-difluorophenyl)pyridinato-N,C2']iridium (III) acetylacetonate (abbreviation: FIracac), etc. may be mentioned.

Examples of a green phosphorescent material which can be used in the light emitting layer include an iridium complex. Specifically, tris(2-phenylpyridinato-N,C2') iridium(III) (abbreviation: Ir(ppy)3), bis(2-phenylpyridinato-N,C2')iridium(III) acetylacetonate (abbreviation: Ir(ppy)2(acac)), bis(1,2-diphenyl-1H-benzoimidazolato) iridium(III) acetylacetonate (abbreviation: Ir(pbi)2(acac)), bis(benzo[h]quinolinato)iridium(III) acetylacetonate (abbreviation: Ir(bzq)2(acac)), etc. may be mentioned.

Examples of a red phosphorescent material which can be used in the light emitting layer include a metal complex such as an iridium complex, a platinum complex, a terbium complex and a europium complex. Specifically, an organic metal complex such as bis[2-(2'-benzo[4,5-a]thienyl)pyridinato-N,C3']iridium(III) acetylacetonate (abbreviation: Ir(btp)2(acac)), bis(1-phenylisoquinolinato-N,C2')iridium (III) acetylacetonate (abbreviation: Ir(piq)2(acac), (acetylacetonato)bis[2,3-bis(4-fluorophenyl)quinoxalinato] iridium(III) (abbreviation: Ir(Fdpq)2(acac)), 2,3,7,8,12,13, 17,18-octaethyl-21H,23H-porphiline platinum(II) (abbreviation: PtOEP), etc. may be mentioned.

In addition, a rare earth metal complex such as tris (acetylacetonato)(monophenanthroline)terbium(III) (abbreviation: Tb(acac)3(Phen)), tris(1,3-diphenyl-1,3-propanedionato)(monophenanthroline)europium(III) (abbreviation: Eu(DBM)3(Phen)), and tris[1-(2-thenoyl)-3,3,3-trifluoroacetonatol](monophenanthrolone)europium(III) (abbreviation: Eu(TTA)3(Phen)) emits light from the rare earth metal ions (electron transition between different multiplets), and therefore can be used as a phosphorescent compound.
(Host Material for Light Emitting Layer)

The light emitting layer may have a configuration in which the substance having high light emitting capability (gest material) is dispersed in another substance (host material). As the material in which the substance having high light emitting capability is dispersed, a variety of substances can be used and a substance having a higher lowest unoccupied molecular orbital level (LUMO level) and a lower highest occupied molecular orbital level (HOMO level) than the substance having high light emitting capability is preferably used.

As the material (host material) in which the substance having high light emitting capability is dispersed, the compound of the present invention is preferred. Besides the compound of the present invention, for example, 1) a metal complex such as an aluminum complex, a beryllium complex and a zinc complex, 2) a heterocyclic compound such as an oxadiazole derivative, a benzimidazole derivative and a phenanthroline derivative, 3) a condensed aromatic compound such as a carbazole derivative, an anthracene derivative, a phenanthrene derivative, a pyrene derivative and a chrysene derivative, and 3) an aromatic amine compound such as a triaryl amine derivative and a condensed polycyclic aromatic amine derivative can be used. More specifically, a metal complex such as tris(8-quinolinolato)aluminum(III) (abbreviation: Alq), tris(4-methyl-8-quinolinolato) aluminum(III) (abbreviation: Almq3), bis(10-hydroxybenzo[h]quinolinato)beryllium(II) (abbreviation: BeBq2), bis(2-methyl-8-quinolinolato)(4-phenylphenolato)aluminum(III) (abbreviation: BAlq), bis(8-quinolinolato)zinc(II) (abbreviation: Znq), bis[2-(2-benzooxazolyl)phenolato]zinc(II) (abbreviation: ZnPBO), and bis[2-(2-benzothiazolyl)phenolato]zinc(II) (abbreviation: ZnBTZ); a heterocyclic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)tris(1-phenyl-1H-benzoimidazole) (abbreviation: TPBI), bathophenanthroline (abbreviation: BPhen), and bathocuproine (abbreviation: BCP); a condensed aromatic compound such as 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3''-(benzene-1,3,5-triyl)tripyrene (abbreviation: TPB3), 9,10-diphenylanthracene (abbreviation: DPAnth), and 6,12-dimethoxy-5,11-diphenylchrysene; an aromatic amine compound such as N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), NPB (or α-NPD), TPD, DFLDPBi, and BSPB; and the like can be used. As the substance (host material) in which a substance (gest material) having high light emitting capability is dispersed, plural kinds may be used.

(Electron Transporting Zone)

The electron transporting zone includes a substance having high electron injecting capability and/or high electron transporting capability. As described above, an electron transporting zone preferably contains the compound of the present invention.

For the electron transporting zone, an alkali metal, an alkaline earth metal, or a compound thereof, such as lithium (Li), cesium (Cs), calcium (Ca), lithium fluoride (LiF), cesium fluoride (CsF), calcium fluoride (CaF$_2$) and lithium oxide (LiOx) which are substances having high electron injecting capability can be used. Besides the above, a substance having electron transporting capability having an alkali metal, an alkaline earth metal, or a compound thereof contained therein, specifically, Alq containing magnesium (Mg) and the like may be used. In this case, electron injection from the cathode can be achieved more efficiently.

Alternatively, for the electron transporting zone, a composite material in which an organic compound is mixed with an electron donating dopant may be used. Such a composite material produces electrons in the organic compound by the electron donating dopant, and therefore is superior in electron injecting capability and electron transporting capability. In this case, as the organic compound, a material having good capability in transporting the produced electrons is preferred, and specifically the compound of the present invention and a substance constituting the electron transporting layer mentioned above (a metal complex, a heteroaromatic compound, etc.) can be used. As the electron donating dopant, any substance having electron donating capability to the organic compound can be used. Specific examples include an alkali metal, an alkali metal compound, an alkaline earth metal, an alkaline earth metal compound, a rare earth metal, and a rare earth metal compound, and at least one selected therefrom is preferred. Examples of the alkali metal, alkaline earth metal and rare earth metal include lithium, cesium, magnesium, calcium, erbium, and ytterbium. An alkali metal oxide and an alkaline earth metal oxide are also preferred, and, for example, lithium oxide, calcium oxide, barium oxide, etc. may be used. In addition, a Lewis base such as magnesium oxide can be used. An organic compound such as tetrathiafulvalene (abbreviation: TTF) can also be used.

Besides the above, for the electron transporting zone, 1) an organic metal complex such as an aluminum complex, a beryllium complex and a zinc complex, 2) a heteroaromatic compound such as an imidazole derivative, a benzimidazole derivative, an azine derivative, a carbazole derivative and a phenanthroline derivative, 3) a high molecular compound, which are substances having high electron transporting capability, can be used.

As the organic metal complex, at least one kind selected from an organic metal complex containing an alkali metal, an organic metal complex containing an alkaline earth metal and an organic metal complex containing a rare earth metal is preferably used.

Specific examples of the organic metal complex include 8-quinolinolato lithium (abbreviation: Liq), Alq, tris(4-methyl-8-quinolinolato)aluminum (abbreviation: Almq3), bis(10-hydroxybenzo[h]quinolinato)beryllium (abbreviation: BeBq$_2$), BAlq, Znq, ZnPBO, and ZnBTZ.

Specific examples of the heteroaromatic compound include 2-(4-biphenylyl)-5-(4-tert-butylphenyl)-1,3,4-oxadiazole (abbreviation: PBD), 1,3-bis[5-(ptert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproin (abbreviation: BCP), and 4,4'-bis(5-methylbenzooxazol-2-yl)stilbene (abbreviation: BzOs).

Specific examples of the high molecular compound include poly[(9,9-dihexylfluorene-2,7-diyl)-co-(pyridine-3,5-diyl)] (abbreviation: PF-Py) and poly[(9,9-dioctylfluorene-2,7-diyl)-co-(2,2'-bipyridine-6,6'-diyl)] (abbreviation: PF-BPy).

The substances described here are mainly substances having an electron mobility of $10^{-6}$ cm$^2$/Vs or more. Incidentally, other substances than the above may be used as the electron transporting layer as long as it has higher capability in electron transporting than in hole transporting. The electron transporting zone may be not only a single layer but also a laminate in which two or more layers including the substances mentioned above are stacked.

In an organic EL device of an embodiment of the present invention, the electron transporting zone preferably further contains at least one selected from the electron donating dopant and the organic metal complex mentioned above in addition to the compound of the present invention.

(Cathode)

For the cathode, a metal, an alloy, a conductive compound, a mixture thereof, or the like which have a small work function (specifically 3.8 eV or less) is preferably used. Specific examples of the cathode material include an element belonging to the first group or the second group of the Periodic Table of Elements, i.e., an alkali metal such as lithium (Li) and cesium (Cs), an alkaline earth metal such as magnesium (Mg), an alloy containing such a metal (for example, MgAg and AlLi), and a rare earth metal such as and an alloy containing such a metal.

(Acceptor Layer)

The organic EL device of one embodiment of the present invention may include, and preferably includes, a layer containing an acceptor material, that is, an acceptor layer, between the anode and the hole transporting zone. With this configuration, a lowered driving voltage and a reduced production cost can be expected.

As the acceptor material, the compound represented by the following formula (K) is preferred.

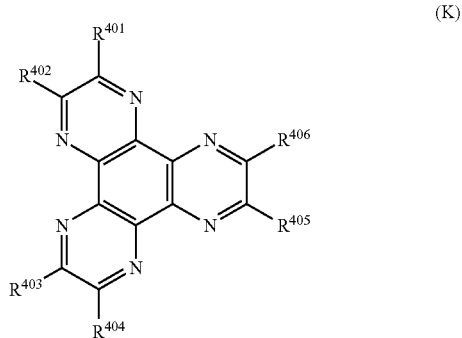

(K)

In the formula (K), $R^{401}$ to $R^{406}$ are each independently a cyano group, —$CONH_2$, a carboxyl group, or —$COOR^{407}$ ($R^{407}$ is an alkyl group having 1 to 20 carbon atoms), or $R^{401}$ and $R^{402}$, $R^{403}$ and $R^{404}$, or $R^{405}$ and $R^{406}$ bind to each other to form a group represented by —CO—O—CO—.

Examples of the alkyl group represented by $R^{407}$ include a methyl group, an ethyl group, an n-propyl group, an isopropyl group, an n-butyl group, an isobutyl group, a tert-butyl group, a cyclopentyl group, and a cyclohexyl group.

Thickness of the layer containing the acceptor material is not particularly limited, but preferably 5 to 20 nm.

(n/p Doping)

In the hole transporting layer and electron transporting layer described above, as described in JP-B-3695714, the carrier injecting capability can be adjusted by doping (n) of the donating material or doping (p) of an accepting material.

Typical examples of the n-doping include a method of doping an electron transporting material with a metal such as Li and Cs, and typical examples of the p-doping include a method of doping a hole transporting material with an acceptor material such as 2,3,5,6-tetrafluoro-7,7,8,8-tetra-cyanoquinodimethane ($F_4TCNQ$).

(Space Layer)

The space layer means a layer provided, when, for example, a fluorescent light emitting layer and a phosphorescent light emitting layer are laminated, between a fluorescent light emitting layer and a phosphorescent light emitting layer, for the purpose of preventing dispersion of excitons produced in the phosphorescent light emitting layer to the fluorescent light emitting layer, or adjusting the carrier balance. The space layer may be also provided between plural phosphorescent light emitting layers.

Since the space layer is provided between light emitting layers, a material having both of electron transporting capability and hole transporting capability is preferred. For preventing diffusion of the triplet energy in the adjacent phosphorescent light emitting layer, the triplet energy is preferably 2.6 eV or more. As a material for use in the space layer, the same material as for the hole transporting layer may be mentioned.

(Blocking Layer)

In an organic EL device of an embodiment of the present invention, a blocking layer such as an electron blocking layer, a hole blocking layer and a triplet blocking layer may be provided in a portion adjacent to the light emitting layer. Here, the electron blocking layer is a layer for preventing electrons from leaking from the light emitting layer to the hole transporting layer, and the hole blocking layer is a layer for preventing holes from leaking from the light emitting layer to the electron transporting layer.

The triplet blocking layer has a function of preventing diffusion of triplet excitons produced in the light emitting layer into surrounding layers and confining the triplet excitons in the light emitting layer, thereby suppressing energy deactivation on the molecules other than the light emitting dopant of the triplet excitons in the electron transporting layer.

In the case of providing a triplet blocking layer, the following is presumed. That is, in a phosphorescent device, when $E^T_d$ is the triplet energy of the phosphorescent dopant in the light emitting layer and $E^T_{TB}$ is the triplet energy of the compound used as the triplet blocking layer, if the relationship of the energy: $E^T_d < E^T_{TB}$ is satisfied, the triplet excitons of the phosphorescent dopant are confined due to the relationship of the energy (prevented from moving to other molecules), and other route for the energy deactivation than the light emission on the dopant is interrupted, thereby enabling high efficient light emission. However, even when the relationship: $E^T_d < E^T_{TB}$ is satisfied, if this difference in energy: $\Delta E^T = E^T_{TB} - E^T_d$ is small, under the environment of a room temperature or so which is an actual environment for driving the device, it is considered to be possible for the triplet excitons to endothermally overcome the energy difference $\Delta E^T$ by the thermal energy of the surrounding environment to move to the other molecules. In particular, the phosphorescence shows longer exciton lifetime than fluorescence, the effect of the endothermal exciton moving route is relatively larger. A larger value of the energy difference $\Delta E^T$ relative to the thermal energy of room temperature is more preferred. The energy difference is more preferably 0.1 eV or more, and especially preferably 0.2 eV or more.

The electron mobility of the material constituting the triplet blocking layer is, in the range of the field intensity of 0.04 to 0.5 MV/cm, preferably $10^{-6}$ $cm^2/Vs$ or more. As a method for measuring electron mobility of an organic material, several methods such as the time-of-flight method are known. Here, the electron mobility determined by the impedance spectroscopy is adopted.

The electron mobility of the material constituting the electron injecting layer is, in the range of the field intensity of 0.04 to 0.5 MV/cm, desirably $10^{-6}$ cm$^2$/Vs or more. Such an electron mobility promotes electron injection from the cathode to the electron transporting layer, in turn promoting electron injection to the adjacent blocking layer and the light emitting layer, thereby enabling low voltage driving.

An organic EL device obtained by using the compound of the present invention can be driven at a low voltage, has a high light emitting efficiency and an extended lifetime. Thus, such an organic EL device can be used in electronic equipments such as a display part of an organic EL panel module and the like, a display device for a television, a cell phone, a personal computer and the like, and a luminescence device of an illumination or a lighting unit for vehicle.

EXAMPLES

Next, the present invention will be described in more detail with reference to examples and comparative examples, but the present invention is by no means limited to the description of the examples.

Example 1

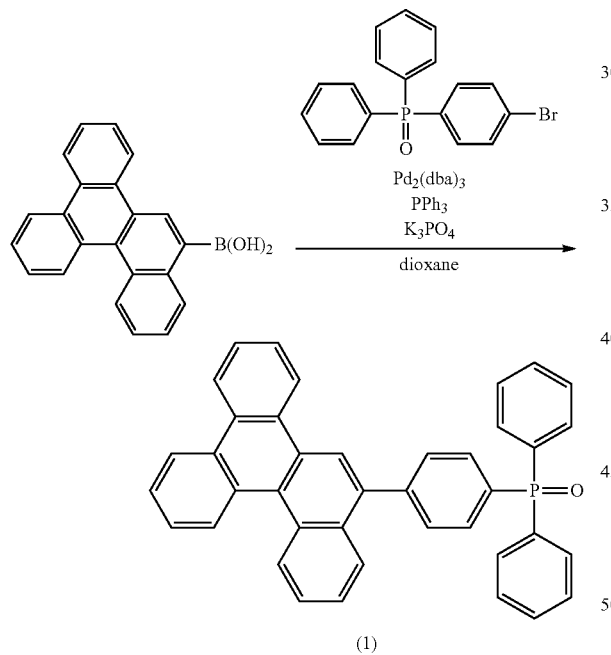

Under the argon atmosphere, 1,4-dioxane (100 mL) was added to benzo[g]chrysene-10-boronic acid (2.90 g, 9.00 mmol), (4-bromophenyl)phosphine oxide (3.21 g, 9.00 mmol), tris(dibenzylideneacetone)dipalladium(0) (124 mg, 0.135 mmol), triphenylphosphine (283 mg, 1.08 mmol), and tripotassium phosphate (11.5 g, 54.0 mmol), and the mixture was stirred at 100° C. for 8 hours.

After the completion of the reaction, the mixture was diluted with water, and extracted with chloroform. Subsequently, the mixture was washed with a saturated saline solution, dried over magnesium sulfate and then concentrated. After that, the mixture was purified by silica gel chromatography and then recrystallized from ethyl acetate to obtain a compound (3.24 g, 5.85 mmol, yield: 65%). The compound showed, as a result of a mass analysis, m/e=554, and was identified as the compound (1) (exact mass: 554.18).

Example 2

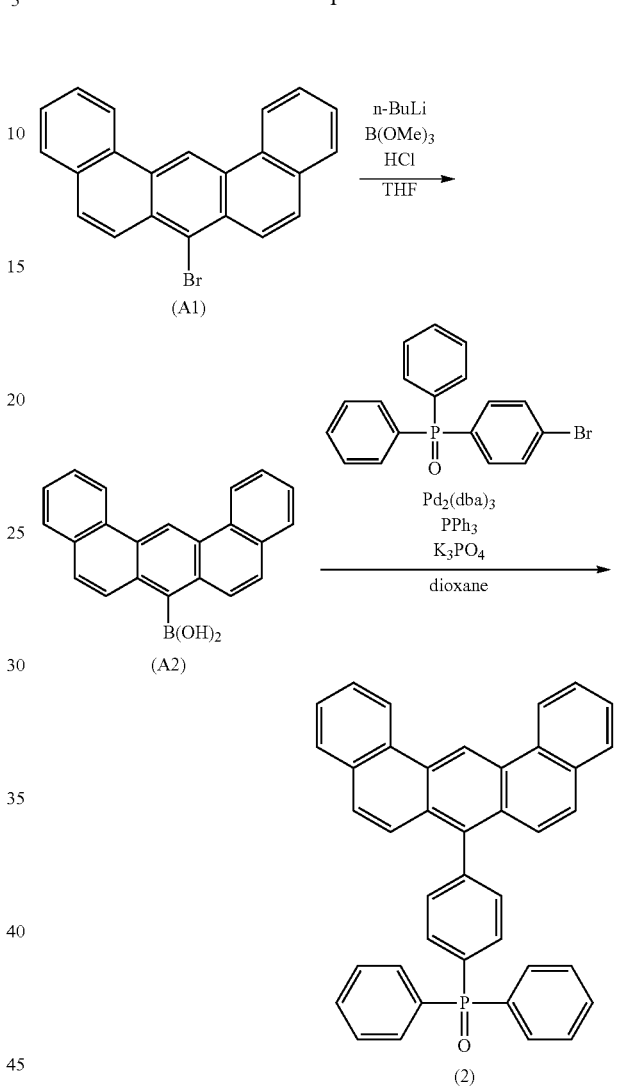

(2-1) Synthesis of Intermediate (A2)

Under the argon atmosphere, the raw material compound (A1) (2.00 g, 5.60 mmol) and tetrahydrofuran (50 mL) were mixed, and cooled to −78° C. After that, n-butyllithium (1.60 M solution in hexane, 3.68 mL, 5.88 mmol) was added and the temperature was raised to 0° C. over 2 hours. Next, the mixture was cooled again to −78° C., trimethoxyborane (1.45 g, 14.0 mmol) was added, the mixture was stirred at 78° C. for 10 minutes, and the temperature was raised to a room temperature over 6 hours.

After the completion of the reaction, an aqueous hydrogen chloride solution (1 M, 15 mL) was added and the mixture was stirred at a room temperature for 1 hour and extracted with ethyl acetate. The solution was dried over magnesium sulfate, then concentrated, suspended in and washed with hexane, and collected by filtration to obtain the intermediate (A2) (902 mg, 2.80 mmol, yield: 50%).

(2-2) Synthesis of Compound (2)

Under the argon atmosphere, 1,4-dioxane (30 mL) was added to the intermediate (A2) (850 mg, 2.64 mmol), (4-bromophenyl)phosphine oxide (942 mg, 2.64 mmol), tris(dibenzylideneacetone)dipalladium(0) (36 mg, 0.0396 mmol), triphenylphosphine (83 mg, 0.317 mmol), and tripotassium phosphate (3.36 g, 15.8 mmol), and the mixture was stirred at 100° C. for 8 hours.

After the completion of the reaction, the mixture was diluted with water, and extracted with chloroform. Subsequently, the mixture was washed with a saturated saline solution, dried over magnesium sulfate and then concentrated. After that, the mixture was purified by silica gel chromatography and then recrystallized from ethyl acetate to obtain a compound (864 g, 1.56 mmol, yield: 59%). The compound showed, as a result of a mass analysis, m/e=554, and was identified as the compound (2) (exact mass: 554.18).

Example 3

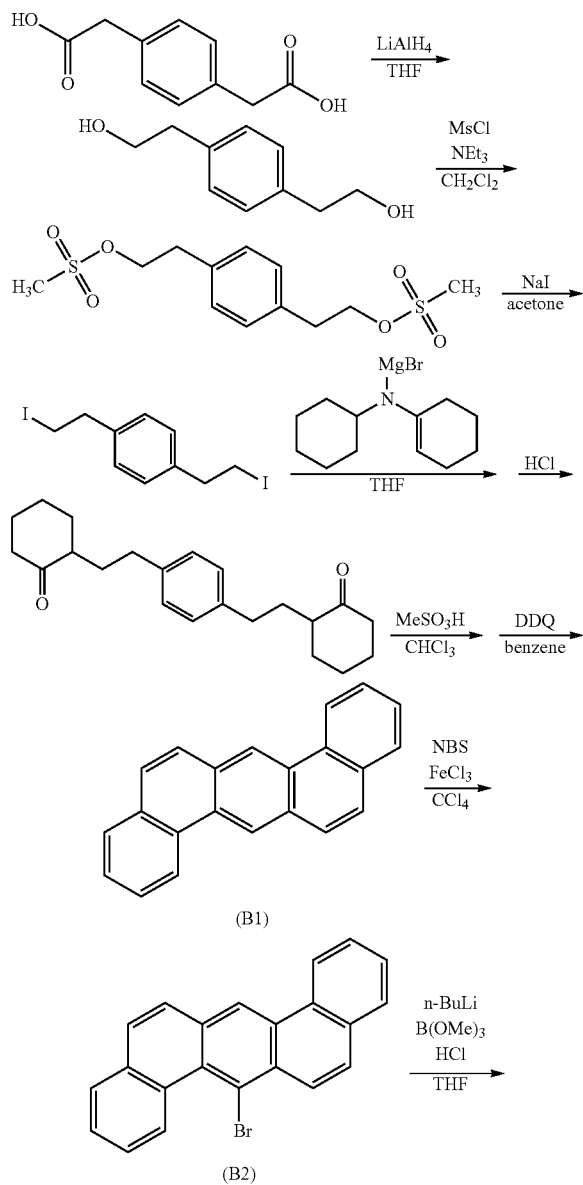

(3-1) Synthesis of Intermediate (B1)

With reference to a synthesis example described in "J. Org. Chem., 1991, 56, p. 1210-1217", the intermediate (B1) was synthesized as described above.

(3-2) Synthesis of Intermediate (B2)

Carbon tetrachloride (600 mL) was added to the intermediate (B1) (2.40 g, 8.66 mmol), N-bromosuccinimide (1.54 g, 8.66 mmol), and iron(III) chloride hexahydrate (70 mg, 0.260 mmol), and the mixture was stirred under reflux with heating for 8 hours.

After the completion of the reaction, the solvent was removed under a reduced pressure, and the mixture was purified by silica gel chromatography to obtain the intermediate (B2) (2.13 g, 5.98 mmol, yield: 69%).

(3-3) Synthesis of Intermediate (B3)

Under the argon atmosphere, the intermediate (B2) (1.80 g, 5.04 mmol) and tetrahydrofuran (40 mL) were mixed and the mixture was cooled to −78° C. After that, n-BuLi (1.60 M solution in hexane, 3.31 mL, 5.29 mmol) was added and the temperature was raised to 0° C. over 2 hours. Next, the mixture was cooled again to −78° C., trimethoxyborane (1.31 g, 12.6 mmol) was added and the mixture was stirred at −78° C. for 10 minutes, and the temperature was raised to a room temperature over 7 hours.

After the completion of the reaction, an aqueous hydrogen chloride solution (1 M, 15 mL) was added, and the mixture was stirred at a room temperature for 1 hour, and extracted with ethyl acetate. The solution was dried over magnesium sulfate, then concentrated, suspended in and washed with hexane, and collected by filtration to obtain the intermediate (B3) (698 mg, 2.17 mmol, yield: 43%).

(3-4) Synthesis of Compound (3)

Under the argon atmosphere, 1,4-dioxane (25 mL) was added to the intermediate (B3) (680 mg, 2.11 mmol), (4-bromophenyl)phosphine oxide (754 mg, 2.11 mmol), tris

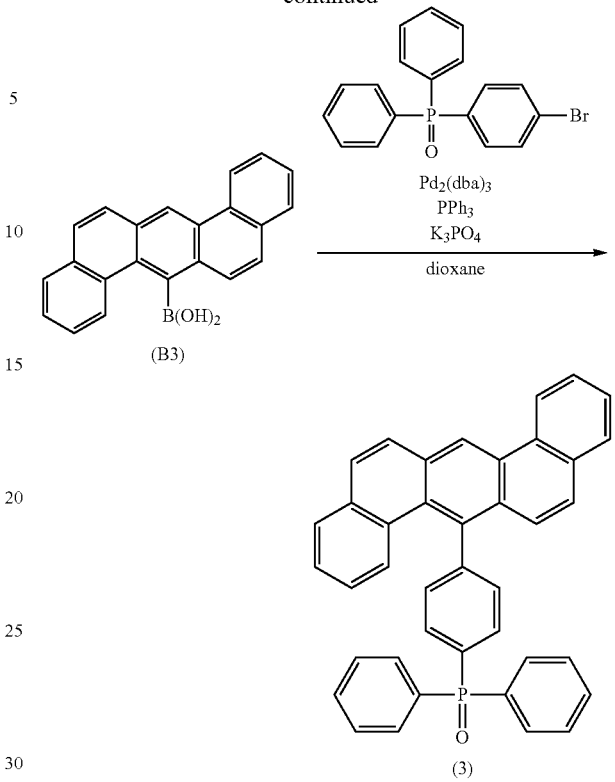

(dibenzylideneacetone)dipalladium(0) (29 mg, 0.0317 mmol), triphenylphosphine (66 mg, 0.253 mmol), and tripotassium phosphate (2.69 g, 12.7 mmol), and the mixture was stirred at 100° C. for 10 hours.

After the completion of the reaction, the mixture was diluted with water, and extracted with chloroform. Subsequently, the mixture was washed with a saturated saline solution, dried over magnesium sulfate and then concentrated. After that, the mixture was purified by silica gel chromatography and then recrystallized from ethyl acetate to obtain a compound (550 mg, 0.992 mmol, yield: 47%). The compound showed, as a result of a mass analysis, m/e=554, and was identified as the compound (3) (exact mass: 554.18).

Example 4

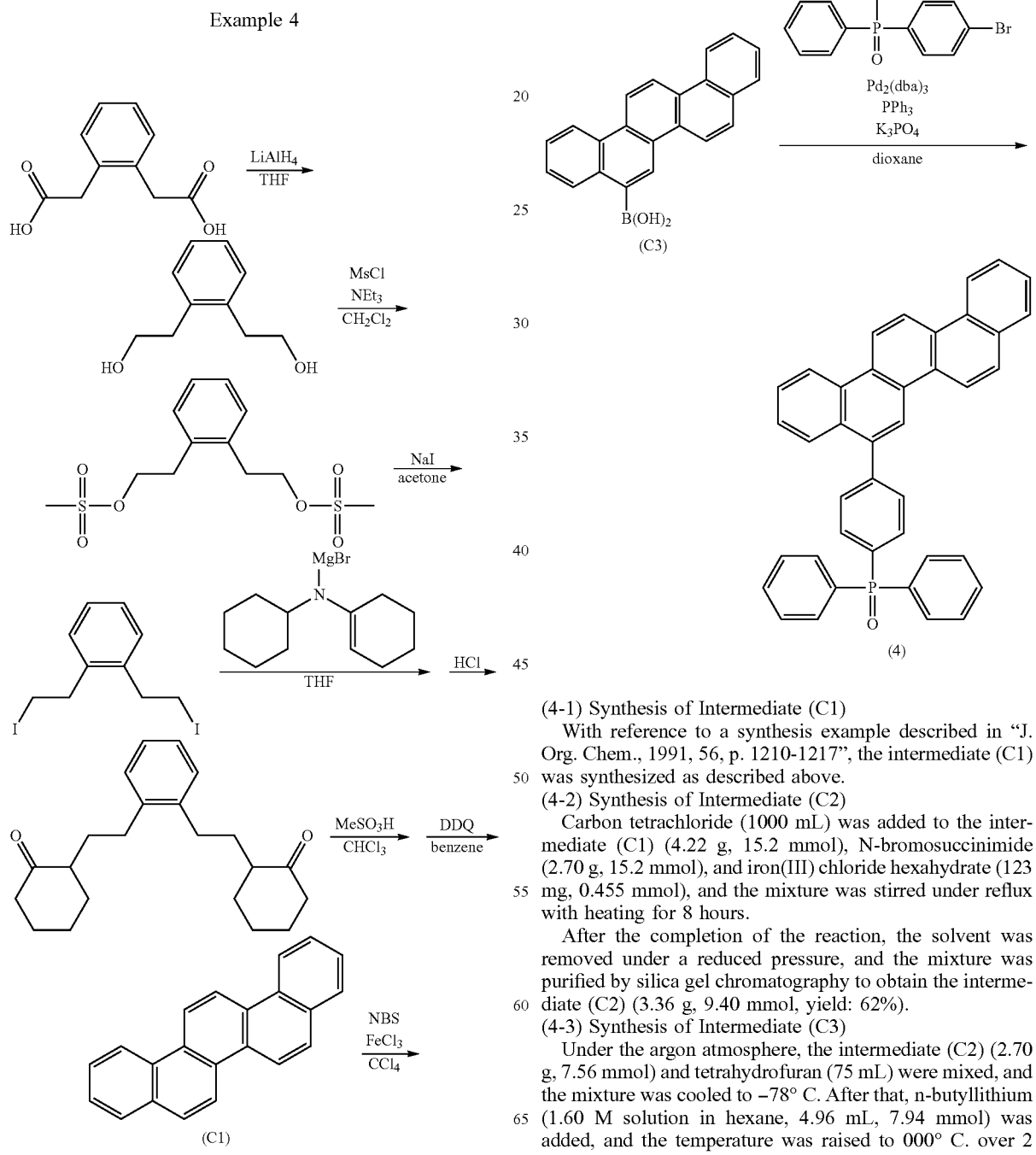

(4-1) Synthesis of Intermediate (C1)

With reference to a synthesis example described in "J. Org. Chem., 1991, 56, p. 1210-1217", the intermediate (C1) was synthesized as described above.

(4-2) Synthesis of Intermediate (C2)

Carbon tetrachloride (1000 mL) was added to the intermediate (C1) (4.22 g, 15.2 mmol), N-bromosuccinimide (2.70 g, 15.2 mmol), and iron(III) chloride hexahydrate (123 mg, 0.455 mmol), and the mixture was stirred under reflux with heating for 8 hours.

After the completion of the reaction, the solvent was removed under a reduced pressure, and the mixture was purified by silica gel chromatography to obtain the intermediate (C2) (3.36 g, 9.40 mmol, yield: 62%).

(4-3) Synthesis of Intermediate (C3)

Under the argon atmosphere, the intermediate (C2) (2.70 g, 7.56 mmol) and tetrahydrofuran (75 mL) were mixed, and the mixture was cooled to −78° C. After that, n-butyllithium (1.60 M solution in hexane, 4.96 mL, 7.94 mmol) was added, and the temperature was raised to 000° C. over 2 hours. Next, the mixture was cooled again to −78° C., trimethoxyborane (1.96 g, 18.9 mmol) was added thereto, the mixture was stirred at −78° C. for 15 minutes, and the temperature was raised to a room temperature over 8 hours.

After the completion of the reaction, an aqueous hydrogen chloride solution (1 M, 15 mL) was added, and the mixture was stirred at a room temperature for 1 hour, and extracted with ethyl acetate. The solution was dried over magnesium sulfate, then concentrated, suspended in and washed with hexane, and collected by filtration to obtain the intermediate (C3) (1.73 g, 5.37 mmol, yield: 71%).

(4-4) Synthesis of Compound (4)

Under the argon atmosphere, 1,4-dioxane (50 mL) was added to the intermediate (C3) (1.50 g, 4.66 mmol), (4-bromophenyl)phosphine oxide (1.66 g, 4.66 mmol), tris(dibenzylideneacetone)dipalladium(0) (64 mg, 0.0699 mmol), triphenylphosphine (147 mg, 0.559 mmol), and tripotassium phosphate (5.94 g, 28.0 mmol), and the mixture was stirred at 100° C. for 6 hours.

After the completion of the reaction, the mixture was diluted with water, and extracted with chloroform. Subsequently, the mixture was washed with a saturated saline solution, dried over magnesium sulfate and then concentrated. After that, the mixture was purified by silica gel chromatography and then recrystallized from ethyl acetate to obtain a compound (1.94 g, 3.50 mmol, yield: 75%). The compound showed, as a result of a mass analysis, m/e=554, and was identified as the compound (4) (exact mass: 554.18).

Example 5

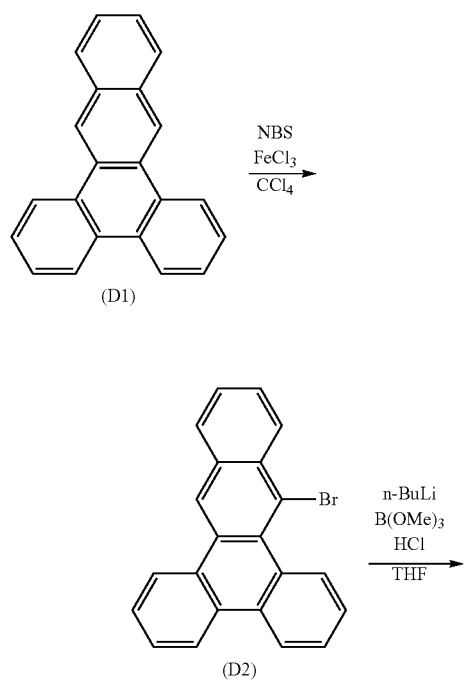

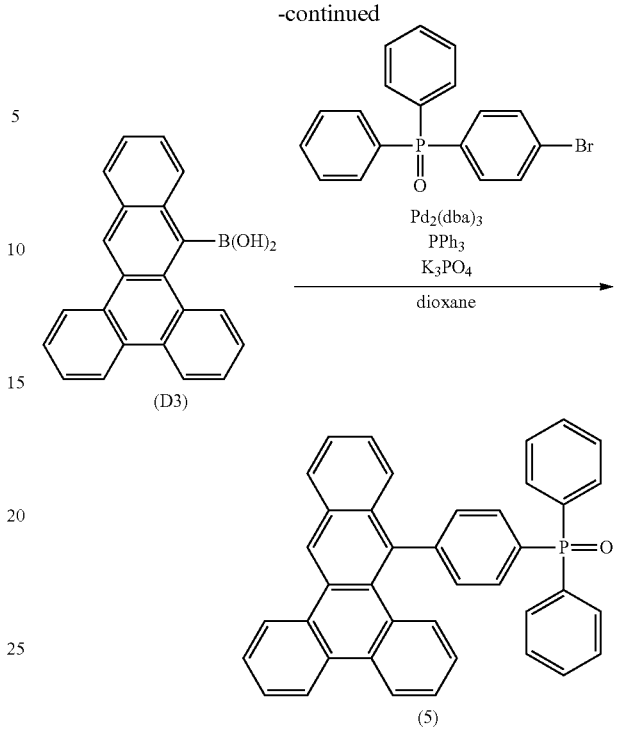

(5-1) Synthesis of Intermediate (D1)

With reference to a synthesis example described in "J. Org. Chem., 2004, 69, p. 8445-8450", the intermediate (D1) was synthesized as described above.

(5-2) Synthesis of Intermediate (D2)

Carbon tetrachloride (1500 mL) was added to the intermediate (D1) (6.25 g, 22.5 mmol), N-bromosuccinimide (4.00 g, 22.5 mmol), and iron(III) chloride hexahydrate (182 mg, 0.675 mmol), and the mixture was stirred under reflux with heating for 6 hours.

After the completion of the reaction, the solvent was removed under a reduced pressure, and the mixture was purified by silica gel chromatography to obtain the intermediate (D2) (5.55 g, 15.5 mmol, yield: 69%).

(5-3) Synthesis of Intermediate (D3)

Under the argon atmosphere, the intermediate (D2) (3.00 g, 8.40 mmol) and tetrahydrofuran (80 mL) were mixed, and the mixture was cooled to −78° C. After that, n-butyllithium (1.60 M solution in hexane, 5.51 mL, 8.82 mmol) was added, and the temperature was raised to 0° C. over 2 hours. Next, the mixture was cooled again to −78° C., trimethoxyborane (2.30 g, 22.1 mmol) was added thereto, the mixture was stirred at −78° C. for 20 minutes, and then the temperature was raised to a room temperature over 8 hours.

After the completion of the reaction, an aqueous hydrogen chloride solution (1 M, 20 mL) was added, and the mixture was stirred at a room temperature for 1 hour and extracted with ethyl acetate. The solution was dried over magnesium sulfate, then concentrated, suspended in and washed with hexane, and collected by filtration to obtain the intermediate (D3) (1.76 g, 5.46 mmol, yield: 65%).

(5-4) Synthesis of Compound (5)

Under the argon atmosphere, 1,4-dioxane (50 mL) was added to the intermediate (D3) (1.65 g, 5.12 mmol), (4-bromophenyl)phosphine oxide (1.83 g, 5.12 mmol), tris(dibenzylideneacetone)dipalladium(0) (70 mg, 0.0768 mmol), triphenylphosphine (147 mg, 0.559 mmol), and tripotassium phosphate (6.53 g, 30.8 mmol), and the mixture was stirred at 100° C. for 8 hours.

After the completion of the reaction, the mixture was diluted with water and extracted with chloroform. Subsequently, the mixture was washed with a saturated saline solution, dried over magnesium sulfate and then concentrated. After that, the mixture was purified by silica gel chromatography and then recrystallized from ethyl acetate to obtain a compound (1.68 g, 3.02 mmol, yield: 59%). The compound showed, as a result of a mass analysis, m/e=554, and was identified as the compound (5) (exact mass: 554.18).

Example 6

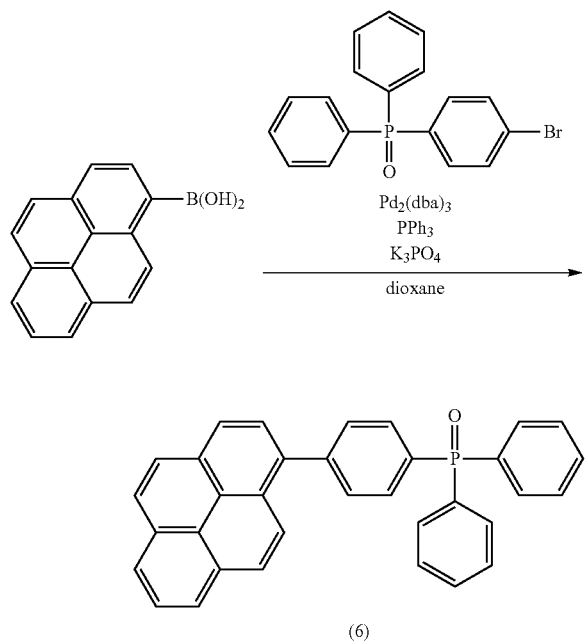

(6)

Under the argon atmosphere, 1,4-dioxane (100 mL) was added to 1-pyrenylboronic acid (2.21 g, 9.00 mmol), (4-bromophenyl)phosphine oxide (3.21 g, 9.00 mmol), tris(dibenzylideneacetone)dipalladium(0) (124 mg, 0.135 mmol), triphenylphosphine (283 mg, 1.08 mmol), and tripotassium phosphate (11.5 g, 54.0 mmol), and the mixture was stirred at 100° C. for 7 hours.

After the completion of the reaction, the mixture was diluted with water and extracted with chloroform. Subsequently, the mixture was washed with a saturated saline solution, dried over magnesium sulfate and then concentrated. After that, the mixture was purified by silica gel chromatography and then recrystallized from ethyl acetate to obtain a compound (1.77 g, 3.69 mmol) (yield: 41%). The compound showed, as a result of a mass analysis, m/e=478, and was identified as the compound (6) (exact mass: 478.15).

Example 7

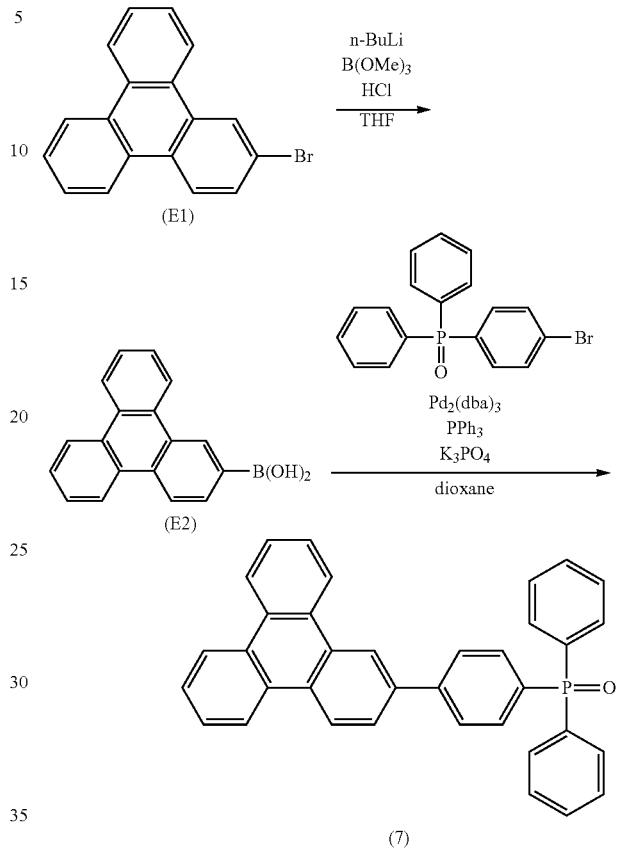

(7)

(7-1) Synthesis of Intermediate (E2)

Under the argon atmosphere, the intermediate (E1) (2.90 g, 9.44 mmol) and tetrahydrofuran (80 mL) were mixed and the mixture was cooled to −78° C. After that, n-butyllithium (1.60 M solution in hexane, 6.20 mL, 9.91 mmol) was added and the temperature was raised to 0° C. over 2 hours. Next, the mixture was cooled again to −78° C., trimethoxyborane (2.58 g, 24.8 mmol) was added, the mixture was stirred at −78° C. for 20 minutes, and the temperature was raised to a room temperature over 8 hours.

After the completion of the reaction, an aqueous hydrogen chloride solution (1 M, 20 mL) was added and the mixture was stirred at a room temperature for 1 hour and extracted with ethyl acetate. The solution was dried over magnesium sulfate, then concentrated, suspended in and washed with hexane, and collected by filtration to obtain the intermediate (E2) (1.46 g, 5.38 mmol, yield: 57%).

(7-2) Synthesis of Compound (7)

Under the argon atmosphere, 1,4-dioxane (50 mL) was added to the intermediate (E2) (1.40 g, 5.14 mmol), (4-bromophenyl)phosphine oxide (1.84 g, 5.14 mmol), tris(dibenzylideneacetone)dipalladium(0) (71 mg, 0.0771 mmol), triphenylphosphine (147 mg, 0.561 mmol), and tripotassium phosphate (6.53 g, 30.8 mmol), and the mixture was stirred at 100° C. for 7 hours.

After the completion of the reaction, the mixture was diluted with water, and extracted with chloroform. Subsequently, the mixture was washed with a saturated saline solution, dried over magnesium sulfate and then concentrated. After that, the mixture was purified by silica gel chromatography and then recrystallized from ethyl acetate to obtain a compound (1.24 g, 2.47 mmol, yield: 48%). The compound showed, as a result of a mass analysis, m/e=504, and was identified as the compound (7) (exact mass: 504.16).

With reference to the synthetic reactions, and by using known reactions and raw materials as needed, all the compounds falling within the scope of the claims can be synthesized.

[Production of Organic Electroluminescence Device]

Next, a specific production method of an organic EL device will be described. Incidentally for each organic EL device in the examples, the driving voltage, the external quantum efficiency and the lifetime were measured according to the following method.

(Methods for Measuring Performances of Organic EL Device)

(1) Driving Voltage

A current was applied between an anode (ITO transparent electrode) and a metal cathode (metal A1) so that the current density was 10 mA/cm$^2$ and then the voltage (unit: V) was measured.

(2) External Quantum Efficiency

A voltage was applied to an organic EL device so that the current density was 10 mA/cm$^2$ and then the spectral emission luminance spectrum was measured with a spectrum emission luminance meter "CS-1000" (manufactured by Konica Minolta, Inc.). From the obtained spectral emission luminance spectrum, the external quantum efficiency (at 10 mA/cm$^2$, unit: %) was calculated under the assumption that the Lambertian emission was made.

With the ratio of the maximum luminous efficiency to the luminous efficiency at 10 mA/cm$^2$, the maximum external quantum efficiency (EQE max.) was calculated from the external quantum efficiency (at 10 mA/cm$^2$).

(3) Lifetime

A continuous current application test of direct current was performed as follows. The initial current density was set to 50 mA/cm$^2$ and the time period in which the luminance is reduced to 97% of the initial luminance of the test (LT 97) was measured.

Example 8 [Production of Organic EL Device]

A glass substrate with an ITO transparent electrode (anode) of 25 mm×75 mm×1.1 mm thickness (manufactured by Geomatic) was subjected to ultrasonic cleaning in isopropyl alcohol for 5 minutes, and then subjected to UV ozone cleaning for 30 minutes. The glass substrate with the transparent electrode line after cleaning was attached to a substrate holder of a vacuum evaporator and the compound K-1 described below was deposited on the surface of the side having the transparent electrode line formed so as to cover the transparent electrode to form a K-1 film of a thickness of 5 nm, thereby forming an acceptor layer.

Next, on the acceptor layer, the compound HT-1 described below was deposited as a first hole transporting material to form an HT-1 film of a thickness of 80 nm, thereby forming a first hole transporting layer.

Next, on the first hole transporting layer, the compound HT-2 described below was deposited to form an HT-2 film of a thickness of 10 nm, thereby forming a second hole transporting layer.

In addition, on the HT-2 film, the compound BH-1 described below and the compound BD-1 described below were co-deposited in a mass ratio of 24:1 to form a film, thereby forming a light emitting layer of a thickness of 25 nm.

Subsequent to the film formation of the light emitting layer, the compound (6) described below and 8-quinolinolato lithium (Liq) were co-deposited in a mass ratio of 50:50 to form a film, thereby forming an electron transporting layer of a thickness of 25 nm.

On the electron transporting layer, Liq was deposited to form an electron injecting layer of a thickness of 1 nm. In addition, on the electron injecting layer, metal A1 was deposited to form a metal cathode of a thickness of 80 nm, whereby an organic EL device was produced.

A configuration of the obtained organic EL device is schematically shown below. Incidentally, the numerals in the parentheses show the thicknesses (unit: nm), and the numerals in the parentheses with % show the concentration by mass of BD-1 in the light emitting layer or the concentration by mass of Liq in the electron transporting layer.

[[ITO (130)/K-1 (5)/HT-1 (80)/HT-2 (10)/BH-1: BD-1 (25, 4%)/compound 6: Liq (25, 50%)/Liq (1)/A1 (80)]]

For the obtained organic EL device, the performances were determined according to the methods described above. The results are shown in Table 1.

(Compounds Used in Example 8)

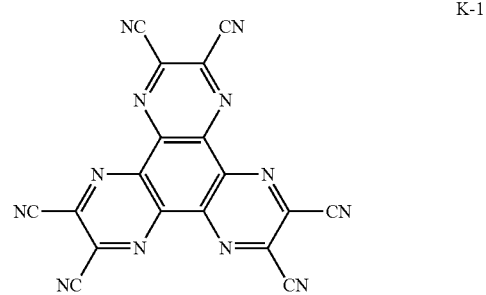

K-1

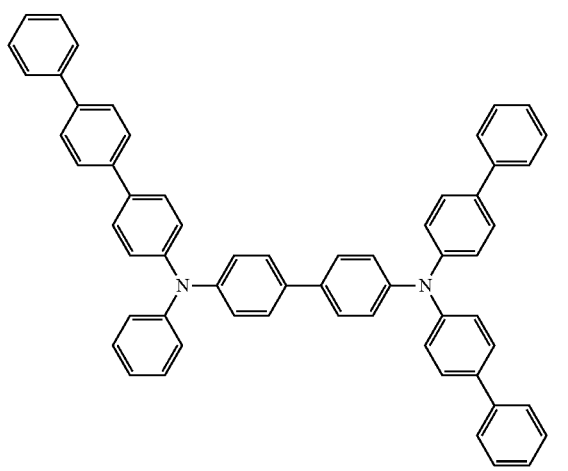

HT-1

-continued

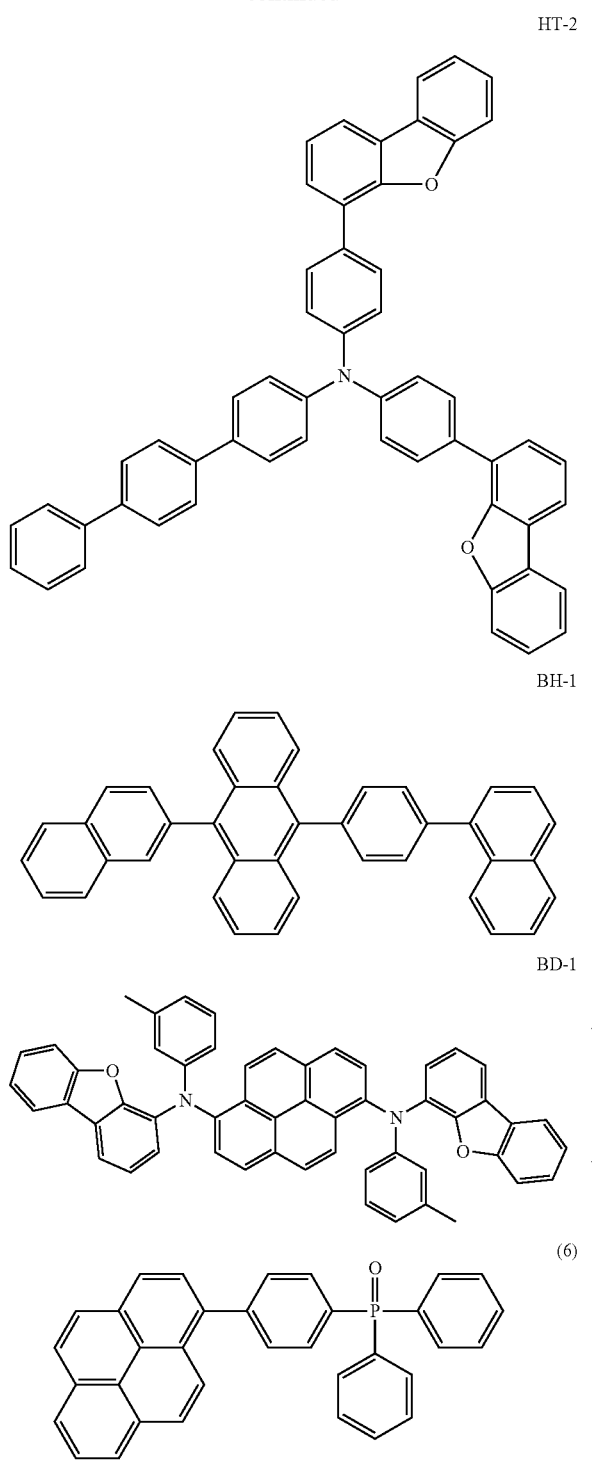

HT-2

BH-1

BD-1

Example 9

In Example 8, an organic EL device was produced in the same manner except that the compound (1) was used in place of the compound (6). For the obtained organic EL device, the performances were determined according to the methods described above. The results are shown in Table 1.

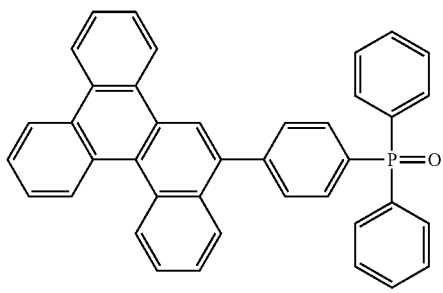

(1)

Comparative Example 1

In Example 8, an organic EL device was produced in the same manner except that the comparative compound 1 was used in place of the compound (6). For the obtained organic EL device, the performances are measured according to the methods described above. The results are shown in Table 1.

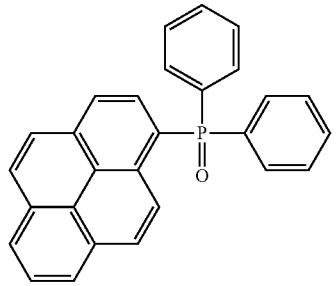

Comparative Compound 1

TABLE 1

| Electron transporting layer Electron transporting material | Measurement result | | |
|---|---|---|---|
| | Driving voltage (V) (10 mA/ cm² · hour) | EQE max (%) | Lifetime (hour) [LT 97] |
| Example 8 Compound (6) | 4.8 | 7.3 | 305 |
| Example 9 Compound (1) | 4.9 | 7.1 | 509 |
| Comparative Example 1 Comparative compound 1 | 4.6 | 7.8 | 10 |

It can be seen from Table 1 that, in the organic EL devices of Example 9 and Example 10 in which the compound (6) and the compound (1) of the present invention were respectively used, as compared with the organic EL device of Comparative Example 1, the lifetime can be prolonged while suitably maintaining the driving voltage and the external quantum efficiency.

REFERENCE SIGNS LIST

1 Organic electroluminescence device
3 Anode
4 Cathode
5 Light emitting layer

6 Hole transporting zone (Hole transporting layer)
7 Electron transporting zone (Electron transporting layer)
10 Organic thin film layer

The invention claimed is:
1. A compound represented by the following general formulae (10), (11), or (13):

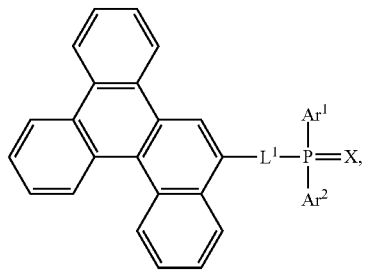
(10)

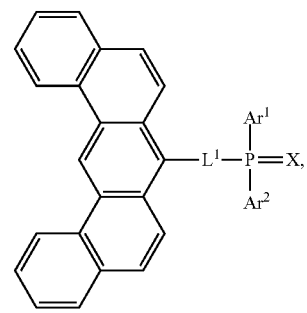
(11)

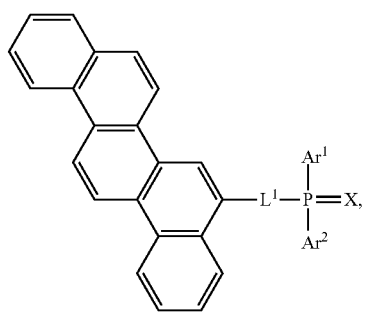
(13)

wherein in the general formulae (10), (11), and (13), X represents an oxygen atom, a sulfur atom or a selenium atom;
$L^1$ represents a substituted or unsubstituted arylene group having 6 to 13 ring carbon atoms; and
$Ar^1$ and $Ar^2$ are each independently a substituted or unsubstituted aryl group having 6 to 60 ring carbon atoms or a substituted or unsubstituted, oxygen-containing or sulfur-containing, heteroaryl group having 5 to 60 ring atoms, and $Ar^1$ and $Ar^2$ may bind to each other to form a ring.

2. The compound according to claim 1, wherein $L^1$ is a substituted or unsubstituted phenylene group, a substituted or unsubstituted biphenylylene group, or a substituted or unsubstituted fluorenylene group.

3. The compound according to claim 1, wherein at least one of $Ar^1$ and $Ar^2$ is a substituted or unsubstituted aryl group having 6 to 60 ring carbon atoms.

4. The compound according to claim 3, wherein $Ar^1$ and $Ar^2$ are both a substituted or unsubstituted aryl group having 6 to 60 ring carbon atoms.

5. The compound according to claim 4, wherein $Ar^1$ and $Ar^2$ are both a substituted or unsubstituted aryl group having 6 to 13 ring carbon atoms.

6. The compound according to claim 4, wherein $Ar^1$ and $Ar^2$ are each independently a substituted or unsubstituted phenyl group, a substituted or unsubstituted naphthyl group, a substituted or unsubstituted biphenylyl group, or a substituted or unsubstituted fluorenyl group.

7. The compound according to claim 1, wherein X is an oxygen atom or a sulfur atom.

8. A material for organic electroluminescence devices, comprising the compound according to claim 1.

9. An organic electroluminescence device, which comprises an anode and a cathode facing to each other, and one or more organic thin layers including at least a light emitting layer which are disposed between the anode and cathode, wherein at least one layer of the organic thin film layers comprises the compound according to claim 1.

10. The organic electroluminescence device according to claim 9, which comprises an electron transporting zone between the light emitting layer and the cathode, wherein the electron transporting zone comprises the compound represented by the following general formulae (10), (11), or (13):

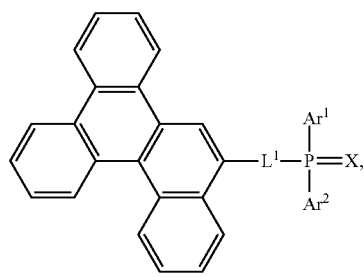
(10)

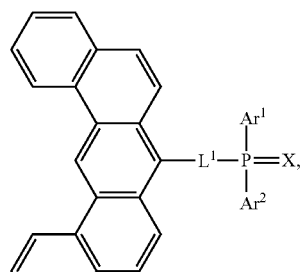
(11)

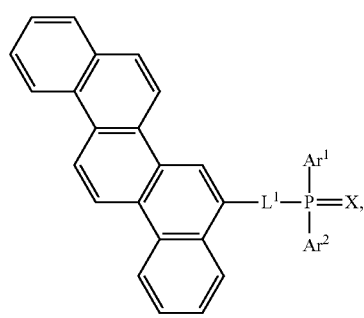
(13)

wherein in the general formulae (10), (11), and (13), X represents an oxygen atom, a sulfur atom or a selenium atom;
$L^1$ represents a substituted or unsubstituted arylene group having 6 to 13 ring carbon atoms; and Ar$^1$ and Ar$^2$ are each independently a substituted or unsubstituted aryl group having 6 to 60 ring carbon atoms or a substituted or unsubstituted, oxygen-containing or sulfur-containing, heteroaryl group having 5 to 60 ring atoms, and Ar$^1$ and Ar$^2$ may bind to each other to form a ring.

11. The organic electroluminescence device according to claim 10, wherein the electron transporting zone further comprises at least one selected from an electron donating dopant and an organic metal complex.

12. The organic electroluminescence device according to claim 11, wherein the electron donating dopant is at least one selected from an alkali metal, an alkali metal compound, an alkaline earth metal, an alkaline earth metal compound, a rare earth metal, and an rare earth metal compound.

13. The organic electroluminescence device according to claim 11, wherein the organic metal complex is at least one selected form an organic metal complex containing an alkali metal, an organic metal complex containing an alkaline earth metal, and an organic metal complex containing a rare earth metal.

14. An electronic equipment provided with an organic electroluminescence device according to claim 9.

15. The compound according to claim 1, wherein the compound represented by the general formula (10).

16. The compound according to claim 1, wherein the compound represented by the general formula (11).

17. The compound according to claim 1, wherein the compound represented by the general formula (13).

18. The organic electroluminescence device according to claim 10, wherein the compound represented by the general formula (13).

19. The organic electroluminescence device according to claim 10, wherein the compound represented by the general formula (10).

20. The organic electroluminescence device according to claim 10, wherein the compound represented by the general formula (13).

* * * * *